(12) United States Patent
Li et al.

(10) Patent No.: US 11,584,759 B2
(45) Date of Patent: Feb. 21, 2023

(54) MACROCYCLIC KINASE INHIBITOR

(71) Applicant: HITGEN INC., Sichuan (CN)

(72) Inventors: Jin Li, Sichuan (CN); Dengyou Zhang, Sichuan (CN); Jingchao Feng, Sichuan (CN); Zhi Wang, Sichuan (CN); Leichang Pan, Sichuan (CN); Jing Hu, Sichuan (CN); Wei Chen, Sichuan (CN)

(73) Assignee: HITGEN INC., Sichuan (CN)

( * ) Notice: Subject to any disclaimer, the term of this patent is extended or adjusted under 35 U.S.C. 154(b) by 331 days.

(21) Appl. No.: 17/048,604

(22) PCT Filed: Apr. 17, 2019

(86) PCT No.: PCT/CN2019/083086
§ 371 (c)(1),
(2) Date: Oct. 18, 2020

(87) PCT Pub. No.: WO2019/201282
PCT Pub. Date: Oct. 24, 2019

(65) Prior Publication Data
US 2021/0147443 A1 May 20, 2021

(30) Foreign Application Priority Data

Apr. 18, 2018 (CN) .......................... 201810341398.3

(51) Int. Cl.
*A61P 35/04* (2006.01)
*C07D 471/22* (2006.01)
*C07D 498/22* (2006.01)

(52) U.S. Cl.
CPC ............ *C07D 498/22* (2013.01); *A61P 35/04* (2018.01); *C07D 471/22* (2013.01)

(58) Field of Classification Search
CPC ...... C07D 498/22; C07D 471/22; A61P 35/04
See application file for complete search history.

(56) References Cited

U.S. PATENT DOCUMENTS

| 2005/0058913 A1* | 6/2005 | Freyne et al. ....... C07D 498/18 |
| 2016/0166574 A1 | 6/2016 | Hoelzemann et al. |
| 2018/0186813 A1 | 7/2018 | Cui et al. |
| 2022/0017512 A1 | 1/2022 | Jiang et al. |

FOREIGN PATENT DOCUMENTS

| CN | 1894260 A | 1/2007 |
| CN | 102757448 A | 10/2012 |
| CN | 105164136 A | 12/2015 |
| CN | 107735399 A | 2/2018 |
| WO | 2005058913 A1 | 6/2005 |
| WO | 2010085597 A1 | 7/2010 |
| WO | 2012125668 A1 | 9/2012 |
| WO | 2020098723 A1 | 5/2020 |

OTHER PUBLICATIONS

Search Report dated Mar. 22, 2021 for European patent application No. 19788896.9.
Zahn, P.K. et al."Effect of Blockade of Nerve Growth Factor and Tumor Necrosis Factor on Pain Behaviors After Plantar Incision", The Journal of Pain,vol. 5, No. 3 Apr. 2004: pp. 157-163.
Shelton, D.L. et al.,"Nerve growth factor mediates hyperalgesia and cachexia in auto-immune arthritis", Pain, 2005 (116): 8-16.
Matayoshi, S. et al.,"Actions of brain-derived neurotrophic factor on spinal nociceptive transmission during inflammation in the rat", J. Physiol, 2005 (569): 685-695.
Thompson, S.W. et al., "Brain-derived neurotrophic factor is an endogenous modulator of nociceptive responses in the spinal cord", Proc. Natl. Acad. Sci., 1999 (96): 7714-7718.
Li, C.Q. et al., "Brain derived neurotrophic factor (BDNF) contributes to the pain hypersensitivity following surgical incision in the rats", Molecular Pain, 2008 (28): 1-11.
Brodeur, G.M. et al., "Neuroblastoma: Biological Insights Into a Clinical Enigma", Nat. Rev. Cancer, 2003 (3): 203-216.
Truzzi, F. et al., "Neurotrophins in healthy and diseased skin",Dermato-Endocrinology, 2011 (1): 32-36.
Jin, W. et al., "TrkC plays an essential role in breast tumor growth and metastasis",Carcinogenesis, 2010 (11): 1939-1947.
Du, J. et. al., "Expression of NGF family and their receptors in gastric carcinoma: A cDNA microarray study", World J. Gastroenterology, 2003 (7): 1431-1434.
Pierottia, M.A. et al., "Oncogenic rearrangements of the NTRK1/NGF receptor", Cancer Letters, 2006 (232): 90-98.
Eric Adriaenssens, E. et al., "Nerve Growth Factor is a Potential Therapeutic Target in Breast Cancer", Cancer Res, 2008 (68): 346-351.
Freund, M.V. et al., "The nerve growth factor and its receptors in airway inflammatory diseases", Pharmacology & Therapeutics, 2008 (117): 52-76.
Viola, F.F. et al., "Nerve growth factor and Trk high affinity receptor (TrkA) gene expression in inflammatory bowel disease", Gut, 2000 (46): 670-678.
Dou, Y.C., "Increased nerve growth factor and its receptors in atopic dermatitis: an immunohistochemical study", Arch. Derma. Res., 2006 (298): 31-37.
Sohrabji, F. et al., "Estrogen-BDNF interactions: Implications for neurodegenerative diseases", Neuroendocrinology, 2006 (27): 404-414.
International Search Report for PCT/CN2019/083086 dated Jul. 23, 2019, ISA/CN.
First Office Action dated Dec. 8, 2021 for Japanese patent application No. 2021-506030, English translation provided by Global Dossier.

* cited by examiner

*Primary Examiner* — Erich A Leeser
(74) *Attorney, Agent, or Firm* — Yue (Robert) Xu; Apex Attorney at law, LLP

(57) ABSTRACT

Disclosed is a macrocyclic kinase inhibitor, wherein the compound, or a stereoisomer thereof, or a pharmaceutically acceptable salt thereof is as shown in formula I. Experiments show that the new compound as shown in formula I disclosed in the present invention exhibits an excellent TRK inhibitory activity, has a significant inhibitory effect on TRKA-mutant cell growth, and exhibits an excellent inhibitory effect on in vivo tumor growth, thus providing a new choice for the clinical treatment of diseases associated with abnormal TRK activity.

14 Claims, 2 Drawing Sheets

MACROCYCLIC KINASE INHIBITOR

The present application is the national phase of International Application No. PCT/CN2019/083086, titled "MACROCYCLIC KINASE INHIBITOR", which claims the priority to Chinese Patent Application No. 201810341398.3, titled "MACROCYCLIC KINASE INHIBITOR", filed on Apr. 18, 2018 with the Chinese Patent Office, the entire disclosure thereof is incorporated herein by reference.

FIELD

The invention relates to a macrocyclic compound and the use thereof in the manufacture of a medicament.

BACKGROUND

The tropomyosin receptor kinase (Trk) family is a class of receptor tyrosine kinases, and includes three members: TrkA, TrkB, and TrkC. After being activated by neurotrophic factors, Trk affects the survival and differentiation of neurons and significantly affects the function of neurons through various signaling pathways.

It has been reported that inhibitors of the Trk/neurotrophic factor pathway are effective in many animal pain models (Zahn, P. K. et al. J. Pain, 2004 (5): 157-163; Shelton, D L. et al Pain, 2005 (116): 8-16). In addition, the neurotrophic factors secreted by tumor cells and tumor infiltrating macrophages directly stimulate TrkA on peripheral pain fibers. It has been reported that the activation of the TrkB pathway can regulate several types of pain, including inflammatory pain (Matayoshi, S. et al. J. Physiol, 2005 (569): 685-695), neuropathic pain (Thompson, S. W. et al. Proc. Natl. Acad. Sci., 1999 (96): 7714-7718) and surgical pain (Li, C. Q. et al. Molecular Pain, 2008 (28): 1-11).

It has been reported that overexpression, activation, amplification and/or mutation of Trk are associated with a variety of cancers, including neurocytoma (Brodeur, G M et al. Nat. Rev. Cancer, 2003 (3): 203-216), melanoma (Truzzi, F. et al. Dermato-Endocrinology, 2008 (1): 32-36), breast cancer (Jin, W. et al Carcinogenesis, 2010 (11): 1939-1947) and gastric cancer (Du, J. et. al. World J. Gastroenterology, 2003 (7): 1431-1434) etc. In preclinical models, non-selective small molecule inhibitors of TrkA, TrkB, and TrkC effectively inhibited tumor growth and terminated tumor metastasis (Pierottia, M. A. et al. Cancer Letters, 2006 (232): 90-98; Eric Adriaenssens, E. et al. Cancer Res, 2008 (68): 346-351).

It has also been reported that non-selective small molecule inhibitors of TrkA, TrkB and TrkC are effective in preclinical models of inflammatory diseases including asthma (Freund, M. V. et al. Pharmacology & Therapeutics, 2008 (117): 52-76), inflammatory bowel disease (Mola, F. F. et al. Gut, 2000 (46): 670-678) and specific dermatitis (Dou, Y. C. Arch Derma Res., 2006 (298): 31-37), etc.

It is also reported that the Trk/neurotrophic factor pathway is involved in neurodegenerative diseases, including multiple sclerosis, Parkinson's disease and Alzheimer's disease (Sohrabji, F. et al. Neuroendocrinology, 2006 (27): 404-414).

Therefore, there is a need to further develop small molecule inhibitors of Trk for the treatment of pain, cancer, inflammation, neurological retirement diseases and the like.

SUMMARY

In order to solve the above problems, the present invention provides a class of macrocyclic kinase inhibitors.

The present invention provides a compound as shown in formula I, or a stereoisomer thereof, or a pharmaceutically acceptable salt thereof:

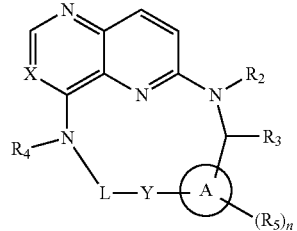

Formula I wherein
X is selected from CR or N;
$R_1$ is selected from hydrogen, halogen, $C_{1-10}$ alkyl, $C_{2-10}$ alkenyl, $C_{2-10}$ alkynyl, 3-10 membered cycloalkyl, 3-10 membered heterocycloalkyl, —CN, —NO$_2$, —OR$_a$, —OC(O)R$_a$, —OC(O)NR$_a$R$_b$, —OS(O)$_2$R$_a$, —SR$_a$, —S(O)$_2$R$_a$, —S(O)$_2$NR$_a$R$_b$, —OS(O)$_2$NR$_a$R$_b$, —C(O)R$_a$, —C(O)OR$_a$, —C(O)NR$_a$R$_b$, —NR$_a$R$_b$, —NR$_a$C(O)R$_b$, —NR$_a$C(O)OR$_b$, —NR$_a$C(O)NR$_a$R$_b$, —NR$_a$S(O)$_2$R$_b$, or —NR$_a$S(O)$_2$NR$_a$R$_b$; wherein the alkyl, alkenyl, alkynyl, cycloalkyl, and heterocycloalkyl are substituted with m R$_c$;
$R_2$ is selected from hydrogen, $C_{1-10}$ alkyl, 3-10 membered cycloalkyl, 3-10 membered heterocycloalkyl, —S(O)$_2$R$_a$, —S(O)$_2$NR$_a$R$_b$, —C(O)R$_a$, —C(O)OR$_a$, and —C(O)NR$_a$R$_b$, wherein the alkyl, cycloalkyl, and heterocycloalkyl are substituted with m R$_c$;
$R_3$ is selected from hydrogen, halogen, $C_{1-10}$ alkyl, $C_{2-10}$ alkenyl, $C_{2-10}$ alkynyl, 3-10 membered cycloalkyl, 3-10 membered heterocycloalkyl, —CN, —NO$_2$, —OR$_a$, —C(O)R$_a$, —C(O)OR$_a$, —C(O)NR$_a$R$_b$, —NR$_a$R$_b$, and —NR$_a$C(O)R$_b$; wherein the alkyl, alkenyl, alkynyl, cycloalkyl, and heterocycloalkyl are substituted with m R$_c$;
or $R_2$ and $R_3$ are connected to form a 4-10-membered heterocycle; wherein the formed heterocycle is substituted with m R$_c$;
$R_4$ is selected from hydrogen, $C_{1-10}$ alkyl, 3-10 membered cycloalkyl, 3-10 membered heterocycloalkyl, —S(O)$_2$R$_a$, —S(O)$_2$NR$_a$R$_b$, —C(O)R$_a$, —C(O)OR$_a$, and —C(O)NR$_a$R$_b$; wherein the alkyl, cycloalkyl, and heterocycloalkyl are substituted with m R$_c$;
ring A is selected from a benzene ring, a naphthalene ring, and a 5-10 membered aromatic heterocycle;
n is 1, 2, 3, or 4;
$R_5$ is independently selected from hydrogen, halogen, $C_{1-10}$ alkyl, $C_{2-10}$ alkenyl, $C_{2-10}$ alkynyl, 3-10 membered cycloalkyl, 3-10 membered heterocycloalkyl, —CN, —NO$_2$, —OR$_a$, —OC(O)R$_a$, —OC(O)NR$_a$R$_b$, —OS(O)$_2$R$_a$, —SR$_a$, —S(O)$_2$R$_a$, —S(O)$_2$NR$_a$R$_b$, —OS(O)$_2$NR$_a$R$_b$, —C(O)R$_a$, —C(O)OR$_a$, —C(O)NR$_a$R$_b$, —NR$_a$R$_b$, —NR$_a$C(O)R$_b$, —NR$_a$C(O)OR$_b$, —NR$_a$C(O)NR$_a$R$_b$, —NR$_a$S(O)$_2$R$_b$, and —NR$_a$S(O)$_2$NR$_a$R$_b$; wherein the alkyl, alkenyl, alkynyl, cycloalkyl, and heterocycloalkyl are substituted with m R$_c$;
Y is selected from O, S, —NR$_a$, and —C(R$_a$R$_b$)—;
L is selected from $C_{1-10}$ alkylene, $C_{2-10}$ alkenylene, and $C_{2-10}$ alkynylene; wherein the alkylene, alkenylene, and alkynylene are substituted with m R$_c$;
m is independently 0, 1, 2, 3, or 4;
$R_a$ and $R_b$ are independently selected from hydrogen, $C_{10-10}$ alkyl, $C_{20-10}$ alkenyl, $C_{20-10}$ alkynyl, 3-10 membered cycloalkyl, and 3-10 membered heterocycloalkyl; and $R_c$ is independently selected from $C_{10-10}$ alkyl, halogen, —CN, —NO$_2$, —OR$_a$, —OC(O)R$_a$, —OS(O)$_2$R$_a$, —SR$_a$, —S(O)$_2$R$_a$, —S(O)$_2$NR$_a$R$_b$, —C(O)R$_a$, —C(O)OR$_a$, —C(O)NR$_a$R$_b$, —NR$_a$R$_b$, —NR$_a$C(O)R$_b$, and —NR$_a$S(O)$_2$R$_b$.

Further, $R_1$ is selected from hydrogen, halogen, $C_{1-6}$ alkyl, $C_{2-6}$ alkenyl, $C_{2-6}$ alkynyl, 3-6 membered cycloalkyl, 3-6 membered heterocycloalkyl, —CN, —NO$_2$, —OR$_a$, —OC(O)R$_a$, —OC(O)NR$_a$R$_b$, —OS(O)$_2$R$_a$, —SR$_a$, —S(O)$_2$R$_a$, —S(O)$_2$NR$_a$R$_b$, —OS(O)$_2$NR$_a$R$_b$, —C(O)R$_a$, —C(O)OR$_a$, —C(O)NR$_a$R$_b$, —NR$_a$R$_b$, —NR$_a$C(O)R$_b$, —NR$_a$C(O)OR$_b$, —NR$_a$C(O)NR$_a$R$_b$, —NR$_a$S(O)$_2$R$_b$, and —NR$_a$S(O)$_2$NR$_a$R$_b$; wherein the alkyl, alkenyl, alkynyl, cycloalkyl, and heterocycloalkyl are substituted with m R$_c$;

$R_2$ is selected from hydrogen, $C_{1-6}$ alkyl, 3-6 membered cycloalkyl, 3-6 membered heterocycloalkyl, —S(O)$_2$R$_a$, and —C(O)R$_a$; wherein the alkyl, cycloalkyl, heterocycloalkyl are substituted with m R$_c$;

$R_3$ is selected from hydrogen, halogen, $C_{1-6}$ alkyl, $C_{2-6}$ alkenyl, $C_{2-6}$ alkynyl, 3-6 membered cycloalkyl, 3-6 membered heterocycloalkyl, —CN, —NO$_2$, —OR$_a$, —C(O)R$_a$, —C(O)OR$_a$, —C(O)NR$_a$R$_b$, —NR$_a$R$_b$, and —NR$_a$C(O)R$_b$; wherein the alkyl, alkenyl, alkynyl, cycloalkyl, heterocycloalkyl are substituted with m R$_c$;

or $R_2$ and $R_3$ are connected to form a 4-8 membered heterocycle; wherein the formed heterocycle is substituted with m R$_c$;

$R_4$ is selected from hydrogen, $C_{1-6}$ alkyl, 3-6 membered cycloalkyl, 3-6 membered heterocycloalkyl, —S(O)$_2$R$_a$, and —C(O)R$_a$ wherein the alkyl, cycloalkyl, and heterocycloalkyl are substituted with m R$_c$;

ring A is selected from a benzene ring and a 5-6 membered aromatic heterocycle;

n is 1, 2, or 3;

$R_5$ is independently selected from hydrogen, halogen, $C_{1-6}$ alkyl, $C_{2-6}$ alkenyl, $C_{2-6}$ alkynyl, 3-6 membered cycloalkyl, 3-6 membered heterocycloalkyl, —CN, —NO$_2$, —OR$_a$, —OC(O)R$_a$, —OS(O)$_2$R$_a$, —SR$_a$, —S(O)$_2$R$_a$, —S(O)$_2$NR$_a$R$_b$, —C(O)R$_a$, —C(O)OR$_a$, —C(O)NR$_a$R$_b$, —NR$_a$R$_b$, —NR$_a$C(O)R$_b$, and —NR$_a$S(O)$_2$R$_b$; wherein the alkyl, alkenyl, alkynyl, cycloalkyl, and heterocycloalkyl are substituted with m R$_c$;

L is selected from $C_{1-6}$ alkylene, $C_{2-6}$ alkenylene and $C_{2-6}$ alkynylene; wherein the alkylene, alkenylene and alkynylene are substituted with m R$_c$;

M is independently 0, 1, 2, or 3; and $R_a$ and $R_b$ are independently selected from hydrogen, $C_{1-6}$, alkyl, $C_{2-6}$ alkenyl, $C_{2-6}$ alkynyl, 3-6 membered cycloalkyl, and 3-6 membered heterocycloalkyl.

Further $R_1$ is selected from hydrogen, halogen, $C_{1-6}$ alkyl, 3-6 membered cycloalkyl, 3-6 membered heterocycloalkyl, —CN, —NO$_2$, —OR$_a$, —OC(O)R$_a$, —OS(O)$_2$R$_a$, —SR$_a$, —S(O)$_2$R$_a$, —S(O)$_2$NR$_a$R$_b$, —C(O)R$_a$, —C(O)OR$_a$, —C(O)NR$_a$R$_b$, —NR$_a$R$_b$, —NR$_a$C(O)R$_b$, and —NR$_a$S(O)$_2$R$_b$; wherein the alkyl, cycloalkyl, and heterocycloalkyl are substituted with m R$_c$;

$R_2$ is selected from hydrogen, $C_{1-6}$ alkyl, 3-6 membered cycloalkyl, and 3-6 membered heterocycloalkyl; wherein the alkyl, cycloalkyl, and heterocycloalkyl are substituted with m R$_c$;

$R_3$ is selected from hydrogen, halogen, $C_{1-6}$ alkyl, 3-6 membered cycloalkyl, 3-6 membered heterocycloalkyl, —CN, —NO$_2$, —OR$_a$, —C(O)R$_a$, —C(O)OR$_a$, —C(O)NR$_a$R$_b$, and —NR$_a$R$_b$; wherein the alkyl, cycloalkyl, and heterocycloalkyl are substituted with m R$_c$;

or $R_2$ and $R_3$ are connected to form a 4-6-membered heterocycle; wherein the formed heterocycle is substituted with m R$_c$;

$R_4$ is selected from hydrogen, $C_{1-6}$ alkyl, —S(O)$_2$R$_a$, and —C(O)R$_a$; wherein the alkyl is substituted with m R$_c$;

n is 1, or 2;

$R_5$ is independently selected from hydrogen, halogen, $C_{1-6}$ alkyl, $C_{2-6}$ alkenyl, $C_{2-6}$ alkynyl, 3-6 membered cycloalkyl, 3-6 membered heterocycloalkyl, —CN, —NO$_2$, —OR$_a$, —SR$_a$, —S(O)$_2$R$_a$, —S(O)$_2$NR$_a$R$_b$, —C(O)R$_a$, —C(O)OR$_a$, —C(O)NR$_a$R$_b$, —NR$_a$R$_b$, —NR$_a$C(O)R$_b$, and —NR$_a$S(O)$_2$R$_b$; wherein the alkyl, alkenyl, alkynyl, cycloalkyl, and heterocycloalkyl are substituted with m R$_c$;

L is selected from $C_{1-6}$ alkylene; wherein the alkylene is substituted with m R$_c$; and m is independently 0, 1, or 2.

Further, $R_1$ is selected from hydrogen, halogen, $C_{1-6}$ alkyl, —CN, —NO$_2$, —OR$_a$, —C(O)R$_a$, —C(O)OR$_a$, —C(O)NR$_a$R$_b$, —NR$_a$R$_b$, —NR$_a$C(O)R$_b$, wherein the alkyl is substituted with m R$_c$;

$R_2$ is selected from hydrogen and $C_{1-6}$ alkyl; wherein the alkyl is substituted with m R$_c$;

$R_3$ is selected from hydrogen, halogen, $C_{1-6}$ alkyl, —CN, —NO$_2$, —OR$_a$, and —NR$_a$R$_b$; wherein the alkyl is substituted with m R$_c$;

or $R_2$ and $R_3$ are connected to form a 5-membered heterocycle; wherein the formed heterocycle is substituted with m R$_c$;

$R_4$ is selected from hydrogen and $C_{1-6}$ alkyl; wherein the alkyl is substituted with m R$_c$;

ring A is selected from a benzene ring and a pyridine ring;

$R_5$ is independently selected from hydrogen, halogen, $C_{1-6}$ alkyl, —CN, —NO$_2$, —OR$_a$, and —NR$_a$R$_b$; wherein the alkyl is substituted with m R$_c$;

$R_a$ and $R_b$ are independently selected from hydrogen and $C_{1-6}$ alkyl; and $R_c$ is independently selected from $C_{1-6}$ alkyl, halogen, —CN, —NO$_2$, —OR$_a$, and —NR$_a$R$_b$.

Further, the compound as shown in formula I, or a stereoisomer thereof, or a pharmaceutically acceptable salt is shown in Formula II:

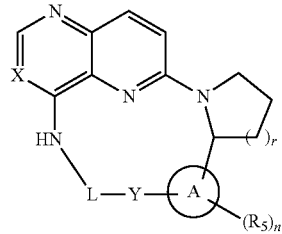

Formula II wherein

X is selected from CR$_1$ or N:

$R_1$ is selected from hydrogen, halogen, —CN, —C(O)R$_a$, —C(O)OR$_a$, and —C(O)NR$_a$R$_b$;

ring A is selected from a benzene ring, a naphthalene ring and a 5-10 membered aromatic heterocycle;

n is 1, 2, 3, or 4;

$R_5$ is independently selected from hydrogen and halogen;

Y is selected from O, —NR$_a$—, and —C(R$_a$R$_b$)—;

$R_a$ and $R_b$ are independently selected from hydrogen and $C_{10-10}$ alkyl;

L is selected from $C_{1-10}$ alkylene; wherein the alkylene is substituted with m $R_c$;
r is 0, 1, 2, 3, or 4; and
m is 0, 1, 2, 3, or 4.
Further, the compound as shown in formula II, or a stereoisomer thereof, or a pharmaceutically acceptable salt thereof is:
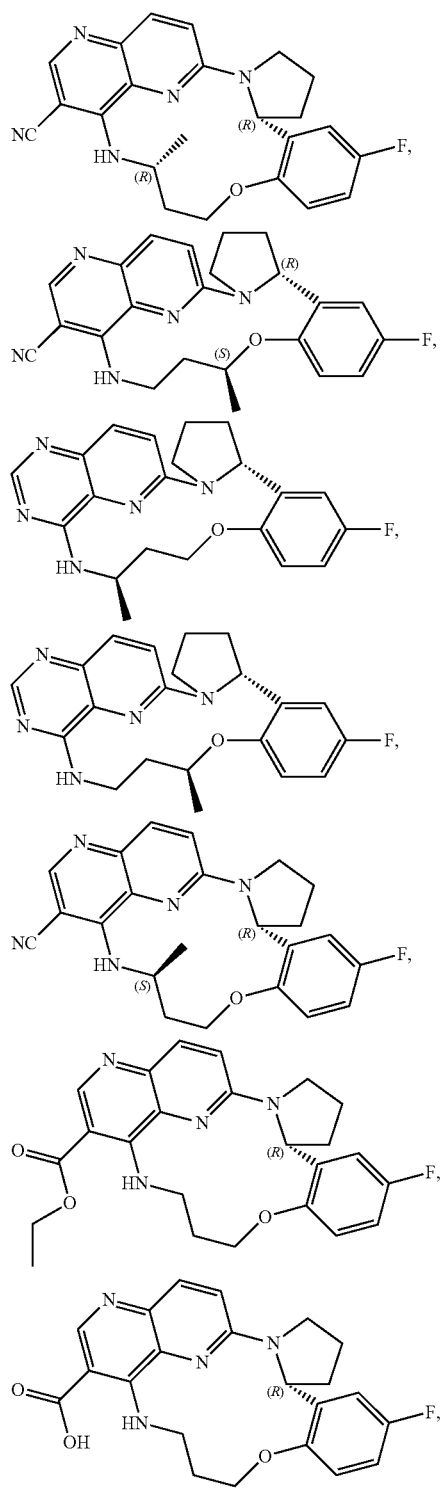
-continued
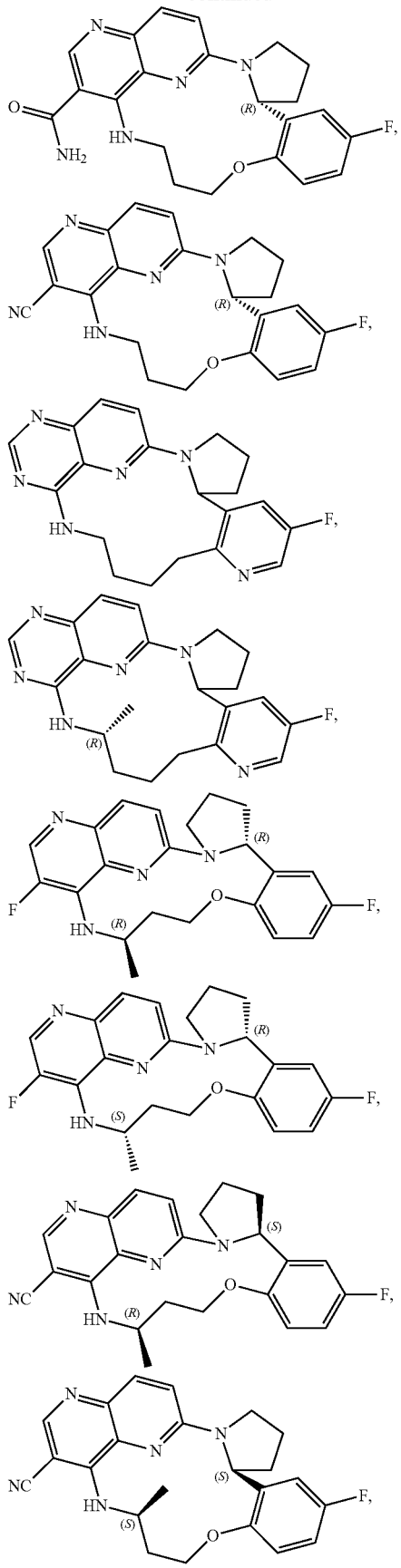

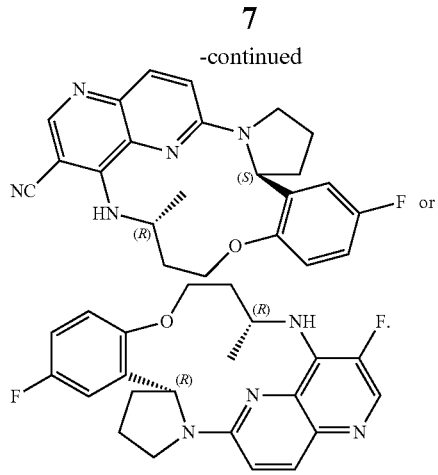

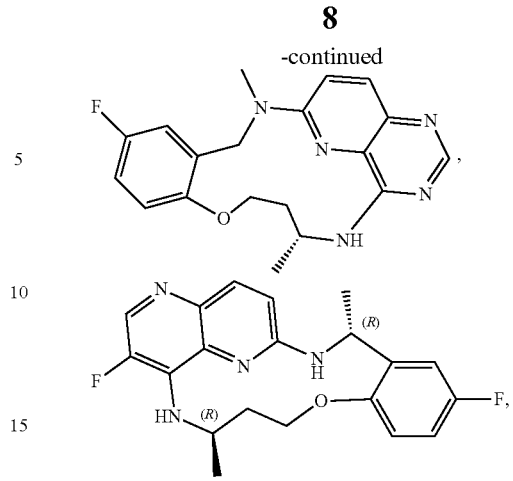

Further, the compound as shown in formula I, or a stereoisomer thereof, or a pharmaceutically acceptable salt is shown in Formula III:

Formula III

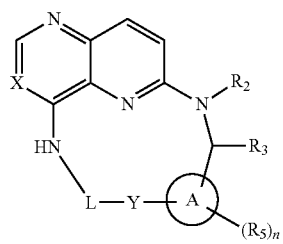

wherein
X is selected from CR$_1$ or N;
R$_1$ is selected from halogen and —CN;
ring A is selected from abenzene ring and a naphthalene ring;
n is 1, 2, 3, or 4;
R$_5$ is independently selected from hydrogen and halogen;
Y is selected from O and —NR$_a$—;
R$_a$ is selected from hydrogen and C$_{10\text{-}10}$ alkyl;
L is selected from C$_{1\text{-}10}$ alkylene; wherein the alkylene is substituted with m R$_c$; and
m is 0, 1, 2, 3, or 4.

Further, the compound as shown in formula III, or a stereoisomer thereof, or a pharmaceutically acceptable salt thereof is:

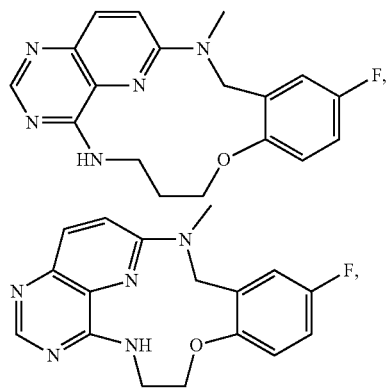

The invention also provides the use of the aforementioned compound, or a stereoisomer thereof, or a pharmaceutically acceptable salt thereof in the manufacture of a kinase inhibitor.

Further, the kinase inhibitor is a Trk kinase inhibitor.

Further, the Trk kinase inhibitor is a TrkA kinase inhibitor.

The present invention also provides the use of the aforementioned compound, or a stereoisomer thereof, or a pharmaceutically acceptable salt thereof in the manufacture of a medicament for treating a disease related to abnormal kinase activity.

Further, the disease related to abnormal kinase activity is a disease related to abnormal Trk kinase activity.

Further, the disease related to abnormal Trk kinase activity is any one or more of diseases related to neurodegenerative diseases, pain, cancer, and inflammation.

The present invention also provides the use of the aforementioned compound, or a stereoisomer thereof, or a pharmaceutically acceptable salt thereof in the manufacture of a medicament for treating neuroretirement diseases, chronic pain, acute pain, cancer, or inflammatory diseases.

Further, the disease is multiple sclerosis, Parkinson's disease, Alzheimer's disease, inflammatory pain, neuropathic pain, surgical pain, neurocytoma, melanoma, breast cancer, gastric cancer, asthma, inflammatory bowel disease or specific dermatitis.

The present invention also provides a medicament, which is a formulation, prepared from the aforementioned compound, or a stereoisomer thereof, or a pharmaceutically acceptable salt thereof, together with a pharmaceutically acceptable auxiliary material.

The diseases related to Trk activity defined in the present invention are those in which TrkA, TrkB, and TrkC play an important role in the pathogenesis of the disease.

Diseases related to Trk activity include pain, cancers or malignant tumors, inflammatory diseases or neurodegenerative diseases.

Pain includes chronic pain and acute pain, including but not limited to bone pain, visceral pain, inflammatory pain, migraine, chronic low back pain, bladder pain syndrome and neuropathy pain caused by cancers, surgery, fractures, tumor metastasis, etc.

"Cancer" or "malignant tumor" refers to any of a variety of diseases characterized by uncontrolled proliferation of cells, in which the affected cells are localized or have the ability to spread to other parts of the body through the bloodstream and lymphatic system (i.e., metastasis), and any of many characteristic structures and/or molecular characteristics. "Cancer cell" refers to a cell that has undergone multi-step tumor progression in the early, middle, or late stages. Cancers include sarcoma, breast cancer, lung cancer, brain cancer, bone cancer, liver cancer, kidney cancer, colon cancer, and prostate cancer. In some embodiments, the compound of formula I is used to treat a cancer selected from colon cancer, brain cancer, breast cancer, fibrosarcoma, and squamous cell carcinoma. In some embodiments, the cancer is selected from melanoma, breast cancer, colon cancer, lung cancer, and ovarian cancer. In some embodiments, the cancer being treated is a metastatic cancer.

Inflammatory diseases include various conditions characterized by histopathological inflammation. Examples of inflammatory diseases include acne vulgaris, asthma, celiac disease, chronic prostatitis, glomerulonephritis, inflammatory bowel disease, pelvic inflammatory disease, reperfusion injury, rheumatoid arthritis, sarcoidosis, vasculitis, airway inflammation caused by house dust mites, and interstitial cystitis. There is a significant overlap between inflammatory diseases and autoimmune diseases. Some embodiments of the invention relate to the treatment of the inflammatory disease asthma. The immune system is usually involved in inflammatory diseases, which are manifested in allergic reactions and some myopathy. Many immune system diseases cause abnormal inflammation.

Neuroretirement diseases include multiple sclerosis, Parkinson's disease and Alzheimer's disease.

The compounds and derivatives provided in the present invention can be named according to the IUPAC (International Union of Pure and Applied Chemistry) or CAS (Chemical Abstracts Service, Columbus, Ohio) naming system.

Definition of terms used in the present invention: Unless otherwise stated, the initial definition of a group or term provided herein applies to the group or term used throughout the specification; terms not specifically defined herein should be given a meaning that can be determined by those skilled in the art based on the disclosure and context.

"Substitution" refers to the replacement of hydrogen atoms in a molecule with other different atoms or molecules.

The minimum and maximum carbon atom number in a hydrocarbon group is indicated by a prefix. For example, the $C_{a-b}$ alkyl indicates any alkyl group containing "a" to "b" carbon atoms. Thus, for example, $C_{1-4}$ alkyl refers to an alkyl group containing 1 to 4 carbon atoms.

Halogen is fluorine, chlorine, bromine or iodine.

In the present invention, "heterocycle" refers to a saturated ring or a non-aromatic unsaturated ring containing at least one hetero atom; wherein the hetero atom refers to a nitrogen atom, an oxygen atom, and a sulfur atom;

In the present invention, "aromatic heterocycle" refers to an aromatic unsaturated ring containing at least one heteroatom; wherein heteroatom refers to a nitrogen atom, an oxygen atom, and a sulfur atom:

In the present invention, "alkylene" refers to a hydrocarbon group connected to two atoms respectively;

In the present invention, "alkenylene" refers to a hydrocarbon group containing at least one carbon-carbon double bond and connected to two atoms respectively;

In the present invention, "alkynylene" refers to a hydrocarbon group containing at least one carbon-carbon triple bond and connected to two atoms respectively;

In the present invention, "stereoisomer" includes enantiomers and diastereomers;

The term "pharmaceutically acceptable" means that a carrier, vehicle, diluent, excipient, and/or salt formed is usually chemically or physically compatible with other ingredients constituting a pharmaceutical dosage form, and physiologically compatible with the receptor.

The terms "salt" and "pharmaceutically acceptable salts" refer to the acidic and/or basic salts of the above compounds or their stereoisomers with inorganic and/or organic acids and bases, and also include zwitterionic salts (internal salts), and also includes quaternary ammonium salts, such as alkyl ammonium salts. These salts can be obtained directly in the final isolation and purification of the compound. They may also be obtained by appropriately mixing a certain amount (for example, equivalent) of acid or base with the above-mentioned compound, or a stereoisomer thereof. These salts may form a precipitate in the solution and be collected by filtration, or recovered after the solvent is evaporated, or prepared by freeze-drying after reaction in an aqueous medium. Salts in the present invention may be the hydrochloride, sulfate, citrate, benzenesulfonate, hydrobromide, hydrofluoride, phosphate, acetate, propionate, succinate, oxalate, malate, succinate, fumarate, maleate, tartrate or trifluoroacetate of the compound.

In certain embodiments, one or more compounds of the present invention may be used in combination with each other. Alternatively, the compound of the present invention can be used in combination with any other active agent for the preparation of a medicament or pharmaceutical composition for regulating cell function or treating diseases. If a group of compounds is used, these compounds can be administered to the subject simultaneously, separately or sequentially.

In the present invention, "M" means mol/L; "mM" means mmol/L; and "~M" means μmol/L.

In the present invention, "room temperature" means 25±5° C.

The new compound as shown in formula I disclosed in the present invention exhibits an excellent TRK inhibitory activity, has a significant inhibitory effect on TRKA-mutant cell growth, and exhibits an excellent inhibitory effect on in vivo tumor growth, thus providing a new choice for the clinical treatment of diseases associated with abnormal TRK activity.

Obviously, according to the above content of the present invention, in accordance with the ordinary technical knowledge and conventional means in the art, other various forms of modification, replacement or alteration can be made without departing from the above basic technical idea of the present invention.

The above content of the present invention will be further described in detail below through specific implementations in the form of examples. However, it should not be understood that the scope of the above subject matter of the present invention is limited to the following examples. All technologies implemented based on the above contents of the present invention belong to the scope of the present invention.

DETAILED DESCRIPTION

Figure 1:
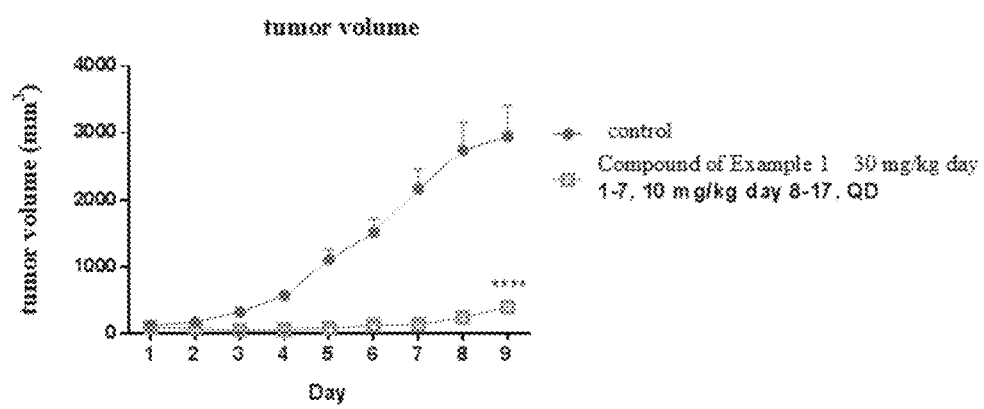
FIG. 1 shows the inhibition of the compound of Example 1 on the growth of Balb/c Nude mouse tumors (NIH-3T3ΔTRKA G595R cells).

The raw materials and equipment used in the specific embodiments of the present invention are known products, and obtained by purchasing commercially available products.

1) Raw Materials and Reagents

The raw materials used in the present invention are mainly purchased from suppliers such as J & K Scientific Ltd, Accela ChemBio Co., Ltd., Alfa Aesar, Jiangsu Aikon Biopharmaceutical R & D Co., Ltd, and TCI (Shanghai) Development Co., Ltd.

2) Main Instrument

The main instruments include rotary evaporator, ultraviolet analyzer, nuclear magnetic resonance analyzer, liquid chromatography mass spectrometer (LC-MS), high performance preparative liquid chromatography (HPLC), preparative high efficiency preparative liquid chromatography (Pre-HPLC), medium pressure preparative liquid chromatography (MPLC), etc.

Example 1. Preparation of (6R,16R)-9-fluoro-16-methyl-3-oxa-2,17,21,25-tetraazapentacyclo [16.6.2.0$^{2,6}$.0$^{7,12}$.0$^{22,26}$]hexacosane-1(25),7,9,11,18 (26),19,21,23-octane-19-nitrile

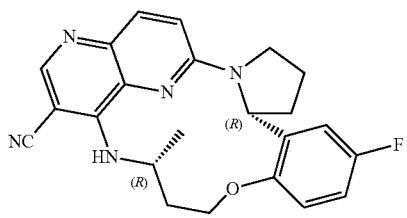

(1) Preparation of 1-bromo-2-benzyloxy-5-fluorobenzene

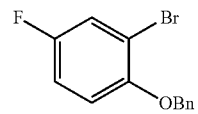

2-Bromo-4-fluorophenol (55.0 g, 288 mmol) was dissolved in methanol (300 mL), and potassium carbonate (47.0 g 346 mmol) was added, and then benzyl bromide (59.1 g, 346 mmol) was added slowly at room temperature. The mixture was stirred at 70° C. for 4 hours. The solvent was evaporated under reduced pressure, the residue was extracted with ethyl acetate and water, and the aqueous phase was extracted twice with ethyl acetate. The organic phases were combined and dried over anhydrous sodium sulfate. The solvent was evaporated under reduced pressure to obtain crude 1-bromo-2-benzyloxy-5-fluorobenzene (75.0 g, 267 mmol, 92.6% yield).

(2) Preparation of 1-(2-benzyloxy-5-fluorophenyl)-4-chlorobutyl-1-one

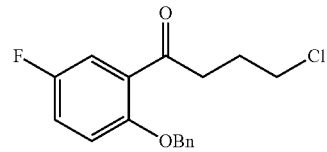 [SMILES: O=C(CCCCl)c1cc(F)ccc1OCc1ccccc1]

Under nitrogen atmosphere, magnesium bar (8.00 g, 329 mmol) and an elemental iodine particle were added to a dry three-necked bottle. A solution of 1-bromo-2-benzyloxy-5-fluorobenzene (84.0 g, 299 mmol) in anhydrous tetrahydrofuran (100 mL) was added dropwise at room temperature, with a speed roughly equivalent to the reflux speed after the reaction was initiated. After the addition, the reaction was allowed to proceed at room temperature for one hour. Then 4-chloro-N-methoxy-N-methylbutanamide (54.4 g, 329 mmol) was added on ice bath, and after the addition, the temperature was slowly raised to room temperature. After stirring at room temperature for 0.5 hours, the reaction was quenched with saturated ammonium chloride solution. The reaction mixture was extracted with ethyl acetate, and the organic phase was washed twice with saturated brine. The organic phases were combined and dried over anhydrous sodium sulfate. The solvent was evaporated under reduced pressure and the residue was purified by column chromatography (petroleum ether:ethyl acetate=10:1) to obtain 1-(2-benzyloxy-5-fluorophenyl)-4-chlorobutyl-1-one (60.0 g, 196 mmol, 65.5% yield).

MS (ESI) m/z=307 (M+1)$^+$.

(3) Preparation of (S)—N-(1-(2-benzyloxy-5-fluorophenyl)-4-chlorobutylene)-2-methylpropyl-2-sulfinamide

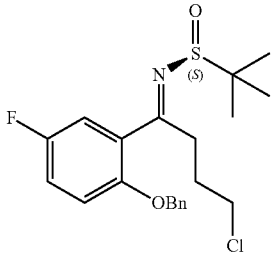

1-(2-benzyloxy-5-fluorophenyl)-4-chlorobutyl-1-one (43.4 g, 142 mmol) was dissolved in tetrahydrofuran (150 mL), and (S)-tert-butylsulfinamide (38.6 g, 318 mmol) and tetraethyl titanate (48.4 g, 212 mmol) were added at room temperature. After stirring at 70° C. for 16 hours under nitrogen atmosphere, ethyl acetate and a small amount of water were added to precipitate a large amount of solid, which was filtered with suction. The filtrate was washed twice with saturated brine and the solvent was evaporated under reduced pressure. The residue was purified by column chromatography (petroleum ether:ethyl acetate=3:1) to obtain (S)—N-(1-(2-benzyloxy-5-fluorophenyl)-4-chlorobutylene)-2-methylpropyl-2-sulfinamide (40.0 g, 97.6 mmol, 69.0% yield).

MS (ESI) m/z=410 (M+1)$^+$.

(4) Preparation of (R)-2-(2-benzyloxy-5-fluorophenyl)-1-((S)-tert-butylsulfinyl)tetrahydropyrrole

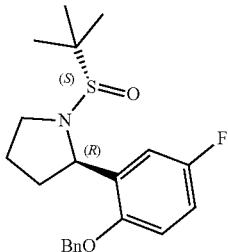

Under nitrogen atmosphere, (S)—N-(1-(2-benzyloxy-5-fluorophenyl)-4-chlorobutylene)-2-methylpropyl-2-sulfinamide (40.0 g, 97.6 mmol) was dissolved in anhydrous tetrahydrofuran (300 ml). A solution of lithium triethylborohydride in tetrahydrofuran (120 mL, 1.0 M, 120 mmol) was added dropwise at −78° C., and the reaction was allowed to proceed at −78° C. for 3 hours after the addition. The mixture was warmed to room temperature and stirred for 2 hours, and then the reaction was quenched with saturated ammonium chloride solution. The reaction mixture was extracted with ethyl acetate, and the organic phase was washed twice with saturated brine. The organic phases were combined and dried over anhydrous sodium sulfate, and the solvent was evaporated under reduced pressure. The residue was purified by column chromatography (petroleum ether: ethyl acetate=4:1) to obtain (R)-2-(2-benzyloxy-5-fluorophenyl)-1-((S)-tert-butylsulfinyl)tetrahydropyrrole (16.0 g, 42.7 mmol, 43.7% yield).

MS (ESI) m/z=376 (M+1)$^+$.

(5) Preparation of (R)-4-fluoro-2-(tetrahydropyrrol-2-yl) phenol

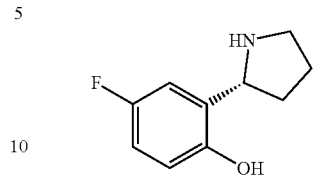

(R)-2-(2-benzyloxy-5-fluorophenyl)-1-((S)-tert-butylsulfinyl)tetrahydropyrrole (3.00 g, 8.00 mmol) was dissolved in dichloromethane (8.00 mL), then a solution of boron trichloride in dichloromethane (16.0 mL, 1.0 M, 16.0 mmol) was added dropwise at −78° C., and the reaction was allowed to proceed at −78° C. for 0.5 hour after the addition. Methanol was added to quench the reaction and the solvent was evaporated under reduced pressure. The residue was purified by MPLC to obtain (R)-4-fluoro-2-(tetrahydropyrrol-2-yl) phenol (1.27 g, 7.00 mmol, 87.5% yield).

MS (EST) m/z=182 (M+1)$^+$.

(6) Preparation of benzyl (R)-2-(5-fluoro-2-hydroxyphenyl)tetrahydropyrrole-1-carboxylate

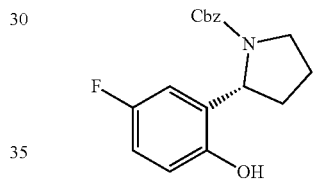

(R)-4-fluoro-2-(tetrahydropyrrol-2-yl)phenol (1.27 g, 7.00 mmol) was dissolved in dichloromethane (15.0 mL), then triethylamine (2.12 g, 21.0 mmol) and benzyloxycarbonyl succinimide (1.92 g, 7.70 mmol) were added at room temperature, and stirred at room temperature for 2 hours. Methanol was added to quench the reaction and the solvent was evaporated under reduced pressure. The residue was purified by column chromatography (petroleum ether:ethyl acetate=1:1) to obtain benzyl (R)-2-(5-fluoro-2-hydroxyphenyl) tetrahydropyrrole-1-carboxylate (1.93 g, 6.10 mmol, 87.1% yield).

MS (ESI) m/z=316 (M+1)$^+$.

(7) Preparation of benzyl (R)-2-(2-((R)-3-((tert-butoxycarbonyl)amino)butoxy)-5-fluorophenyl) tetrahydropyrrole-1-carboxylate

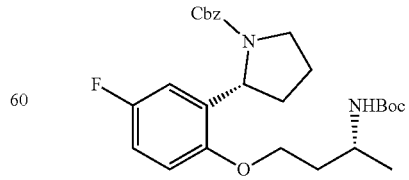

Benzyl (R)-2-(5-fluoro-2-hydroxyphenyl)tetrahydropyrrole-1-carboxylate (14.2 g, 45.1 mmol) was dissolved in N,N-dimethylformamide (100 mL), then cesium carbonate (44.0 g, 135 mmol) and (R)-3-((tert-butoxycarbonyl)amino) butyl methanesulfonate (18.1 g, 67.6 mmol) were added, and stirred at 80° C. for 2 hours. The solvent was evaporated under reduced pressure, the residue was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=1:1) to obtain benzyl (R)-2-(2-((R)-3-((tert-butoxycarbonyl)amino)butoxy)-5-fluorophenyl)tetrahydropyrrole-1-carboxylate (18.5 g, 38.1 mmol, 84.4% yield).

MS (ESI) m/z=487 (M+1)+.

(8) Preparation of benzyl (R)-2-(2-((R)-3-aminobutoxy)-5-fluorophenyl) tetrahydropyrrole-1-carboxylate

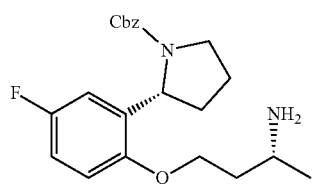 [SMILES: C[C@@H](N)CCOc1ccc(F)cc1[C@H]1CCCN1C(=O)OCc1ccccc1]

Benzyl (R)-2-(2-((R)-3-((tert-butoxycarbonyl)amino)butoxy)-5-fluorophenyl) tetrahydropyrrole-1-carboxylate (18.5 g, 38.1 mmol) was dissolved in dichloromethane (60.0 mL), and trifluoroacetic acid (20.0 ml) was added at room temperature. The mixture was stirred at room temperature for 1 hour. The solvent was evaporated under reduced pressure to obtain crude benzyl (R)-2-(2-(((R)-3-aminobutoxy)-5-fluorophenyl)tetrahydropyrrole-1-carboxylate (14.7 g, 38.1 mmol, 100% yield).

MS (ESI) m/z=387 (M+1)+.

(9) Preparation of ethyl 4-(((R)-4-(2-((R)-1-(benzyloxycarbonyl)tetrahydropyrrol-2-yl)-4-fluorophenoxy)butyl-2-yl)amino)-6-chloro-1,5-naphthyridine-3-carboxylate

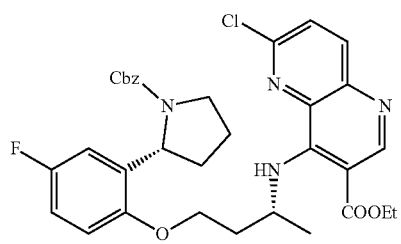 [SMILES: CCOC(=O)c1cnc2ccc(Cl)nc2c1N[C@H](C)CCOc1ccc(F)cc1[C@H]1CCCN1C(=O)OCc1ccccc1]

Benzyl (R)-2-(2-((R)-3-aminobutoxy)-5-fluorophenyl) tetrahydropyrrole-1-carboxylate (14.7 g, 38.1 mmol) was dissolved in dichloromethane (120 mL) and tert-butanol (40.0 mL), then potassium carbonate (21.0 g, 152 mmol) and ethyl 4,6-dichloro-1,5-naphthyridine-3-carboxylate (10.3 g, 38.1 mmol) were added and stirred at 35° C. for 16 hours. The solvent was evaporated under reduced pressure, the residue was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=1.5:1) to obtain ethyl 4-(((R)-4-(2-((R)-1-(benzyloxycarbonyl)tetrahydropyrrol-2-yl)-4-fluorophenoxy) butyl-2-yl)amino)-6-chloro-1,5-naphthyridine-3-carboxylate (19.5 g, 31.5 mmol, 82.7% yield).

MS (ESI) m/z=621 (M+1)+.

(10) Preparation of ethyl 6-chloro-4-(((R)-4-(4-fluoro-2-((R)-tetrahydropyrrol-2-yl)phenoxy) butyl-2-yl)amino) 1,5-naphthyridine-3-carboxylate

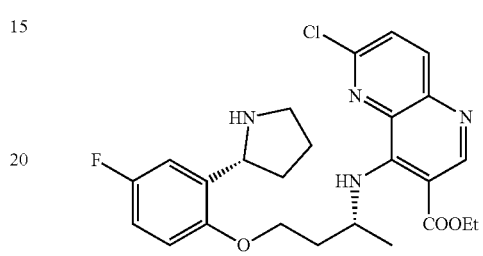

Ethyl 4-(((R)-4-(2-((R)-1-(benzyloxycarbonyl)tetrahydropyrrol-2-yl)-4-fluorophenoxy) butyl-2-yl)amino)-6-chloro-1,5-naphthyridine-3-carboxylate (19.5 g, 31.5 mmol) was dissolved in acetic acid (60.0 mL), and a solution of hydrobromic acid in acetic acid (30.0 mL, 40% w/w) was added at 0° C. After addition, the mixture was stirred at room temperature for 1.5 hours. The solvent was evaporated under reduced pressure to obtain ethyl 6-chloro-4-(((R)-4-(4-fluoro-2-((R)-tetrahydropyrrol-2-yl)phenoxy)butyl-2-yl) amino) 1,5-naphthyridine-3-carboxylate (15.0 g, 30.9 mmol, 98.0% yield).

MS (ESI) m/z=487 (M+1)+.

(11) Preparation of ethyl (6R,16R)-9-fluoro-16-methyl-13-oxa-2,17,21,25-tetraazapentacyclo [16.6.2.0²,⁶.0⁷,¹².0²²,¹⁶]hexacosane-1(25),7,9,11,18 (26),19,21,23-octane-19-carboxylate

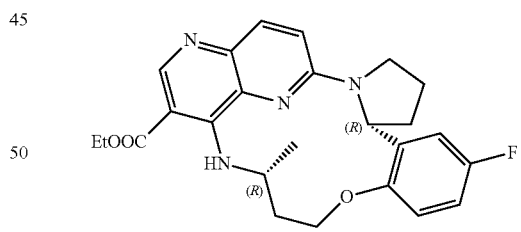

Ethyl 6-chloro-4-(((R)-4-(4-fluoro-2-((R)-tetrahydropyrrol-2-yl)phenoxy)butyl-2-yl) amino)1,5-naphthyridine-3-carboxylate (15.0 g, 30.9 mmol) was dissolved in toluene (360 mL) and tert-butanol (120 mL), and tris(dibenzylideneacetone)dipalladium (2.83 g, 3.1 mmol), 2-biscyclohexylphosphine-2',6'-dimethoxybiphenyl (2.54 g, 6.20 mmol) and cesium carbonate (40.3 g, 124 mmol) were added. Under nitrogen atmosphere, the mixture was stirred at 100° C. for 16 hours. The solvent was evaporated under reduced pressure, the residue was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (dichloromethane:methanol=20:1) to obtain ethyl (6R,16R)-9-fluoro-16-methyl-13-oxa-2,17,21,25-tetraazapentacyclo[16.6.2.0$^{2,6}$.0$^{7,12}$.0$^{22,26}$]hexacosane-1(25),7,9,11,18(26),19,21,23-octane-19-carboxylate (7.51 g, 16.7 mmol, 54.0% yield).

MS (ESI) m/z=451 (M+1)$^+$.

(12) Preparation of (6R,16R)-9-fluoro-16-methyl-13-oxa-2,17,21,25-tetraazapentacyclo[16.6.2.0$^{2,6}$.0$^{7,12}$.0$^{22,26}$]hexacosane-1(25),7,9,11,18(26),19,21,23-octane-19-carboxylic acid

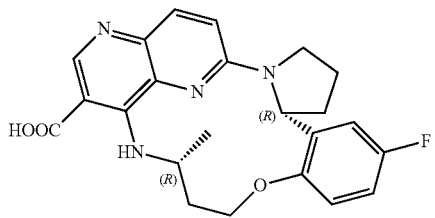

Ethyl (6R,16R)-9-fluoro-16-methyl-13-oxa-2,17,21,25-tetraazapentacyclo [16.6.2.0$^{2,6}$.0$^{7,12}$.0$^{22,26}$]hexacosane-1(25),7,9,11,18(26),19,21,23-octane-19-carboxylate (7.51 g, 16.7 mmol) was dissolved in ethanol (25.0 mL) and tetrahydrofuran (25.0 mL), and aqueous solution (25.0 mL) of sodium hydroxide (3.34 g, 83.5 mmol) was added. The mixture was stirred at 50° C. for 3 hours, and then adjusted to pH=3-4 with 1M HCl solution on ice bath. The mixture was extracted with dichloromethane and water, and the aqueous phase was extracted twice with dichloromethane. The organic phases were combined and dried over anhydrous sodium sulfate. The solvent was evaporated under reduced pressure to obtain cure (6R,16R)-9-fluoro-16-methyl-3-oxa-2,17,21,25-tetraazapentacyclo[16.6.2.0$^{2,6}$.0$^{7,12}$.0$^{22,26}$]hexacosane-1(25),7,9,11,18(26),19,21,23-octane-19-carboxylic acid (5.86 g, 13.9 mmol, 83.2% yield).

MS (ESI) m/z=423 (M+1)$^+$.

(13) Preparation of (6R,16R)-9-fluoro-16-methyl-13-oxa-2,17,21,25-tetraazapentacyclo[16.6.2.0$^{2,6}$.0$^{7,12}$.0$^{22,26}$] hexacosane-1(25),7,9,11,18(26),19,21,23-octane-19-carboxamide

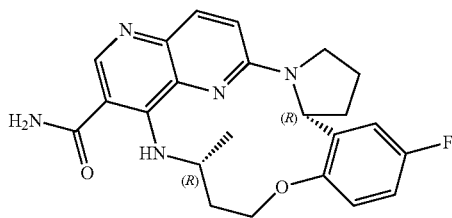

(6R,16R)-9-Fluoro-16-methyl-13-oxa-2,17,21,25-tetraazapentacyclo[16.6.2.0$^{2,6}$.0$^{7,12}$.0$^{22,26}$] hexacosane-1(25), 7,9,11,18(26),19,21,23-octane-9-carboxylic acid (5.86 g, 13.9 mmol) was dissolved in N,N-dimethylformamide (25.0 mL) and dichloromethane (25.0 mL), and N,N-diisopropylethylamine (7.17 g, 55.6 mmol), benzotriazole-N,N,N',N'-tetramethylurea hexafluorophosphate (6.85 g, 18.1 mmol) and ammonium chloride (2.23 g, 41.7 mmol) were added. After stirring at room temperature for 2 hours, the mixture was extracted with dichloromethane and water and the aqueous phase was extracted twice with dichloromethane. The organic phases were combined and dried over anhydrous sodium sulfate. The solvent was evaporated under reduced pressure and the residue was purified by column chromatography (dichloromethane:methanol=10:1) to obtain (6R,16R)-9-fluoro-16-methyl-13-oxa-2,17,21,25-tetraazapentacyclo[16.6.2.0$^{2,6}$.0$^{7,12}$.0$^{22,26}$]hexacosane-1(25),7,9,11,18(26),19,21,23-octane-19-carboxamide (3.09 g, 7.34 mmol, yield 52.8%).

MS (ESI) m/z=422 (M+1)$^+$.

(14) Preparation of (6R,16R)-9-fluoro-16-methyl-13-oxa-2,17,21,25-tetraazapentacyclo[16.6.2.0$^{2,6}$.0$^{7,12}$.0$^{22,26}$]hexacosane-1(25),7,9,11,18(26),19,21,23-octane-19-nitrile

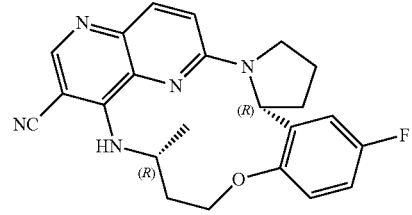

(6R,16R)-9-Fluoro-16-methyl-13-oxa-2,17,21,25-tetraazapentacyclo [16.6.2.0$^{2,6}$.0$^{7,12}$.0$^{22,26}$]hexacosane-1(25), 7,9,11,18(26),19,21,23-octane-19-carboxamide (3.09 g, 7.34 mmol) was dissolved in dichloromethane (25.0 mL), then triethylamine (2.22 g, 22.0 mmol) was added, and then trifluoroacetic anhydride (2.31 g, 11.0 mmol) was added dropwise. After stirring at room temperature for 2 hours, the mixture was extracted with dichloromethane and water and the aqueous phase was extracted twice with dichloromethane. The organic phases were combined and dried over anhydrous sodium sulfate. The solvent was evaporated under reduced pressure and the residue was purified by preparative Pre-HPLC to obtain (6R,16R)-9-fluoro-16-methyl-13-oxa-2,17,21,25-tetraazapentacyclo[16.6.2.0$^{2,6}$.0$^{7,12}$.0$^{22,26}$]hexacosane-1(25),7,9,11,18(26),19,21,23-octane-9-nitrile (1.85 g, 4.59 mmol, 62.5% yield).

MS (EST) m/z=404 (M+1)$^+$.

$^1$HNMR (400 MHz, MeOD): δ=9.37 (d, J=7.2, 1H), 8.23 (s, 1H), 7.93 (d, J=9.2, 1H), 6.98-6.92 (m, 2H), 6.86-6.78 (m, 2H), 5.79-5.76 (m, 1H), 4.75-4.61 (m, 3H), 3.97-3.91 (m, 1H), 3.71-3.66 (m, 1H), 2.61-2.39 (m, 3H), 2.18-1.96 (m, 3H), 1.58 (d, J=6.4, 3H).

Example 2. Preparation of (6R,14S)-9-fluoro-14-methyl-3-oxa-2,17,21,25-tetraazapentacyclo [16.6.2.0²,⁶.0⁷,¹².0²²,²⁶]hexacosane-1(25),7,9,11,18(26),19,21,23-octane-19-nitrile

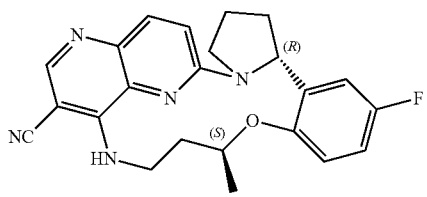

(1) Preparation of (R)-2,2,2-trifluoro-1-(2-(5-fluoro-2-hydroxyphenyl)tetrahydropyrrol-1-yl) ethanone

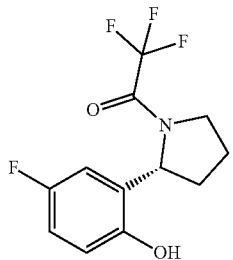 [SMILES: O=C(N1CCC[C@@H]1c1cc(F)ccc1O)C(F)(F)F]

(R)-4-fluoro-2-(tetrahydropyrrol-2-yl)phenol (540 mg, 3.00 mmol) was dissolved in trifluoroacetic anhydride (2.00 mL), and the mixture was stirred at 0° C. for 0.5 hour. The solvent was evaporated under reduced pressure and the residue was purified by column chromatography (petroleum ether:ethyl acetate=3:1) to obtain (R)-2,2,2-trifluoro-1-(2-(5-fluoro-2-hydroxyphenyl)tetrahydropyrrol-1-yl)ethanone (420 mg, 1.50 mmol, 50.5% yield).
MS (ESI) m/z=278 (M+1)⁺.

(2) Preparation of tert-butyl 2,4-dimethoxybenzyl ((S)-3-(4-fluoro-2-((R)-1-(2,2,2-trifluoroacetyl)tetrahydropyrrol-2-yl)phenoxy)butylcarboxamide

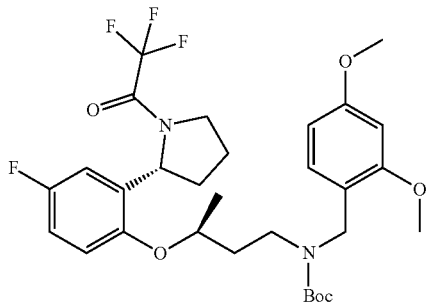 [SMILES: COc1ccc(CN(CC[C@H](C)Oc2ccc(F)cc2[C@H]2CCCN2C(=O)C(F)(F)F)C(=O)OC(C)(C)C)c(OC)c1]

(R)-2,2,2-trifluoro-1-(2-(5-fluoro-2-hydroxyphenyl)tetrahydropyrrol-1-yl)ethanone (420 mg, 1.50 mmol), (S)-tert-butyl 2,4-dimethoxybenzyl(3-hydroxybutyl)carboxamide (770 mg, 2.25 mmol) and triphenylphosphine (790 mg, 3.00 mmol) were dissolved in toluene (5.00 mL) and dichloromethane (5.00 mL), then diisopropyl azodicarboxylate (610 mg, 3.00 mmol) was added dropwise at 0° C. under nitrogen atmosphere. The mixture was stirred at 0° C. for 2.0 hours. The solvent was evaporated under reduced pressure and the residue was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=5:1) to obtain tert-butyl 2,4-dimethoxybenzyl((S)-3-(4-fluoro-2-((R)-1-(2,2,2-trifluoroacetyl) tetrahydropyrrol-2-yl)phenoxy)butyl)carboxamide (190 mg, 320 μmol, 21.1% yield).
MS (ESI) m/z=599 (M+1)⁺.

(3) Preparation of 1-((R)-2-(2-(((S)-4-aminobutyl-2-yl)oxy)-5-fluorobenzene) tetrahydropyrrol-1-yl) 2,2,2-trifluoroethanone

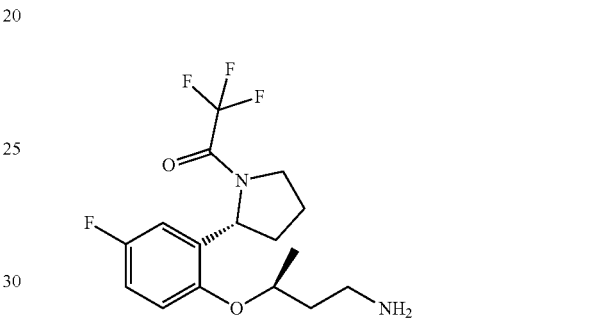

Tert-butyl 2,4-dimethoxybenzyl((S)-3-(4-fluoro-2-((R)-1-(2,2,2-trifluoroacetyl) tetrahydropyrrol-2-yl)phenoxy) butyl)carboxamide (190 mg, 320 μmol) was dissolved in dichloromethane (4.00 mL), and trifluoroacetic acid (2.00 mL) was added. The mixture was stirred at 50° C. for 3.0 hours. The solvent was evaporated under reduced pressure to obtain crude 1-((R)-2-(2-(((S)-4-aminobutyl-2-yl)oxy)-5-fluorobenzene)tetrahydropyrrol-1-yl)2,2,2-trifluoroethanone (110 mg, 320 μmol, 100% yield).
MS (ESI) m/z=349 (M+1)⁺.

(4) Preparation of ethyl 6-chloro-4-(((S)-3-(4-fluoro-2-((R)-1-(2,2,2-trifluoroacetyl) tetrahydropyrrol-2-yl) phenoxy)butyl) amino)-1,5-naphthyridine-3-carboxylate

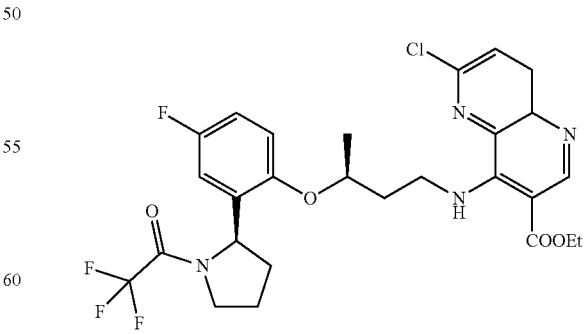

1-((R)-2-(2-(((S)-4-aminobutyl-2-yl)oxy)-5-fluorobenzene)tetrahydropyrrol-1-yl)2,2,2-trifluoroethanone (110 mg, 320 μmol) was dissolved in dichloromethane (3.00 mL) and tert-butanol (1.00 mL), then potassium carbonate (220 mg, 1.60 mmol) and ethyl 4,6-dichloro-1,5-naphthyridine-3-carboxylate (130 mg, 480 μmol) were added, and the mixture was stirred at 35° C. for 16 hours. The solvent was evaporated under reduced pressure and the residue was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=2:1) to obtain ethyl 6-chloro-4-(((S)-3-(4-fluoro-2-((R)-1-(2,2,2-trifluoroacetyl)tetrahydropyrrol-2-yl)phenoxy)butyl) amino)-1,5-naphthyridine-3-carboxylate (150 mg, 260 μmol, 80.5% yield).

MS (ESI) m/z=583 (M+1)⁺.

(5) Preparation of 6-chloro-4-(((S)-3-(4-fluoro-2-(R)-1-tetrahydropyrrol-2-yl)phenoxy)butyl) amino)-1,5-naphthalene-3-carboxylic acid

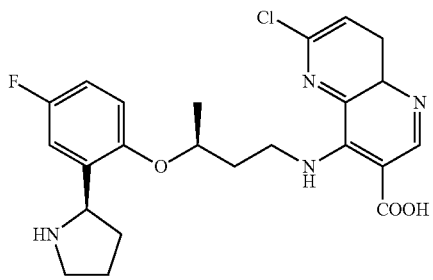 [SMILES: C[C@@H](CCNC1=C(C(=O)O)C=NC2CC=C(Cl)N=C12)Oc1ccc(F)cc1[C@H]1CCCN1]

Ethyl 6-chloro-4-(((S)-3-(4-fluoro-2-((R)-1-(2,2,2-trifluoroacetyl)tetrahydropyrrol-2-yl) phenoxy)butyl)amino)-1,5-naphthyridine-3-carboxylate (150 mg, 260 μmol) was dissolved in methanol (5.00 mL), then potassium carbonate (220 mg, 1.56 mmol) was added, and the mixture was stirred at 60° C. for 16 hours. The solvent was evaporated under reduced pressure and the residue was extracted with dichloromethane and water, and the aqueous phase was extracted twice with dichloromethane. The organic phases were combined and dried over anhydrous sodium sulfate. The solvent was evaporated under reduced pressure to crude 6-chloro-4-(((S)-3-(4-fluoro-2-((R)-1-tetrahydropyrrol-2-yl)phenoxy)butyl)amino)-1,5-naphthalene-3-carboxylic acid (110 mg, 250 μmol, 95.0% yield).

MS (ESI) m/z=459 (M+1)⁺.

(6) Preparation of (6R,14S)-9-fluoro-14-methyl-13-oxa-2,17,21,25-tetraazapentacyclo[16.6.2.0²,⁶.0⁷,¹².0²²,²⁶]hexacosane-1(25),7,9,11,18(26),19,21,23-octane-19-carboxylic acid

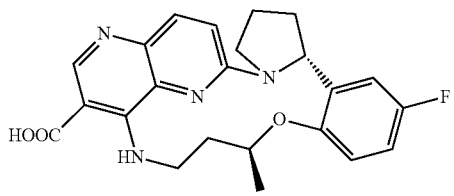 [SMILES: C[C@H]1CCNc2c(C(=O)O)cnc3ccc(nc23)N2CCC[C@@H]2c2cc(F)ccc2O1]

6-chloro-4-(((S)-3-(4-fluoro-2-((R)-1-tetrahydropyrrol-2-yl)phenoxy)butyl)amino)-1,5-naphthalene-3-carboxylic acid (110 mg, 250 μmol) was dissolved in toluene (3.00 mL) and tert-butanol (1.00 mL), then tris(dibenzylideneacetone)dipalladium (23.0 mg, 25.0 μmol), 2-bicyclohexylphosphine-2',6'-dimethoxybiphenyl (20.0 mg, 50 μmol) and cesium carbonate (407 mg, 1.25 mmol) were added. Under nitrogen atmosphere, the mixture was stirred at 100° C. for 16 hours. The solvent was evaporated under reduced pressure and the residue was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (dichloromethane:methanol=10:1) to obtain (6R,14S)-9-fluoro-14-methyl-13-oxa-2,17,21,25-tetraazapentacyclo[16.6.2.0²,⁶.0⁷,¹².0²²,²⁶]hexacosane-1(25),7,9,11,18(26),19,21,23-octane-9-carboxylic acid (53.0 mg, 130 μmol, 52.0% yield).

MS (ESI) m/z=423 (M+1)⁺.

(7) Preparation of (6R,14S)-9-fluoro-14-methyl-13-oxa-2,17,21,25-tetraazapentacyclo[16.6.2.0²,⁶.0⁷,¹².0²²,²⁶]hexacosane-1(25),7,9,11,18(26),19,21,23-octane-19-carboxamide

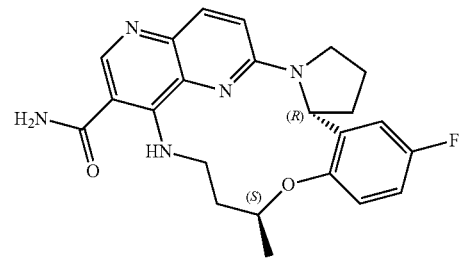

(6R,14S)-9-fluoro-14-methyl-13-oxa-2,17,21,25-tetraazapentacyclo [16.6.2.0²,⁶.0⁷,¹².0²²,²⁶]hexacosane-1(25),7,9,11,18(26),19,21,23-octane-9-carboxylic acid (53.0 mg, 130 μmol) was dissolved in N,N-dimethylformamide (1.00 mL) and dichloromethane (1.00 mL), then N,N-diisopropylethylamine (84.0 mg, 650 μmol), benzotriazole-N,N,N',N'-tetramethylurea hexafluorophosphate (74.0 mg, 200 μmol) and ammonium chloride (21.0 mg, 390 μmol) were added. After stirring at room temperature for 2 hours, the mixture was extracted with dichloromethane and water, and the aqueous phase was extracted twice with dichloromethane. The organic phases were combined and dried over anhydrous sodium sulfate. The solvent was evaporated under reduced pressure and the residue was purified by column chromatography (dichloromethane:methanol=10:1) to obtain (6R,14S)-9-fluoro-14-methyl-3-oxa-2,17,21,25-tetraazapentacyclo[16.6.2.0²,⁶.0⁷,¹².0²²,²⁶]hexacosane-1(25),7,9,11,18(26),19,21,23-octane-19-carboxamide (20.0 mg, 48 μmol, 36.5% yield).

MS (ESI) m/z=422 (M+1)⁺.

(8) Preparation of (6R,14S)-9-fluoro-14-methyl-13-oxa-2,17,21,25-tetraazapentacyclo[16.6.2.0²,⁶.0⁷,¹².0²²,²⁶]hexacosane-1(25),7,9,11,18(26),19,21,23-octane-19-nitrile

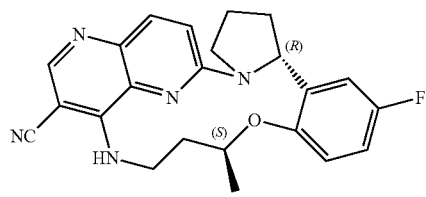

(6R,14S)-9-fluoro-14-methyl-13-oxa-2,17,21,25-tetraazapentacyclo[16.6.2.0²,⁶.0⁷,¹².0²²,²⁶] hexacosane-1(25),7,9,11,18(26),19,21,23-octane-19-carboxamide (20.0 mg, 48 μmol) was dissolved in dichloromethane (3.00 mL), then triethylamine (30.0 mg, 285 μmol) was added, and trifluoroacetic anhydride (30.0 mg, 145 μmol) was added dropwise. The mixture was stirred at room temperature for 2 hours. The solvent was evaporated under reduced pressure and the residue was purified by preparative Pre-HPLC to obtain (6R,14S)-9-fluoro-14-methyl-13-oxa-2,17,21,25-tetraazapentacyclo [16.6.2.0²,⁶.0⁷,¹².0²²,²⁶]hexacosane-1(25),7,9,11,18(26),19,21,23-octane-19-nitrile (1.50 mg, 3.70 μmol, 7.7% yield).

MS (ESI) m/z=404 (M+1)⁺.

Example 3. Preparation of 6-fluoro-2-methyl-10-oxa-2,14,16,18,22-pentaazatetracyclo[13.6.2.0⁴,⁹.0¹⁹,²³] tricosane-1(22),4,6,8,15(23),16,18,20-octane

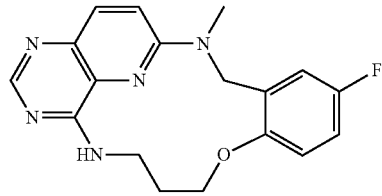 [SMILES: CN1Cc2cc(F)ccc2OCCCNc2ncnc3ccc1nc23]

(1) Preparation of 5-fluoro-2-methoxy-N-methylbenzamide

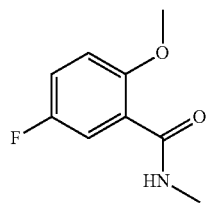

5-fluoro-2-methoxy-benzoic acid (12.0 g, 70.5 mmol) was dissolved in dichloromethane (200 v mL), then benzotriazole-N,N,N',N'-tetramethyluronium hexafluorophosphate (32.2 g, 84.6 mmol), methylamine hydrochloride (3.29 g, 106 mmol) and N,N-diisopropylethylamine (45.5 g, 353 mmol) were added. After stirring for 1 hour, the mixture was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=4:1) to obtain 5-fluoro-2-methoxy-N-methylbenzamide (12.0 g, 65.5 mmol, 92.9% yield).

MS (ESI) m/z=184 (M+1)⁺.

(2) Preparation of 1-(5-fluoro-2-methoxyphenyl)-N-methylmethylamine

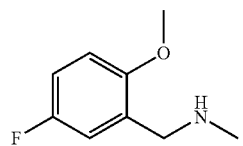

Lithium tetrahydroaluminum (5.80 g, 153 mmol) was dissolved in tetrahydrofuran (200 mL), then 5-fluoro-2-methoxy-N-methylbenzamide (12.0 g, 65.5 mmol) was added. After stirring at 50° C. for 10 hours, the reaction was quenched with crystalline sodium sulfate, stirred in methanol, and filtered, and the filtrate was spin-dried to obtain 1-(5-fluoro-2-methoxyphenyl)-N-methylmethylamine (10.2 g, 60.9 mmol, 92.9% yield).

MS (ESI) m/z=170 (M+1)⁺.

(3) Preparation of benzyl 5-fluoro-2-methoxybenzyl (methyl) carbamate

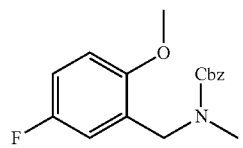 [SMILES: COc1ccc(F)cc1CN(C)C(=O)OCc1ccccc1]

1-(5-fluoro-2-methoxyphenyl)-N-methylmethylamine (12.0 g, 65.5 mmol) was dissolved in tetrahydrofuran (100 mL), and then triethylamine (17.9 g, 177 mmol) and benzyloxycarbonyl succinimide (17.7 g, 70.9 mmol) were added. After stirring for 1 hour, the mixture was extracted with ethyl acetate and water, the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=10:1) to obtain benzyl 5-fluoro-2-methoxybenzyl (methyl) carbamate (8.00 g, 26.4 mmol, yield 44.6%).

MS (ESI) m/z=304 (M+1)+.

(4) Preparation of 5-fluoro-2-((methylamino)methyl) phenol

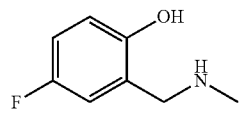

Benzyl 5-fluoro-2-methoxybenzyl(methyl)carbamate (8.00 g, 26.4 mmol) was dissolved in dichloromethane (80.0 mL), and boron tribromide (1 M, 41.5 mL) was added. After stirring on ice bath for 2 hours, the reaction was quenched with methanol. The mixture was extracted with ethyl acetate and water, and the aqueous phase was extracted twice with ethyl acetate. The organic phases were combined and dried over anhydrous sodium sulfate. The solvent was evaporated under reduced pressure and the residue was stirred in petroleum ether. The supernatant was discarded, to obtain 5-fluoro-2-((methylamino)methyl)phenol (6.00 g, 23.1 mmol, purity 60%, yield 88%).

MS (ESI) m/z=156 (M+1)$^+$.

(5) Preparation of benzyl 5-fluoro-2-hydroxybenzyl(methyl)carbamate

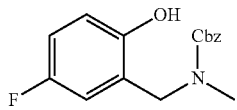

5-fluoro-2-((methylamino)methyl)phenol (6.00 g, 23.1 mmol, purity 60%) was dissolved in tetrahydrofuran (50.0 mL), and triethylamine (11.6 g, 115 mmol) and benzyloxycarbonyl succinimide (14.3 g, 57.6 mmol) were added. After stirring for 1 hour, the mixture was extracted with ethyl acetate and water, and then the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=5:1) to obtain benzyl 5-fluoro-2-hydroxybenzyl (methyl)carbamate (5.50 g, 18.9 mmol, 81.7% yield).

MS (ESI) m/z=290 (M+1)$^+$.

(6) Preparation of 3-((tert-butoxycarbonyl) amino) propyl-methanesulfonate

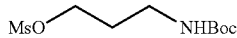

3-((tert-butoxycarbonyl)amino)propanol (800 mg, 4.57 mmol) was dissolved in methylene chloride (20.0 mL), and triethylamine (1.39 g, 13.7 mmol, 1.91 mL) and methanesulfonyl chloride (784 mg, 6.85 mmol) were added. After stirring on ice bath for 1 hour, the mixture was extracted with ethyl acetate and water, and then the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=7:1) to obtain 3-((tert-butoxycarbonyl) amino) propyl-methanesulfonate (1.00 g, 3.95 mmol, 86.5% yield).

MS (ESI) m/z=254 (M+1)$^+$ and 198 (M+1-56)$^+$.

(7) Preparation of benzyl-2-(3-((tert-butoxycarbonyl)amino)propoxy)-5-fluorophenyl(methyl) carbamate

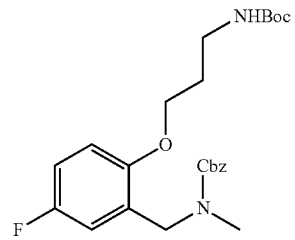 [SMILES: CN(Cc1cc(F)ccc1OCCCNC(=O)OC(C)(C)C)C(=O)OCc1ccccc1]

Benzyl 5-fluoro-2-hydroxyphenyl(methyl)carbamate (600 mg, 2.07 mmol) was dissolved in N,N-dimethylformamide (10.0 mL), and cesium carbonate (2.02 g, 6.22 mmol) and 3-((tert-butoxycarbonyl)amino)propyl-methanesulfonate (630 mg, 2.49 mmol) were added. After stirring at 70° C. for 1 hour, the mixture was extracted with ethyl acetate and water, and then the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=3:1) to obtain benzyl-2-(3-((tert-butoxycarbonyl) amino)propoxy)-5-fluorophenyl(methyl)carbamate (500 mg, 1.12 mmol, yield 54.0%).

MS (ESI) m/z=447 (M+1)$^+$.

(8) Preparation of phenyl 2-(3-aminopropoxy)-5-fluorophenyl(methyl)carbamate

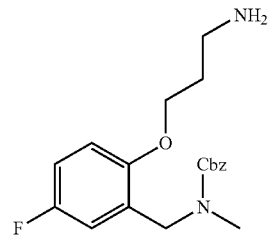 [SMILES: CN(Cc1cc(F)ccc1OCCCN)C(=O)OCc1ccccc1]

Benzyl 2-(3-((tert-butoxycarbonyl)amino)propoxy)-5-fluorophenyl(methyl)carbamate (400 mg, 900 μmol) was dissolved in dioxane hydrochloride (10.0 ml). After stirring the reaction solution for one hour, the organic solvent was removed from the reaction solution using a rotary evaporator to obtain phenyl 2-(3-aminopropoxy)-5-fluorophenyl (methyl)carbamate (250 mg, 720 μmol, yield 80.6%).

MS (ESI) m/z=347 (M+1)$^+$.

(9) Preparation of phenyl 2-(3-((6-chloropyrido[3,2-D]pyrimidin-4-yl)amino)propoxy)-5-fluorochlorobenzene(methyl)carbamate

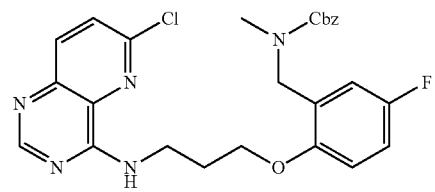 [SMILES: CN(Cc1cc(F)ccc1OCCCNc1ncnc2ccc(Cl)nc12)C(=O)OCc1ccccc1]

Phenyl 2-(3-aminopropoxy)-5-fluorophenyl(methyl)carbamate (80.0 mg, 231 μmol) was dissolved in N,N-dimethylformamide (5.00 mL) and Cesium carbonate (225 mg, 693 μmol) and 4,6-dichloropyrido[3,2-d]pyrimidine (50.8 mg, 254 μmol) were added. After stirring at 70° C. for 1 hour, the mixture was extracted with ethyl acetate and water, and then the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=1:1) to obtain phenyl 2-(3-((tert-butoxycarbonyl)amino)propoxy)-5-fluorophenyl(methyl)carbamate (70.0 mg, 98.1 μmol, 60% yield).

MS (ESI) m/z=510 (M+1)$^+$.

(10) Preparation of 6-chloro-N-(3-(5-fluoro-2-((methylamino)methyl)phenoxy)propyl)pyrido [3,2-D]pyrimidin-4-amine

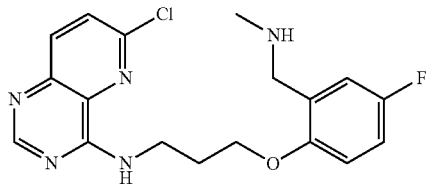 [SMILES: CNCc1cc(F)ccc1OCCCNc1ncnc2ccc(Cl)nc12]

Phenyl 2-(3-((tert-butoxycarbonyl)amino)propoxy)-5-fluorophenyl(methyl)carbamate (70.0 mg, 98.1 μmol) was dissolved in acetic acid (2.00 mL), solution of hydrobromic acid in acetic acid (1.00 ml, 33%) was added, and the reaction solution was stirred for one hour. The organic solvent was removed from the reaction solution using a rotary evaporator to obtain 6-chloro-N-(3-(5-fluoro-2-((methylamino)methyl)phenoxy)propyl)pyrido [3,2-D]pyrimidin-4-amine (40.0 mg, 106 μmol, 77.5% yield).

MS (ESI) m/z=376 (M+1)$^+$.

(11) Preparation of 6-fluoro-2-methyl-10-oxa-2,14,16,18,22-pentaazatetracyclo [13.6.2.0$^{4,9}$.0$^{19,23}$]tricosane-1(22),4,6,8,15(23),16,18,20-octane

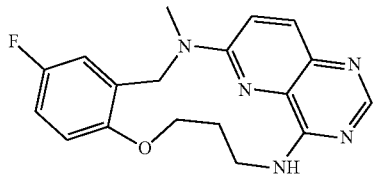 [SMILES: CN1Cc2cc(F)ccc2OCCCNc2ncnc3ccc1nc23]

6-chloro-N-(3-(5-fluoro-2-((methylamino)methyl)phenoxy)propyl)pyrido [3,2-D]pyrimidin-4-amine (40.0 mg, 106 μmol) was dissolved in N,N-dimethylformamide (2.00 mL), triethylamine (5.00 ml) was added, and the reaction solution was stirred at 120° C. for 10 hours. The organic solvent was removed from the reaction solution using a rotary evaporator, and the residue was purified by preparative Pre-HPLC to obtain 6-fluoro-2-methyl-10-oxa-2,14,16,18,22-pentaazatetracyclo [13.6.2.0$^{4,9}$.0$^{19,23}$]tricosane-1(22),4,6,8,15(23),16,18,20-octane (9.00 mg, 26.5 mol, yield 19.9%).

MS (ESI) m/z=340 (M+1)$^+$.

$^1$HNMR (400 MHz, MeOH) δ=8.41 (s, 1H), 7.84 (d, J=9.2 Hz, 1H), 7.39 (d, J=9.2 Hz, 1H), 7.21-7.18 (m, 1H), 7.06-7.02 (m, 1H), 6.97-6.92 (m, 1H), 5.69 (d, J=14.4 Hz, 1H), 4.64-4.55 (m, 2H), 4.10-4.07 (m, 1H), 3.95-3.89 (m, 1H), 3.82-3.76 (m, 1H), 3.61 (s, 3H), 2.42-2.27 (m, 2H).

Example 4. Preparation of 6-fluoro-2-methyl-10-oxa-2,13,15,17,21-pentaazatetracyclo [12.6.2.0$^4$,9.0$^{18,22}$]docosane-1(21),4,6,8,14(22),15,17,19-octane

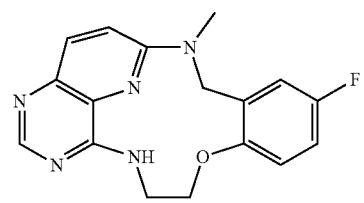 [SMILES: CN1Cc2cc(F)ccc2OCCNc2ncnc3ccc1nc23]

The same procedure as that in step 6 to step 11 of Example 3, except for using 2-((tert-butoxycarbonyl)amino)ethanol instead of 3-((tert-butoxycarbonyl)amino)propanol in step 6, was used to obtain 6-fluoro-2-methyl-10-oxa-2,13,15,17,21-pentaazatetracyclo [12.6.2.0$^4$,9.0$^{18,22}$]docosane-1(21),4,6,8,14(22),15,17,19-octane (2.8 mg, 8.61 μmol, yield 6.23%).

MS (ESI) m/z=326 (M+1)$^+$.

Example 5. Preparation of (13R)-6-fluoro-2,13-dimethyl-10-oxa-2,14,16,18,22-pentaazatetracyclo [13.6.2.0$^{4,9}$.0$^{19,23}$]tricosane-1(22),4,6,8,15(23),16,18,20-octane

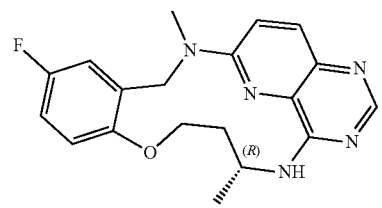

(1) Preparation of tert-butyl N-[(5-fluoro-2-hydroxy-phenyl)methyl]-N-methyl-carbamate

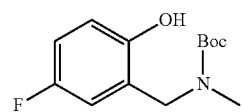

The same procedure as that in step 3 of Example 3, except for using di-tert-butyl carbonate instead of benzyloxycarbonyl succinimide as the raw material, was used to obtain tert-butyl N-[(5-fluoro-2-hydroxy-phenyl)methyl]-N-methyl-carbamate (12.0 g, 47.0 mmol, yield: 12%) (purification conditions:petroleum ether:ethyl acetate=5:1).

MS (ESI) m/z=256/200 (M+1/M+1-56)$^+$.

(2) Preparation of (R)-3-(((benzyloxy) carbonyl) amino)butyl methanesulfonate

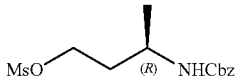

(R)-phenyl (4-hydroxybutan-2-yl)carbamate (2.40 g, 10.8 mmol) was dissolved in dichloromethane (20.0 mL), and triethylamine (3.26 g, 32.3 mmol, 4.50 mL) and methanesulfonyl chloride (2.46 g, 21.5 mmol) were added. After stirring on ice bath for 1 hour, the mixture was extracted with ethyl acetate and water, and then the aqueous phase was extracted twice with ethyl acetate. The organic phases were combined and dried over anhydrous sodium sulfate. The solvent was evaporated under reduced pressure to obtain (R)-3-(((benzyloxy) carbonyl)amino)butyl methanesulfonate (3.00 g, 9.95 mmol, yield 92%).

MS (ESI) m/z=302 (M+1)$^+$.

(3) Preparation of (R)-tert-butyl 2-(3-((benzyloxy) carbonyl)amino)butoxy)-5-fluorophenyl (methyl) carbamate

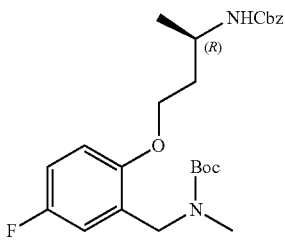

Tert-butyl N-[(5-fluoro-2-hydroxy-phenyl)methyl]-N-methyl-carbamate (1.00 g, 3.92 mmol) was dissolved in N,N-dimethylformamide (10.0 mL), and cesium carbonate (3.82 g, 11.8 mmol) and (R)-3-(((benzyloxy)carbonyl)amino)butyl methanesulfonate (1.18 g, 3.92 mmol) were added. After stirring at 70° C. for 1 hour, the mixture was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=3:1) to obtain (R)-tert-butyl 2-(3-((benzyloxy)carbonyl)amino)butoxy)-5-fluorophenyl (methyl) carbamate (1.60 g, 3.47 mmol, 88% yield).

MS (ESI) m/z=461 (M+1)$^+$

(4) Preparation of (R)-benzyl (4-(4-fluoro-2-((methylamino)methyl)phenoxy)butan-2-yl) carbamate

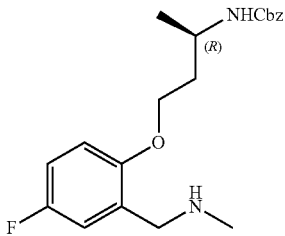

(R)-tert-butyl 2-(3-((benzyloxy)carbonyl)amino)butoxy)-5-fluorophenyl(methyl) carbamate (400 mg, 900 μmol) was dissolved in dichloromethane (10.0 ml), trifluoroacetic acid (11.9 g, 69.5 mmol) was added and the reaction solution was stirred for 1 hour. The organic solvent was removed from the reaction solution with a rotary evaporator to obtain phenyl (R)-benzyl (4-(4-fluoro-2-((methylamino)methyl)phenoxy) butan-2-yl) carbamate (1.20 g, 3.30 mmol, 95.5% yield).

MS (ESI) m/z=361 (M+1)$^+$.

(5) Preparation of (R)-benzyl (4-(4-fluoro-2-(((4-hydroxypyrido[3,2-d]pyrimidin-6-yl)(methyl) amino)methyl)phenoxy)butan-2-yl) carbamate

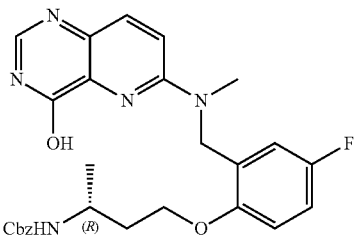

Phenyl (R)-benzyl (4-(4-fluoro-2-((methylamino)methyl) phenoxy)butan-2-yl) carbamate (900 mg, 2.50 mmol) was dissolved in n-butanol (10.0 mL), and N,N-diisopropylethylamine (21.4 g, 166 mmol) and 6-chloropyrido[3,2-d]pyrimidine-4-hydroxyl (680 mg, 3.75 mmol) were added. After stirring at 120° C. for 25 hours, the mixture was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (dichloromethane:methanol=10:1) to obtain (R)-benzyl (4-(4-fluoro-2-(((4-hydroxypyrido[3,2-d]pyrimidin-6-yl) (methyl)amino)methyl)phenoxy) butan-2-yl)carbamate (330 mg, 650 μmol, yield 26%).

MS (ESI) m/z=506 (M+1)$^+$.

(6) Preparation of (R)-6-((2-(3-aminobutoxy)-5-fluorobenzyl)(methyl)amino)pyrido[3,2-d]pyrimidine-4-hydroxyl

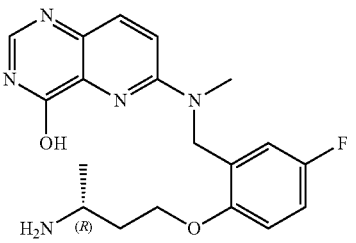

(R)-benzyl (4-(4-fluoro-2-(((4-hydroxypyrido[3,2-d]pyrimidin-6-yl)(methyl)amino) methyl)phenoxy)butan-2-yl) carbamate (330 mg, 650 μmol) was dissolved in methanol (10.0 mL), and palladium on carbon (80.0 mg) was added. After stirring at room temperature for 1 hour, the mixture was subjected to suction filtration, and the organic solvent was removed from the filtrate using a rotary evaporator to obtain (R)-6-((2-(3-aminobutoxy)-5-fluorobenzyl)(methyl)amino) pyrido[3,2-d]pyrimidine-4-hydroxyl (220 mg, 600 μmol, yield 90%).

MS (ESI) m/z=372 (M+1)+.

(7) Preparation of (13R)-6-fluoro-2,13-dimethyl-10-oxa-2,14,16,18,22-pentaazatetracyclo [13.6.2.0$^{4,9}$.0$^{19,23}$]tricosane-1(22),4,6,8,15(23),16,18,20-octane

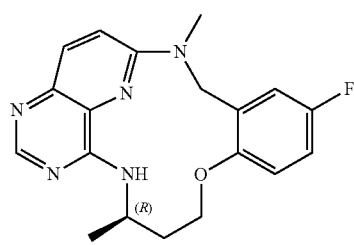

(R)-6-((2-(3-aminobutoxy)-5-fluorobenzyl)(methyl)amino)pyrido[3,2-d]pyrimidine-4-hydroxyl (200 mg, 540 μmol) was dissolved in N,N-dimethylformamide (5 mL), and benzotriazol-1-yl-oxytripyrrolidinphosphonium hexafluorophosphate (560 mg, 1.08 mmol) and N,N-diisopropylethylamine (347 mg, 2.69 mmol) were added. After stirring at room temperature for 1 hour, the mixture was extracted with ethyl acetate and water, and then the aqueous phase was extracted twice with ethyl acetate. The organic phases were combined and dried over anhydrous sodium sulfate. The solvent was evaporated under reduced pressure and the residue was purified by column chromatography (dichloromethane:methanol=20:1) to obtain (13R)-6-fluoro-2,13-dimethyl-10-oxa-2,14,16,18,22-pentaazatetracyclo [13.6.2.0$^{4,9}$.0$^{19,23}$]tricosane-1(22),4,6,8,15(23),16,18,20-octane (56.0 mg, 150 μmol, yield 28%).

MS (EST) m/z=354 (M+1)+.

$^1$H NMR (400 MHz, MeOH): δ=8.43 (s, 1H), 7.83 (d, J=9.2 Hz, 1H), 7.38 (d, J=9.2 Hz, 1H), 7.23-7.20 (m, 1H), 7.02-6.91 (m, 2H), 5.80 (d, J=14.4 Hz, 1H), 4.60-4.55 (m, 1H), 4.37-4.32 (m, 1H), 4.25-4.21 (m, 1H), 4.11-4.08 (m, 1H), 3.60 (s, 3H), 2.47-2.41 (m, 1H), 2.27-2.21 (m, 2H), 1.58 (d, J=6.4 Hz, 3H).

Example 6. Preparation of (6R,16R)-9-fluoro-16-methyl-13-oxa-2,17,19,21,25-pentaazapentacyclo [16.6.2.0$^{2,6}$.0$^{7,12}$.0,$^{26}$]hexacosane-1(25),7,9,11,18 (26),19,21,23-octane

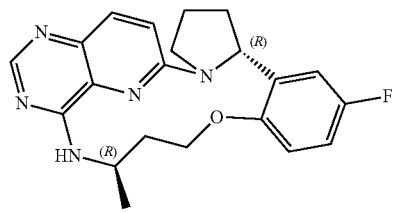

(1) Preparation of (R)-1-((S)-tert-butylsulfinyl)-2-(5-fluoro-2-methoxyphenyl)tetrahydropyrrole

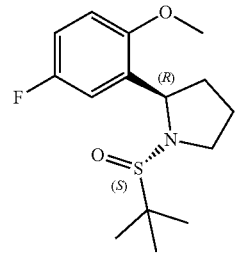

The same procedure as that in step 1 of Example 4, except for using 1-bromo-2-methyl-5-fluoro-2-bromo-4-fluoroanisole instead of 1-bromo-2-benzyloxy-5-fluorobenzene, was used to obtain (R)-1-((S)-tert-butylsulfinyl)-2-(5-fluoro-2-methoxyphenyl) tetrahydropyrrole (6.50 g, 21.7 mmol, yield 30%, purification conditions:petroleum ether:ethyl acetate=5:1).

MS (ESI) m/z=300 (M+1)+.

(2) Preparation of (R)-2-(5-fluoro-2-methoxyphenyl)tetrahydropyrrole

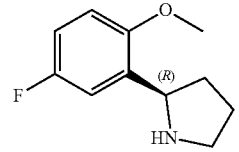

(R)-1-((S)-tert-butylsulfinyl)-2-(5-fluoro-2-methoxyphenyl)tetrahydropyrrole (6.50 g, 21.7 mmol) was dissolved in dichloromethane (5.00 ml), and dioxane hydrochloride (15.0 ml, 2 M) was added, and the reaction solution was stirred at 0° C. for 1 hour. The organic solvent was removed from the reaction solution using a rotary evaporator to obtain a gray solid. The solid was stirred in petroleum ether, and filtered with suction to obtain a light gray solid, which was spin-dried to obtain (R)-2-(5-fluoro-2-methoxyphenyl)tetrahydropyrrole (4.20 g, 21.5 mmol, 99% yield).

MS (ESI) m/z=196 (M+1)+.

(3) Preparation of (R)-6-(2-(5-fluoro-2-methoxyphenyl)tetrahydropyrrol-1-yl)pyrido[3,2-d]pyrimidine-4-hydroxyl

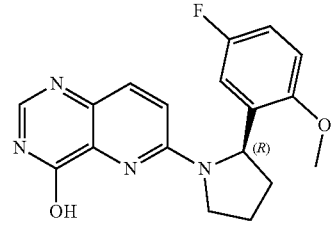

(R)-2-(5-fluoro-2-methoxyphenyl)tetrahydropyrrole (1.60 g, 8.28 mmol) was dissolved in n-butanol (10.0 mL)

and N,N-diisopropylethylamine (21.4 g, 166 mmol) and 6-chloropyrido [3,2-d]pyrimidine-4-hydroxyl (2.36 g, 9.11 mmol) were added. After stirring at 120° C. for 48 hours, the mixture was extracted with ethyl acetate and water, and the aqueous phase was extracted twice with ethyl acetate. The organic phases were combined and dried over anhydrous sodium sulfate. The solvent was evaporated under reduced pressure and the residue was purified by MPLC [mobile phase:acetonitrile/water (containing 0.05% trifluoroacetic acid)=7/1] to obtain (R)-6-(2-(5-fluoro-2-methoxyphenyl) tetrahydropyrrol-1-yl)pyrido[3,2-d]pyrimidine-4-hydroxyl (1.30 g, 3.82 mmol, yield 46.1%).

MS (ESI) m/z=341 (M+1)+.

(4) Preparation of (R)-4-chloro-6-(2-(5-fluoro-2-methoxyphenyl)tetrahydropyrrol-1-yl)pyrido [3,2-d] pyrimidine

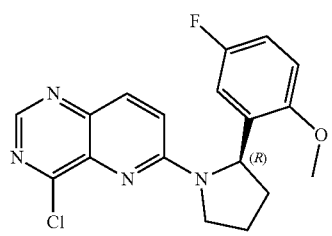

(R)-6-(2-(5-fluoro-2-methoxyphenyl)tetrahydropyrrol-1-yl)pyrido[3,2-d]pyrimidine-4-hydroxyl (1.30 g, 3.82 mmol) was dissolved in dichlorosulfoxide (15.0 ml) and stirred at 80° C. for 1 hour. The organic solvent was removed from the reaction solution using a rotary evaporator, and dichloromethane was added. The reaction was quenched with a saturated solution of sodium bicarbonate, extracted, and the aqueous phase was extracted twice with dichloromethane. The organic phases were combined and dried over anhydrous sodium sulfate. The solvent was evaporated under reduced pressure and the residue was purified by column chromatography (petroleum ether:ethyl acetate=3:1) to obtain (R)-4-chloro-6-(2-(5-fluoro-2-methoxyphenyl) tetrahydropyrrol-1-yl)pyrido[3,2-d]pyrimidine (1.20 g, 3.34 mmol, yield 83%).

MS (ESI) m/z=359 (M+1)+.

(5) Preparation of (R)-2-(1-(4-chloropyrido[3,2-d] pyrimidin-6-yl)tetrahydropyrrol-2-yl)-4-fluorophenol

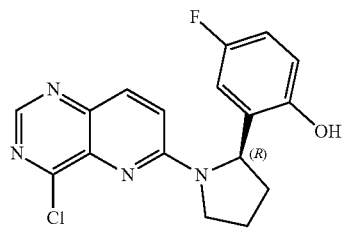

(R)-4-chloro-6-(2-(5-fluoro-2-methoxyphenyl)tetrahydropyrrol-1-yl)pyrido[3,2-d]pyrimidine (1.20 g, 3.34 mmol) was dissolved in 1,2-dichloroethane (5.00 ml), and boron trichloride (33.4 mmol) was added, and the reaction solution was stirred at 70° C. for 5 hours. The organic solvent was removed from the reaction solution using a rotary evaporator, and dichloromethane was added. The reaction was quenched with a saturated solution of sodium bicarbonate, extracted, and the aqueous phase was extracted twice with dichloromethane. The organic phases were combined and dried over anhydrous sodium sulfate. The solvent was evaporated under reduced pressure and the residue was purified by column chromatography (petroleum ether:ethyl acetate=2:1) to obtain (R)-2-(1-(4-chloropyrido[3,2-d]pyrimidin-6-yl) tetrahydropyrrol-2-yl)-4-fluorophenol (700 mg, 2.03 mmol, yield 60%).

MS (ESI) m/z=345 (M+1)+.

(6) Preparation of (tert-butyl ((R)-4-(2-((R)-1-(4-chloropyrido[3,2-d]pyrimidin-6-yl) tetrahydropyrrol-2-yl)-4-fluorophenoxy) butan-2-yl) carbamate

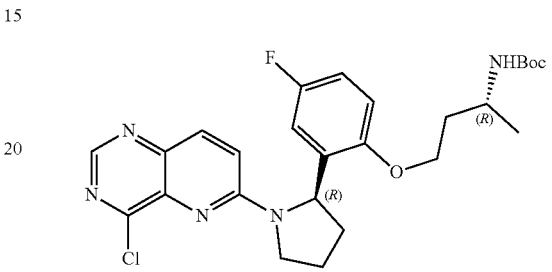

(R)-2-(1-(4-chloropyrido[3,2-d]pyrimidin-6-yl)tetrahydropyrrol-2-yl)-4-fluorophenol (240 mg, 700 µmol) was dissolved in N-methylpyrrolidone (5.00 mL), add cesium carbonate (678 mg, 2.09 mmol) and [(3R)-3-(tert-butoxycarbonylamino)butyl]methanesulfonate (279 mg, 1.04 mmol) were added. After stirring at 70° C. for 3 hours, the mixture was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=1:1) to obtain (tert-butyl ((R)-4-(2-((R)-1-(4-chloropyrido[3,2-d]pyrimidin-6-yl) tetrahydropyrrol-2-yl)-4-fluorophenoxy)butan-2-yl) carbamate (70.0 mg, 130 µmol, yield 19.5%).

MS (ESI) m/z=516 (M+1)+.

(7) Preparation of (R)-4-(2-((R)-1-(4-chloropyrido [3,2-d]pyrimidin-6-yl)tetrahydropyrrol-2-yl)-4-fluorophenoxy)butan-2-amine

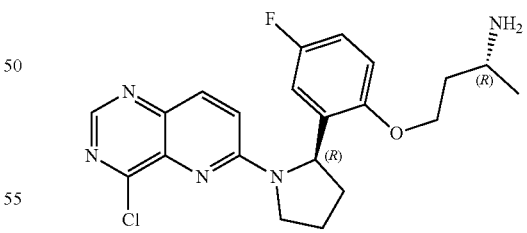

(Tert-butyl ((R)-4-(2-((R)-1-(4-chloropyrido[3,2-d]pyrimidin-6-yl)tetrahydropyrrol-2-yl)-4-fluorophenoxy)butan-2-yl)carbamate (70.0 mg, 130 µmol) was dissolved in methylene chloride (3.00 ml), boron trichloride (160 µmol, 160 µl) was added, and the reaction solution was stirred at 0° C. for 2 hours. The reaction was quenched with saturated sodium bicarbonate solution, extracted with dichloromethane and water and the aqueous phase was extracted twice with dichloromethane. The organic phases were combined and dried over anhydrous sodium sulfate. The solvent was evaporated under reduced pressure to obtain (R)-4-(2-((R)-

1-(4-chloropyrido [3,2-d]pyrimidin-6-yl)tetrahydropyrrol-2-yl)-4-fluorophenoxy)butan-2-amine (40.0 mg, 90.0 μmol, 71% yield).

MS (ESI) m/z=416 (M+1)$^+$.

(8) Preparation of (6R,16R)-9-fluoro-16-methyl-13-oxa-2,17,19,21,25-pentaazapentacyclo[16.6.2.0$^{2,6}$.0$^{7,12}$.0$^{22,26}$]hexacosane-1(25),7,9,11,18(26),19,21,23-octane

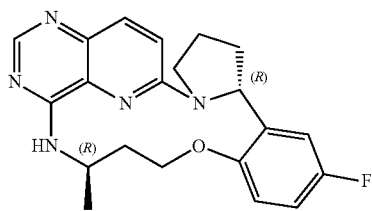

(R)-4-(2-((R)-1-(4-chloropyrido[3,2-d]pyrimidin-6-yl)tetrahydropyrrol-2-yl)-4-fluorophenoxy)butan-2-amine (40.0 mg, 90.0 μmol) was dissolved in isopropanol (8.00 mL), N,N-diisopropylethylamine (900 μmol, 350 μl) was added, and the reaction solution was stirred at 90° C. for 10 hours. The organic solvent was removed from the reaction solution using a rotary evaporator and the residue was purified by preparative Pre-HPLC to obtain (6R,16R)-9-fluoro-16-methyl-13-oxa-2,17,19,21,25-pentaazapentacyclo[16.6.2.0$^{2,6}$.0$^{7,12}$.0$^{22,26}$]hexacosane-1(25),7,9,11,18(26),19,21,23-octane (5.60 mg, 14.0 μmol, yield 14.5%).

MS (ESI) m/z=380 (M+1)$^+$.

Example 7. Preparation of (6R,14S)-9-fluoro-14-methyl-13-oxa-2,17,19,21,25-pentaazapentacyclo[16.6.2.0$^{2,6}$.0$^{7,12}$.0$^{22,26}$]hexacosane-1(25),7,9,11,18(26),19,21,23-octane

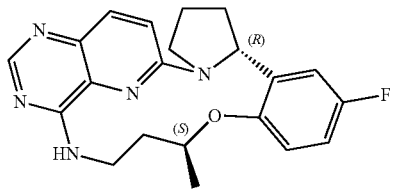

(1) Preparation of 2-((R)-1-(4-((2,4-dimethoxybenzyl(R)-3-hydroxybutyl)amino)pyrido[3,2-d]pyrimidin-6-yl)tetrahydropyrrol-2-yl)-4-fluorophenol

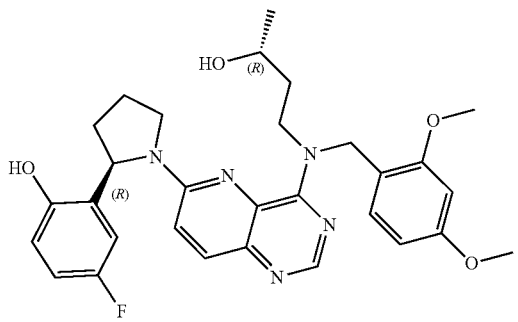

(R)-2-(1-(4-chloropyrido[3,2-d]pyrimidin-6-yl)tetrahydropyrrol-2-yl)-4-fluorophenol (100 mg, 290 μmol) was dissolved in isopropyl alcohol (5.00 mL), N,N-diisopropylethylamine (5.00 ml) and (2R)-4-[(2,4-dimethoxybenzyl)methylamino]butane-2-hydroxyl (104 mg, 430 μmol) were added. After stirring at 90° C. for 3 hours, the mixture was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (dichloromethane:methanol=10:1) to obtain 2-((R)-1-(4-((2,4-dimethoxybenzyl) ((R)-3-hydroxybutyl)amino)pyrido[3,2-d]pyrimidin-6-yl)tetrahydropyrrol-2-yl)-4-fluorophenol (100 mg, 180 μmol, yield 62.1%).

MS (ESI) m/z=548 (M+1)$^+$.

(2) Preparation of (6R,14S)-17-[(2,4-dimethoxyphenyl)methyl]-9-fluoro-14-methyl-13-oxa-2,17,19,21,25-pentaazapentacyclo[16.6.2.0$^{2,6}$.0$^{7,12}$.0$^{22,26}$]hexacosane-1(25),7,9,11,18(26),19,21,23-octane

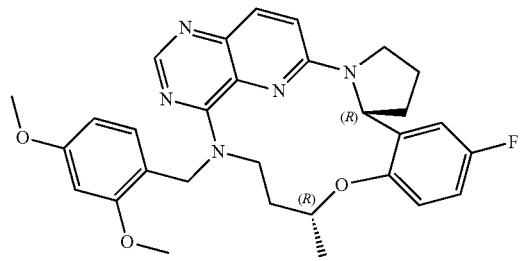

2-((R)-1-(4-((2,4-dimethoxybenzyl)((R)-3-hydroxybutyl)amino)pyrido[3,2-d] pyrimidin-6-yl)tetrahydropyrrol-2-yl)-4-fluorophenol (100 mg, 180 μmol) was dissolved in tetrahydrofuran (2.50 mL), and diisopropyl azodicarboxylate (116 mg, 550 μmol) and triphenylphosphine oxide (143 mg, 550 μmol) were added on ice bath, and stirred at room temperature for 3 hours under nitrogen atmosphere. The mixture was extracted with ethyl acetate and water and the aqueous phase was extracted twice with ethyl acetate. The organic phases were combined and dried over anhydrous sodium sulfate. The solvent was evaporated under reduced pressure and the residue was purified by MPLC (mobile phase:acetonitrile/water=10/1) to obtain (6R,14S)-17-[(2,4-dimethoxyphenyl)methyl]-9-fluoro-14-methyl-13-oxa-2,17,19,21,25-pentaazapentacyclo[16.6.2.0$^{2,6}$.0$^{7,12}$.0$^{22,26}$]hexacosane-1(25),7,9,11,18(26),19,21,23-octane (70.0 mg, 130 μmol, yield 72.3%).

MS (ESI) m/z=530 (M+1)$^+$.

(3) Preparation of (6R,14S)-9-fluoro-14-methyl-13-oxa-2,17,19,21,25-pentaazapentacyclo[16.6.2.0$^{2,6}$.0$^{7,12}$.0$^{22,26}$]hexacosane-1(25),7,9,11,18(26),19,21,23-octane

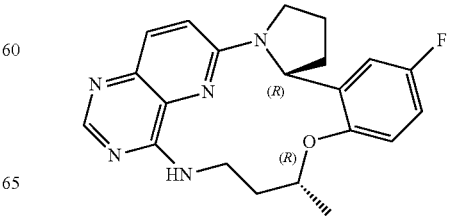

(6R,14S)-17-[(2,4-dimethoxyphenyl)methyl]-9-fluoro-14-methyl-13-oxa-2,17,19,21,25-pentaazapentacyclo [16.6.2.0$^{2,6}$.0$^{7,12}$.0$^{22,26}$]hexacosane-1(25),7,9,11,18(26),19,21,23-octane (70.0 mg, 130 μmol) was dissolved in dichloromethane (3.00 mL), and trifluoroacetic acid (1.00 mL) was added on ice bath. After stirring at room temperature for 2 hours, the mixture was extracted with ethyl acetate and water, and then the aqueous phase was extracted twice with ethyl acetate. The organic phases were combined and dried over anhydrous sodium sulfate. The solvent was evaporated under reduced pressure and the residue was purified by MPLC (mobile phase: acetonitrile/water (containing 0.5% trifluoroacetic acid)=1/3) to obtain (6R,14S)-9-fluoro-14-methyl-3-oxa-2,17,19,21,25-pentaazapentacyclo[16.6.2.0$^{2,6}$.0$^{7,12}$.0$^{22,26}$]hexacosane-1(25),7,9,11,18(26),19,21,23-octane (16.0 mg, 30 μmol, yield 23.3%).

MS (ESI) m/z=380 (M+1)$^+$.

Example 8. Preparation of (6R,16S)-9-fluoro-16-methyl-3-oxa-2,17,21,25-tetraazapentacyclo [16.6.2.0$^{2,6}$.0$^{7,12}$.0$^{22,26}$]hexacosane-1(25),7,9,11,18 (26),19,21,23-octane-19-nitrile

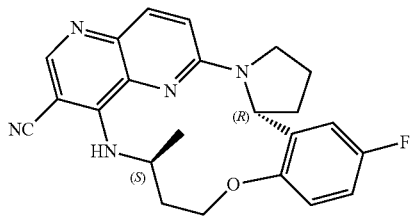

The same procedure as that in step 7 to step 14 of Example 1, except for using (S)-3-((tert-butoxycarbonyl)amino)butyl methanesulfonate instead of (R)-3-((tert-butoxycarbonyl) amino)butyl methylsulfonate in step 7, was used to obtain (6R,16S)-9-fluoro-16-methyl-3-oxa-2,17,19,21,25-tetraazapentacyclo[16.6.2.0$^{2,6}$.0$^{7,12}$.0$^{22,26}$]hexacosane-1(25),7,9,11,18(26),19,21,23-octane-9-nitrile (15.3 mg, 38 μmol, yield 9.3%).

MS (ESI) m/z=390 (M+1)$^+$.

Example 9. Preparation of ethyl (6R)-9-fluoro-13-oxa-2,17,21,25-tetraazapentacyclo [16.6.2.0$^{2,6}$.0$^{7,12}$.0$^{22,26}$]hexacosane-1(25),7,9,11,18(26),19,21,23-octane-19-carboxylate

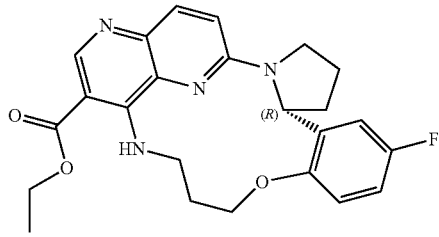

The same procedure as that in step 7 to step 11 of Example 1, except for using 3-((tert-butoxycarbonyl)amino)propyl methanesulfonate instead of (R)-3-((tert-butoxycarbonyl) amino)butyl methylsulfonate in step 7, was used to obtain ethyl (6R)-9-fluoro-13-oxa-2,17,21,25-tetraazapentacyclo [16.6.2.0$^{2,6}$.0$^{7,12}$.0$^{22,26}$]hexacosane-1(25),7,9,11,18(26),19,21,23-octane-9-carboxylate (80.0 mg, 0.18 mmol, yield 32.1%).

MS (ESI) m/z=437 (M+1)$^+$.

$^1$H NMR (400 MHz, CDCl$_3$): δ=9.35 (s, 1H), 8.80 (s, 1H), 8.04 (d, J=8.0 Hz, 1H), 7.03-6.97 (m, 2H), 6.89-6.83 (m, 2H), 5.95-5.93 (m, 1H), 4.71-4.60 (m, 1H), 4.44-4.32 (m, 4H), 4.12 (s, 1H), 4.1-3.96 (m, 1H), 3.68-3.61 (m, 1H), 2.48-2.14 (m, 4H), 2.06-2.01 (m, 2H), 1.91-1.84 (m, 1H), 1.41 (t, J=7.2 Hz, 3H).

Example 10. Preparation of (6R)-9-fluoro-13-oxa-2,17,21,25-tetraazapentacyclo [16.6.2.0$^{2,6}$.0$^{7,12}$.0$^{22,26}$] hexacosane-1(25),7,9,11,18(26),19,21,23-octane-19-carboxylic acid

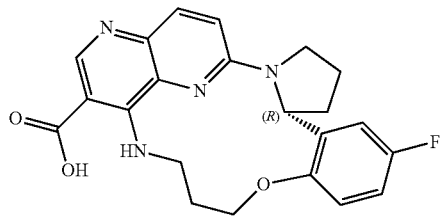

The same procedure as that in step 7 to step 12 of Example 1, except for using 3-((tert-butoxycarbonyl)amino)propyl methanesulfonate instead of (R)-3-((tert-butoxycarbonyl) amino)butyl methylsulfonate in step 7, was used to obtain (6R)-9-fluoro-13-oxa-2,17,21,25-tetraazapentacyclo [16.6.2.0$^{2,6}$.0$^{7,12}$.0$^{22,26}$]hexacosane-1(25),7,9,11,18(26),19,21,23-octane-9-carboxylic acid (49.0 mg, 0.12 mmol, yield 25.2%).

MS (ESI) m/z=409 (M+1)$^+$.

$^1$H NMR (400 MHz, CDCl$_3$): δ=11.16 (s, 1H), 8.98 (s, 1H), 8.43 (d, J=9.2 Hz, 1H), 7.13 (d, J=9.6 Hz, 1H),7.04-7.01 (m, 1H), 6.90-6.86 (m, 1H), 6.77-6.75 (m, 1H), 5.88 (d, J=7.61 Hz, 1H), 4.72-4.68 (m, 1H), 4.38 (s, 1H), 4.23-4.20 (m, 1H), 4.03-3.92 (m, 1H), 3.68-3.64 (m, 1H), 2.48-2.18 (m, 5H), 2.01-1.98 (m, 1H), 1.88-1.86 (m, 1H).

Example 11. Preparation of (6R)-9-fluoro-13-oxa-2,17,21,25-tetraazapentacyclo [16.6.2.0$^{2,6}$.0$^{7,12}$.0$^{22,26}$] hexacosane-1(25),7,9,11,18(26),19,21,23-octane-19-carboxamide

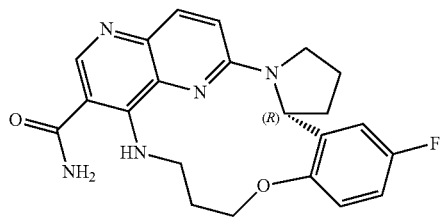

The same procedure as that in step 7 to step 13 of Example 1, except for using 3-((tert-butoxycarbonyl)amino)propyl methanesulfonate instead of (R)-3-((tert-butoxycarbonyl) amino)butyl methylsulfonate in step 7, was used to obtain (6R)-9-fluoro-13-oxa-2,17,21,25-tetraazapentacyclo [16.6.2.0$^2$.0$^{7,12}$.0$^{22,26}$]hexacosane-1(25),7,9,11,18(26),19,21,23-octane-9-carboxamide (28.9 mg, 71.0 μmol, yield 13.2%).

MS (ESI) m/z=408 (M+1)+.
¹H NMR (400 MHz, CDCl₃): δ=9.50 (s, 1H), 8.48 (s, 1H), 7.99 (d, J=8.0 Hz, 1), 7.0 (d, J=8.0 Hz, 1H), 6.96-6.84 (m, 2H), 5.94-5.92 (m, 1H), 4.48-4.40 (m, 2H), 4.34-4.25 (m, 1H), 4.1-3.89 (m, 2H), 3.68-3.62 (m, 1H), 2.51-2.35 (m, 2H), 2.33-2.23 (m, 1H), 2.21-2.12 (m, 1H), 2.10-2.05 (m, 1H), 1.93-1.88 (m, 1H).

Example 12. Preparation of (6R)-9-fluoro-13-oxa-2,17,21,25-tetraazapentacyclo [16.6.2.0²,⁶.0⁷,¹².0²²,²⁶]hexacosane-1(25),7,9,11,18(26),19,21,23-octane-19-nitrile

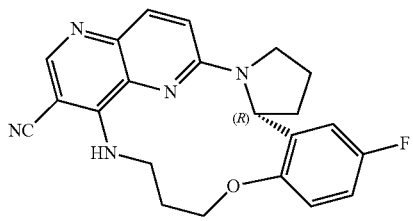

The same procedure as that in step 7 to step 14 of Example 1, except for using 3-((tert-butoxycarbonyl)amino)propyl methanesulfonate instead of (R)-3-((tert-butoxycarbonyl)amino)butyl methylsulfonate in step 7, was used to obtain (6R)-9-fluoro-13-oxa-2,17,21,25-tetraazapentacyclo [16.6.2.0²,⁶.0⁷,¹².0²²,²⁶]hexacosane-1(25),7,9,11,18(26),19,21,23-octane-19-nitrile (11.3 mg, 29.0 μmol, yield 7.2%).

MS (ESI) m/z=390 (M+1)+.
¹H NMR (400 MHz, CDCl₃): δ=9.26 (s, 1H), 8.27 (s, 1H), 7.94 (d, J=9.2 Hz, 1H), 7.04 (dd, J=9.6 Hz, J=3.2 Hz, 1H), 6.98-6.96 (m, 1H), 6.93-6.82 (m, 2H), 5.87-5.83 (m, 1H), 4.59-4.54 (m, 1H), 4.47-4.43 (m, 1H), 4.10-4.06 (m, 2H), 4.01-3.95 (m, 1H), 3.72-3.67 (m, 1H), 2.56-2.28 (m, 4H), 2.23-2.13 (m, 1H), 2.03-1.94 (m, 1H).

Example 13. Preparation of (6S,16S)-9-fluoro-16-methyl-13-oxa-2,17,21,25-tetraazapentacyclo [16.6.2.0²,⁶.0⁷,¹².0²²,²⁶]hexacosane-1(25),7,9,11,18(26),19,21,23-octane-19-nitrile

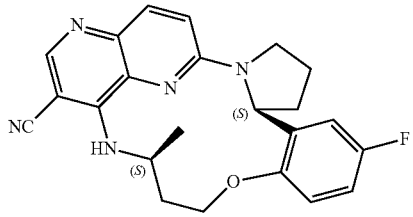

The same procedure as that in step 3 to step 14 of Example 1, except for using (R)-tert-butylsulfinamide instead of (S)-tert-butylsulfinamide in step 3, and using (S)-3-((tert-butoxycarbonyl)amino)propyl methanesulfonate instead of (R)-3-((tert-butoxycarbonyl) amino)butyl methylsulfonate in step 7, was used to obtain (6S,16S)-9-fluoro-16-methyl-3-oxa-2,17,21,25-tetraazapentacyclo[16.6.2.0²,⁶.0⁷,¹².0²², ²⁶]hexacosane-1(25),7,9,11,18(26),19,21,23-octane-9-nitrile (141 mg, 0.36 mmol, 12% yield).

MS (ESI) m/z=404 (M+1)+.

Example 14. Preparation of (6S,16R)-9-fluoro-16-methyl-3-oxa-2,17,21,25-tetraazapentacyclo [16.6.2.0²,⁶.0⁷,¹².0²²,²⁶]hexacosane-1(25),7,9,11,18 (26),19,21,23-octane-19-nitrile

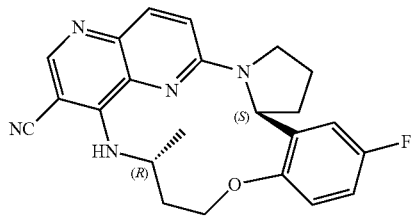

The same procedure as that in step 3 to step 14 of Example 1, except for using (R)-tert-butylsulfinamide instead of (S)-tert-butylsulfinamide in step 3, was used to obtain (6S,16R)-9-fluoro-16-methyl-3-oxa-2,17,21,25-tetraazapentacyclo[16.6.2.0²,⁶.0⁷,¹².0²²,²⁶]hexacosane-1(25),7,9,11,18 (26),19,21,23-octane-19-nitrile (73 mg, 0.19 mmol, 13% yield).

MS (ESI) m/z=404 (M+1)+.

Example 15. Preparation of (6R)-9-fluoro-2,11,17,19,21,25-hexaazapentacyclo [16.6.2.0²,⁶.0⁷,¹².0²²,²⁶]hexacosane-1(25),7,9,11,18(26),19,21,23-octane

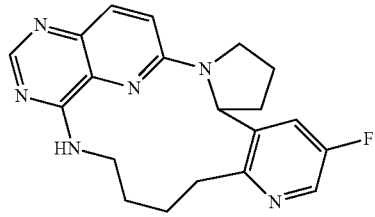 [SMILES: Fc1cnc2c(c1)C1CCCN1c1ccc3ncnc(c3n1)NCCCC2]

(1) Preparation of tert-butyl 2-(2-chloro-5-fluoro-pyridin-3-yl)-tetrahydropyrrole-1-carboxylate

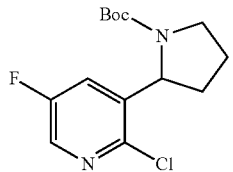 [SMILES: CC(C)(C)OC(=O)N1CCCC1c1cc(F)cnc1Cl]

Under nitrogen atmosphere, 1-tert-butoxycarbonyl-pyrrolidine (9.42 g, 55.0 mmol) was dissolved in anhydrous tetrahydrofuran (120 mL). Sec-butyl lithium (55.0 mL, 1.0 M, 55.0 mmol) was added dropwise at −40° C., and the reaction was allowed to proceed at −40° C. for 10 minutes after the addition, and then a solution of zinc chloride in tetrahydrofuran (33.0 mL, 1.0 M, 33.0 mmol) was added dropwise. After the addition, the reaction mixture was slowly warmed to room temperature, and stirred for additional 30 minutes. Under nitrogen atmosphere, 2-chloro-3-bromo-5-fluoropyridine (10.5 g, 50.0 mmol), palladium acetate (560 mg, 2.50 mmol) and tri-tert-butylphosphine tetrafluoroborate (910 mg, 3.10 mmol) were added. After stirring at room temperature for 16 hours, the mixture was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=4:1) to obtain tert-butyl 2-(2-chloro-5-fluoropyridin-3-yl)-tetrahydropyrrole-1-carboxylate (3.80 g, 12.6 mmol, yield 25%).

MS (ESI) m/z=301 (M+1)$^+$.

(2) Preparation of tert-butyl 2-(2-(3-(((benzyloxy) formyl)amino)propyl-1-yn-1-yl)-5-fluoropyridin-3-yl) tetrahydropyrrole-1-carboxylate

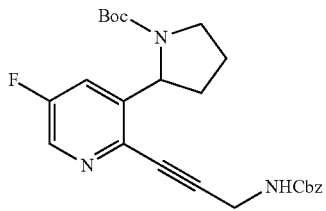 [SMILES: CC(C)(C)OC(=O)N1CCCC1c1cc(F)cnc1C#CCNC(=O)OCc1ccccc1]

Tert-butyl 2-(2-chloro-5-fluoropyridin-3-yl)-tetrahydropyrrole-1-carboxylate (902 mg, 3.00 mmol) was dissolved in N,N-dimethylformamide (10.0 mL), and benzyl 2-propyn-1-carbamate (671 mg, 3.30 mmol), [1,1'-bis(diphenylphosphino)ferrocene]palladium dichloride (219 mg, 300 μmol), cuprous iodide (114 mg, 400 μmol) and triethylamine (1.52 g, 15.0 mmol, 2.09 mL) were added. Under nitrogen atmosphere, the mixture was stirred at 100° C. for 16 hours. The solvent was evaporated under reduced pressure and residue was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (petroleum ether:ethyl acetate=2:1) to obtain tert-butyl 2-(2-(3-(((benzyloxy)formyl)amino)propyl-1-yn-1-yl)-5-pyridin-3-yl) tetrahydropyrrole-1-carboxylate (900 mg, 1.93 mmol, yield 64%).

MS (ESI) m/z=454 (M+1)$^+$.

(3) Preparation of tert-butyl 2-(2-(3-aminopropyl)-5-fluoropyridin-3-yl) tetrahydropyrrole-1-carboxylate

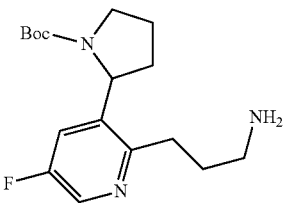 [SMILES: CC(C)(C)OC(=O)N1CCCC1c1cc(F)cnc1CCCN]

Tert-butyl 2-(2-(3-(((benzyloxy)formyl)amino)propyl-1-yn-1-yl)-5-pyridin-3-yl) tetrahydropyrrole-1-carboxylate (900 mg, 1.93 mmol) was dissolved in methanol (20.0 mL), and palladium carbon (90.0 mg) was added at room temperature. The mixture was stirred at room temperature under hydrogen atmosphere for 6 hours. The solid was removed by filtration, and the solvent was evaporated under reduced pressure to obtain tert-butyl 2-(2-(3-aminopropyl)-5-fluoropyridin-3-yl)tetrahydropyrrole-1-carboxylate (600 mg, 1.78 mmol, yield 92%).

MS (ESI) m/z=324 (M+1)$^+$.

(4) Preparation of tert-butyl 2-(2-(4-((6-chloropyrido[3,2-d]pyrimidin-4-yl)amino)butyl)-5-fluoropyridin-3-yl)tetrahydropyrrole-1-carboxylate

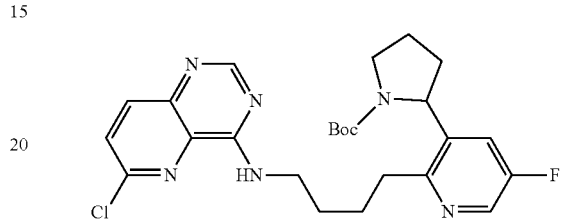

Tert-butyl 2-(2-(3-aminopropyl)-5-fluoropyridin-3-yl)tetrahydropyrrole-1-carboxylate (600 mg, 1.78 mmol) was dissolved in N,N-dimethylformamide (6.00 mL), and 6-chloro-3H-pyrido[3,2-d]pyrimidin-4-one (356 mg, 1.78 mmol), benzotriazol-1-yl-oxytripyrrolidinphosphonium hexafluorophosphate (347 mg, 2.13 mmol) and N,N-diisopropylethylamine (1.15 g, 8.89 mmol) were added, and stirred at room temperature for 2 hours. The mixture was extracted with ethyl acetate and water, and the organic phase was collected and dried over anhydrous sodium sulfate. The residue was purified by column chromatography (methanol:dichloromethane=1:12) to obtain tert-butyl 2-(2-(4-((6-chloropyrido[3,2-d]pyrimidin-4-yl)amino)butyl)-5-fluoropyridin-3-yl) tetrahydropyrrole-1-carboxylate (700 mg, 1.40 mmol, yield 78.6%).

MS (ESI) m/z=501 (M+1)$^+$.

(5) Preparation of 6-chloro-N-(4-(5-fluoro-3-(pyridin-2-yl)tetrahydropyrrol-2-yl)butyl)pyrido [3,2-d] pyrimidin-4-amine

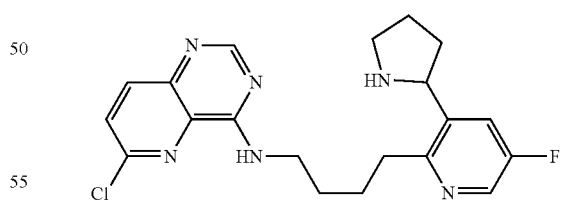

Tert-butyl 2-(2-(4-((6-chloropyrido[3,2-d]pyrimidin-4-yl)amino)butyl)-5-fluoropyridin-3-yl) tetrahydropyrrole-1-carboxylate (700 mg, 1.40 mmol) was dissolved in dichloromethane (3.00 mL), and trifluoroacetic acid (3.00 mL) was added. After stirring the reaction solution at 0° C. for 2 hours, the solvent was evaporated under reduced pressure to obtain 6-chloro-N-(4-(5-fluoro-3-(pyridin-2-yl)tetrahydropyrrol-2-yl)butyl)pyrido[3,2-d]pyrimidin-4-amine (520 mg, 1.30 mmol, yield 92.8%).

MS (ESI) m/z=401 (M+1)$^+$.

(6) Preparation of (6R)-9-fluoro-2,11,17,19,21,25-hexaazapentacyclo [16.6.2.0$^{2,6}$.0$^{7,12}$.0$^{22,26}$]hexacosane-(25),7,9,11,18(26),19,21,23-octane

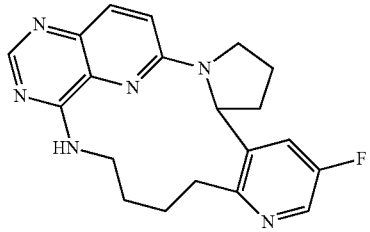 [SMILES: Fc1cnc2c(c1)C1CCCN1c1ccc3ncnc(c3n1)NCCCC2]

The same procedure as that in step 11 of Example 1, except for using 6-chloro-N-(4-(5-fluoro-3-(pyridin-2-yl)tetrahydropyrrole-2-yl)butyl)pyrido[3,2-d]pyrimidin-4-amine (0.52 g, 1.30 mmol) instead of ethyl 6-chloro-4-(((R)-4-(4-fluoro-2-((R)-tetrahydropyrrol-2-yl)phenoxy)butyl-2-yl)amino)1,5-naphthyridine-3-carboxylate, was used to obtain (6R)-9-fluoro-2,11,17,19,21,25-hexaazapentacyclo [16.6.2.0$^{2,6}$.0$^{7,12}$.0$^{22,26}$]hexacosane-1(25),7,9,11,18(26),19,21,23-octane (7.10 mg, 19.0 μmol, yield 3.91%).

MS (ESI) m/z=365 (M+$^{1}$)$^{+}$.

$^{1}$H NMR (400 MHz, MeOD): δ=8.26 (d, J=2.8, 1H), 8.04 (s, 1H), 7.83 (d, J=9.2, 1H), 7.36-7.30 (m, 2H), 5.69 (s, 1H), 4.10-4.04 (m, 1H), 3.71-3.60 (m, 2H), 3.14-3.08 (m, 1H), 2.86-2.82 (m, 1H), 2.60-2.50 (m, 1H), 2.23-2.04 (m, 6H), 1.85-1.79 (n, 2H).

Example 16. Preparation of (6R,16R)-9-fluoro-16-methyl-2,11,17,19,21,25-hexaazapentacyclo [16.6.2.0$^{2,6}$.0$^{7,12}$.0$^{22,26}$]hexacosane-1(25),7,9,11,18(26),19,21,23-octane

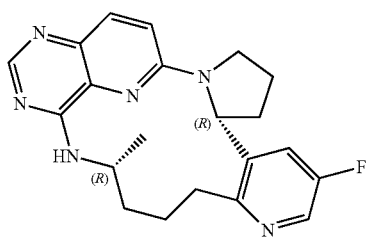

The same procedure as that in step 2 to step 6 of Example 13, except for using (R)-benzyl-3-pentyn-2-ylcarbamic acid instead of benzyl 3-butyne-1-carbamate in step 2, was used to obtain (6R,16R)-9-fluoro-16-methyl-2,11,17,19,21,25-hexaazapentacyclo [16.6.2.0$^{2,6}$.0$^{7,12}$.0$^{22,26}$] hexacosane-1(25),7,9,11,18(26),19,21,23-octane (6.2 mg, 16.3 μmol, total yield 3.2%).

MS (ESI) m/z=379 (M+1)$^{+}$.

Example 17. Preparation of 6-fluoro-3-methyl-10-oxa-2,14,16,18,22-pentaazatetracyclo [13.6.2.0$^{4,9}$.0$^{19,23}$] tricosane-1 (22),4,6,8,15(23),16,18,20-octane

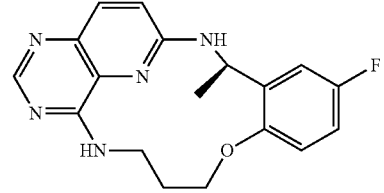 [SMILES: C[C@H]1Nc2ccc3ncnc(c3n2)NCCCOc2ccc(F)cc21]

(1) Preparation of 1-(2-benzyloxy-5-fluorophenyl)-ethanone

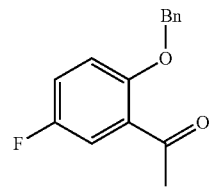

1-(2-hydroxy-5-fluorophenyl)-ethanone (100 g, 649 mmol) and benzyl bromide (122 g, 714 mmol) and potassium carbonate (271 g, 1.95 mol) were added to DMF (100 mL), and stirred at 90° C. for 4 hours. The mixture was extracted with ethyl acetate, and the organic phase was collected. The solvent was removed by a rotary evaporator and the residue was separated by silica gel column chromatography (PE:EA=5:1) to obtain a yellow oily liquid (93 g, 381 mmol, yield 59%).

MS (ESI) m/z=245 (M+1)$^{+}$.

(2) Preparation of (S)—N-(1-(2-benzyloxy-5-fluorophenyl)ethylimino)-2-methylpropyl-2-sulfinamide

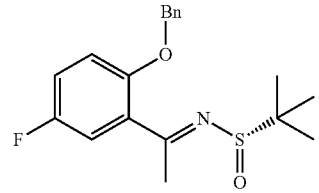 [SMILES: C/C(=N\[S@@](=O)C(C)(C)C)c1cc(F)ccc1OCc1ccccc1]

1-(2-Benzyloxy-5-fluorophenyl)-ethanone (83 g, 340 mmol) and (S)-tert-butyl sulfinamide (103 g, 850 mmol) and tetraethyl titanate (101 g, 442 mmol) were added tetrahydrofuran (500 mL), and stirred at 80° C. for 4 hours. After the reaction was completed, 100 mL of water was added, the solid was removed by suction filtration, and the residue was extracted with ethyl acetate (500 mL) and water (500 mL). The organic phase was collected and dried over anhydrous sodium sulfate. The solvent was removed by a rotary evaporator, and the residue was separated by silica gel column chromatography (PE:EA=3:1) to obtain a yellow oily liquid (65 g, 187 mmol, yield 55%).

MS (ESI) m/z=348 (M+1)$^{+}$.

(3) Preparation of (S)—N—((R)-1-(2-benzyloxy-5-fluorophenylethyl)-2-methylpropyl-2-sulfinamide

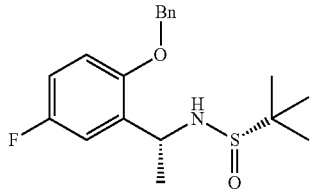 [SMILES: C[C@@H](N[S@@](=O)C(C)(C)C)c1cc(F)ccc1OCc1ccccc1]

Under nitrogen atmosphere, (S)—N-(1-(2-benzyloxy-5-fluorophenyl)ethylimino)-2-methylpropyl-2-sulfinamide (91.2 g, 263 mmol) was dissolved in anhydrous tetrahydrofuran (500 ml). A solution of lithium triethylborohydride in tetrahydrofuran (393 mL, 1.0 M, 393 mmol) was added dropwise at −78° C., and the reaction was allowed to proceed at −78° C. for 3 hours after the addition. The mixture was warmed to room temperature and stirred for 2 hours, and then the reaction was quenched with saturated ammonium chloride solution. The reaction mixture was extracted with ethyl acetate, and the organic phase was washed twice with saturated brine. The organic phases were combined and dried over anhydrous sodium sulfate, and the solvent was evaporated under reduced pressure. The residue was purified by column chromatography (PE:EA=3:1) to obtain a yellow oily liquid (82 g, 234 mmol, 89% yield).

MS (ESI) m/z=350 (M+1)$^+$.

(4) Preparation of (R)-2-(1-aminoethyl)-4-fluorophenol

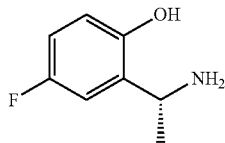

(S)—N—((R)-1-(2-benzyloxy-5-fluorophenylethyl)-2-methylpropyl-2-sulfonamide (82 g, 235 mmol) was dissolved in dichloromethane (80 mL), and a solution of boron tribromide in dichloromethane (1M, 470 mL) was added on ice bath. The reaction was stirred on ice bath for 2 hours and quenched with methanol. The mixture was extracted with ethyl acetate and water, and the aqueous phase was extracted twice with ethyl acetate. The organic phases were combined and dried over anhydrous sodium sulfate. The solvent was evaporated under reduced pressure and the residue was stirred in petroleum ether. The supernatant was discarded, to obtain a brown solid (21.3 g, 137 mmol, 58% yield).

MS (ESI) m/z=156 (M+1)$^+$.

(5) Preparation of benzyl (R)-(1-(5-fluoro-2-hydroxyphenyl) ethyl)carbamate

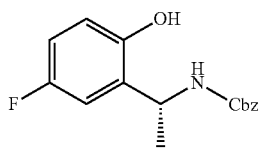 [SMILES: C[C@@H](NC(=O)OCc1ccccc1)c1cc(F)ccc1O]

(R)-2-(1-aminoethyl)-4-fluorophenol (21 g, 135 mmol) was dissolved in tetrahydrofuran (50 mL), and triethylamine (56.6 mL, 406 mmol) and benzyloxycarbonyl succinimide (43.9 g, 176 mmol) were added. After stirring for 1 hour, the mixture was extracted with ethyl acetate and water, and then the aqueous phase was extracted twice with ethyl acetate. The organic phases were combined and dried over anhydrous sodium sulfate. The solvent was evaporated under reduced pressure and the residue was purified by column chromatography (PE/EA=5/1) to obtain benzyl (R)-(1-(5-fluoro-2-hydroxyphenyl)ethyl)carbamate (10.1 g, 34.8 mmol, yield 40%)

MS (ESI) m/z=290 (M+1)$^+$.

(6) Preparation of benzyl (R)-(1-(2-(3-((tert-butoxycarbonyl)amino)propoxy)-5-fluorophenyl) ethyl) carbamate

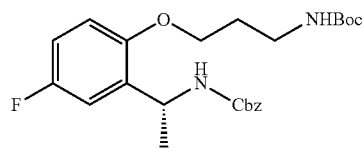 [SMILES: C[C@@H](NC(=O)OCc1ccccc1)c1cc(F)ccc1OCCCNC(=O)OC(C)(C)C]

The same procedure as that in step 6 to step 7 of Example 3, except for using benzyl (R)-(1-(5-fluoro-2-hydroxyphenyl)ethyl)carbamate (1 g, 3.46 mmol) instead of phenyl 5-fluoro-2-hydroxyphenyl(methyl)carbamate, to obtain benzyl (R)-(1-(2-(3-((tert-butoxycarbonyl) amino)propoxy)-5-fluorophenyl) ethyl)carbamate (1.01 g, 2.24 mmol, yield 65%).

MS (ESI) m/z=447 (M+1)$^+$.

(7) Preparation of tert-butyl (R)-(3-(2-(1-aminoethyl)-4-fluorophenoxy)propyl)carbamate

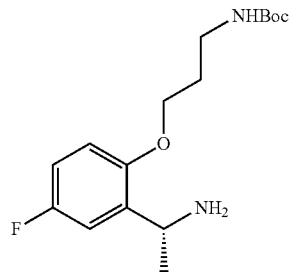 [SMILES: C[C@@H](N)c1cc(F)ccc1OCCCNC(=O)OC(C)(C)C]

Benzyl (R)-(1-(2-(3-((tert-butoxycarbonyl)amino)propoxy)-5-fluorophenyl)ethyl) carbamate (600 mg, 1.34 mmol) was dissolved in methanol (10.0 ml), then 10% palladium on carbon catalyst (150 mg) was added. The reaction was stirred for 2 hours under hydrogen atmosphere. After the reaction was completed, the palladium on carbon catalyst was removed by filtration, and the filtrate was spin-dried using a rotary evaporator to obtain tert-butyl (R)-(3-(2-(1-aminoethyl)-4-fluorophenoxy)propyl)carbamate (398 mg, 1.28 mmol, 95% yield).

MS (ESI) m/z=313 (M+1)$^+$.

(8) Preparation of allyl (R)-(1-(2-(3-((tert-butoxycarbonyl)amino)propoxy)-5-fluorophenyl)ethyl) carbamate

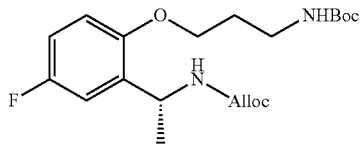

Tert-butyl (R)-(3-(2-(1-aminoethyl)-4-fluorophenoxy)propyl)carbamate (300 mg, 0.96 mmol) was dissolved in tetrahydrofuran (5 mL), then allyloxycarbonyl chloride (116 mg, 0.96 mmol) was added. Then an aqueous solution (5 mL) of sodium bicarbonate (161 mg, 1.92 mmol) was added on ice bath. The mixture was stirred at room temperature for 2 hours. After the reaction was completed, the mixture was extracted with ethyl acetate and water, and the aqueous phase was extracted twice with ethyl acetate. The organic phases were combined and dried over anhydrous sodium sulfate. The solvent was evaporated under reduced pressure and the residue was purified by column chromatography (PE/EA=4/1) to obtain allyl (R)-(1-(2-(3-((tert-butoxycarbonyl)amino)propoxy)-5-fluorophenyl)ethyl)carbamate (280 mg, 0.71 mmol, 74% yield).

MS (ESI) m/z (M+1=397)

(9) Preparation of allyl (R)-(1-(2-(3-aminopropoxy)-5-fluorophenyl)ethyl)carbamate

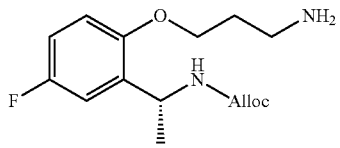

Allyl (R)-(1-(2-(3-((tert-butoxycarbonyl)amino)propoxy)-5-fluorophenyl)ethyl) carbamate (280 mg, 0.57 mmol) was dissolved in TFA (3 mL) and stirred at room temperature for 2 hours. Then, the solvent was removed by a rotary evaporator to obtain the trifluoroacetate salt of allyl (R)-(1-(2-(3-aminopropoxy)-5-fluorophenyl)ethyl)carbamate (290 mg, 0.54 mmol, yield 96%).

MS (ESI) m/z (M+1=297)

(10) Preparation of allyl (R)-(1-(2-(3-((6-chloropyrido[3,2-D]pyrimidin-4-yl)amino)propoxy)-5-fluorophenyl)ethyl)carbamate

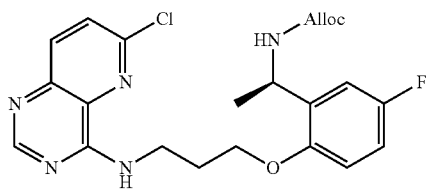

6-chloro-pyrido[3,2-D]pyrimidin-4(3H)-one (132 mg, 0.73 mmol) was added to a solution of DIEPA (282 mg, 2.18 mmol) and PyBOP (454 mg, 0.87 mmol) in DMF, and then the trifluoroacetate salt of allyl (R)-(1-(2-(3-aminopropoxy)-5-fluorophenyl)ethyl)carbamate (280 mg, 0.73 mmol) was added and stirred at room temperature for 5 hours. The mixture was extracted with ethyl acetate and water, and then the aqueous phase was extracted twice with ethyl acetate. The organic phases were combined and dried over anhydrous sodium sulfate. The solvent was evaporated under reduced pressure and the residue was purified by column chromatography (PE/EA=1/1) to obtain allyl (R)-(1-(2-(3-((6-chloropyrido[3,2-D]pyrimidin-4-yl)amino)propoxy)-5-fluorophenyl)ethyl)carbamate (205 mg, 0.33 mmol, yield 46%, purity 75%).

MS (ESI) m/z=460 (M+1)$^+$.

(11) Preparation of (R)—N-(3-(2-(1-aminoethyl)-4-fluorophenoxy)propyl)-6-chloropyrido[3,2-D]pyrimidine-4-amine

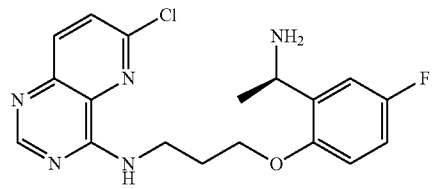 [SMILES: C[C@@H](N)c1cc(F)ccc1OCCCNc1ncnc2ccc(Cl)nc12]

Tetrakis(triphenylphosphine)palladium was added to a solution of allyl (R)-(1-(2-(3-((6-chloropyrido[3,2-D]pyrimidin-4-yl)amino)propoxy)-5-fluorophenyl)ethyl) carbamate (205 mg, 0.33 mmol) and morpholine (291 mg, 3.34 mmol) in tetrahydrofuran (3 mL), and stirred under nitrogen at room temperature for 16 hours. After the reaction was completed, the solvent was removed by a rotary evaporator, and the residue was purified by reverse-phase MPLC (acetonitrile/purified water) to obtain (R)—N-(3-(2-(1-aminoethyl)-4-fluorophenoxy)propyl)-6-chloropyrido[3,2-D]pyrimidine-4-amine (130 mg, 0.29 mmol, yield 88%, purity 85%).

MS (ESI) m/z=376 (M+1)$^+$.

(12) Preparation of (R)-6-fluoro-3-methyl-10-oxa-2,14,16,18,22-pentaazatetracyclo [13.6.2.0$^{4,9}$.0$^{19,23}$] tricosane-1 (22),4,6,8,15(23),16,18,20-octane

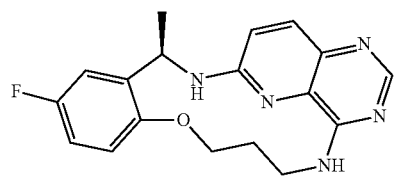 [SMILES: C[C@H]1Nc2ccc3ncnc(c3n2)NCCCOc2ccc(F)cc21]

Cesium carbonate (104 mg, 0.32 mmol) was added to a solution of (R)—N-(3-(2-(1-aminoethyl)-4-fluorophenoxy)propyl)-6-chloropyrido[3,2-D]pyrimidine-4-amine (40 mg, 0.11 mmol), Sphos (8.7 mg, 21 µmol) and Pd$_2$(dba)$_3$ (9.75 mg, 11 µmol) in toluene/tert-butanol (6 mL/3 mL). The mixture was stirred under nitrogen atmosphere at 110° C. for 16 hours. After the reaction was completed, the solvent was removed by a rotary evaporator, and the residue was purified by reverse phase MPLC (acetonitrile/purified water) to obtain (R)-6-fluoro-3-methyl-10-oxa-2,14,16,18,22-pentaazatetracyclo[13.6.2.0⁴,⁹.0¹⁹,²³;]tricosane-1(22),4,6,8,15 (23),16,18,20-octane (2.0 mg, 5.8 umol, yield 5.4%).

MS (ESI) m/z=340 (M+1)⁺.

¹HNMR (400 MHz, MeOD): δ=8.12 (s, 1H), 7.62 (d, J=9.2 Hz, 1H), 7.14 (dd, J=9.6, 3.2 Hz, 1H), 6.98 (d, J=9.2 Hz, 2H), 6.84-6.89 (m, 1H), 5.70-5.76 (m, 1H), 4.49-4.56 (m, 2H), 3.69 (m, 2H), 2.18-2.33 (m, 2H), 1.50 (d, J=7.2 Hz, 3H).

Example 18. Preparation of (R,R)-6,16-difluoro-3, 13-dimethyl-10-oxa-2,14,18,22-tetraazatetracyclo [13.6.2.0⁴,⁹.0¹⁹,²³]tricosane-1(22),4,6,8,15(23),16, 18,20-octane

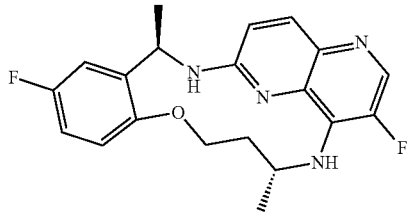 [SMILES: C[C@@H]1CCOc2ccc(F)cc2[C@@H](C)Nc2ccc3ncc(F)c(c3n2)N1]

(1) Preparation of 2,8-dichloro-7-fluoro-1,5-naphthyridine

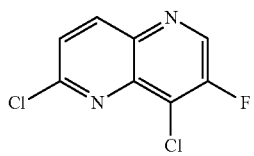 [SMILES: Fc1cnc2ccc(Cl)nc2c1Cl]

3-Fluoro-6-methoxy-1,5-diazasodium-4-phenol (0.97 g, 5 mmol) was added to DMF (10 mL), and then phosphorus oxychloride (3.07 g, 20 mmol) was added dropwise slowly, and stirred at 100° C. for 16 hours. The reaction was stopped, and after cooling naturally to room temperature, water was added. The mixture was extracted with ethyl acetate, and the organic phase was collected. The solvent was removed by a rotary evaporator, and the residue was separated by silica gel column chromatography (PE:EA=5: 1) to obtain 2,8-dichloro-7-fluoro-1,5-naphthyridine (0.74 g, 3.41 mmol, 68% yield).

MS (ESI) m/z=218 (M+1)⁺.

(2) Preparation of benzyl (R)-(1-(2-((R)-4-(2-(tert-butoxycarbonyl)amino)butoxy)-5-fluorophenyl) ethyl)carbamate

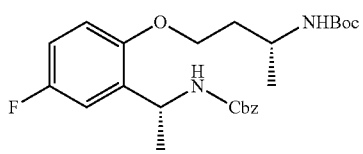 [SMILES: C[C@H](CCOc1ccc(F)cc1[C@@H](C)NC(=O)OCc1ccccc1)NC(=O)OC(C)(C)C]

The same procedure as that in step 7 of Example 3, except for using benzyl (R)-(1-(5-fluoro-2-phenyl)ethyl)carbamate (1.3 g, 4.5 mmol) instead of phenyl 5-fluoro-2-hydroxyphenyl(methyl)carbamate, and using (R)-3-((tert-butoxycarbonyl)amino) propylmethanesulfonate (1.8 g, 6.7 mmol) instead of 3-((tert-butoxycarbonyl)amino) propylmethanesulfonate, to obtain benzyl (R)-(1-(2-((R)-4-(2-(tert-butoxycarbonyl) amino)butoxy)-5-fluorophenyl)ethyl)carbamate (1.37 g, 2.97 mmol, 66% yield).

MS (ESI) m/z=461 (M+1)⁺.

(3) Preparation of benzyl ((R)-1-(2-((R)-3-aminobutoxy)-5-fluorophenyl)ethyl)carbamate

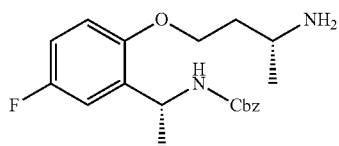

Benzyl (R)-(1-(2-((R)-4-(2-(tert-butoxycarbonyl)amino) butoxy)-5-fluorophenyl)ethyl) carbamate (500 mg, 1.1 mmol) was dissolved in DCM (10 mL), TFA (4 mL) was added and stirred at room temperature for 2 hours. The solvent was then removed with a rotary evaporator to obtain benzyl ((R)-1-(2-((R)-3-aminobutoxy)-5-fluorophenyl) ethyl)carbamate (390 mg, 1.1 mmol, yield 99%).

MS (ESI) m/z=361 (M+1)⁺.

(4) Preparation of benzyl ((R)-1-(2-((R)-3-((6-chloro-3-fluoro-1,5-naphthyridin-4-yl)amino) butoxy)-5-fluorophenyl)ethyl)carbamate

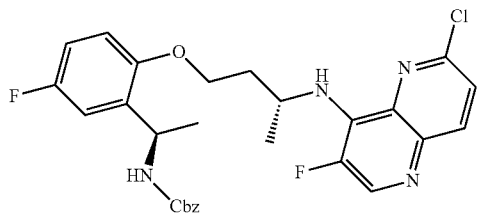 [SMILES: C[C@H](CCOc1ccc(F)cc1[C@@H](C)NC(=O)OCc1ccccc1)Nc1c(F)cnc2ccc(Cl)nc12]

Benzyl ((R)-1-(2-((R)-3-aminobutoxy)-5-fluorophenyl) ethyl)carbamate (209 mg, 1 mmol) was added to NMP (5 mL), then DIPEA (5 mL) was added thereto, and stirred at 120° C. for 16 hours. Then the solvent was evaporated under reduced pressure, and the residue was purified by column chromatography (PE/EA=1/1) to obtain benzyl ((R)-1-(2-((R)-3-((6-chloro-3-fluoro-1,5-naphthyridin-4-yl)amino)butoxy)-5-fluorophenyl)ethyl) carbamate (300 mg, 0.55 mmol, yield 55%, purity 75%)

MS (ESI) m/z=542 (M+1)⁺.

(5) Preparation of N—((R)-4-(2-((R)-1-aminoethyl)-4-fluorophenoxy)butan-2-yl)-6-chloro-3-fluoro-1,5-naphthyridine-4-amine

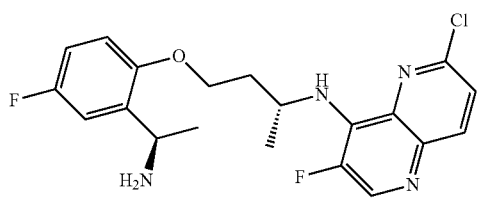 [SMILES: C[C@H](CCOc1ccc(F)cc1[C@@H](C)N)Nc1c(F)cnc2ccc(Cl)nc12]

Benzyl ((R)-1-(2-((R)-3-((6-chloro-3-fluoro-1,5-naphthyridin-4-yl)amino)butoxy)-5-fluorophenyl)ethyl) carbamate (300 mg, 0.55 mmol) was dissolved in a solution of acetic acid (4 mL), hydrobromic acid (2 mL) was slowly added dropwise, and then stirred under a nitrogen atmosphere at room temperature for 3 hours. After the reaction was completed, the solvent was removed by a rotary evaporator, and the crude product was washed with petroleum ether to obtain N—((R)-4-(2-((R)-1-aminoethyl)-4-fluorophenoxy)butan-2-yl)-6-chloro-3-fluoro-1,5-naphthyridine-4-amine (220 mg, 0.55 mmol, yield 99%)

MS (ESI) m/z=407 (M+1)$^+$.

(6) Preparation of (R,R)-6,16-difluoro-3,13-dimethyl-10-oxa-2,14,18,22-tetraazatetracyclo [13.6.2.0$^{4,9}$.0$^{19,23}$]tricosane-1(22),4,6,8,15(23),16,18,20-octane

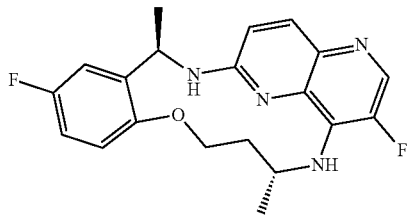 [SMILES: C[C@@H]1CCOc2ccc(F)cc2[C@@H](C)Nc2ccc3ncc(F)c(c3n2)N1]

Cesium carbonate (700 mg, 2.07 mmol) was added to a solution of N—((R)-4-(2-((R)-1-aminoethyl)-4-fluorophenoxy)butan-2-yl)-6-chloro-3-fluoro-1,5-naphthyridine-4-amine (220 mg, 0.54 mmol), Sphos (22 mg, 50 umol) and Sphos PdG3 (43 mg, 50 μmol) in toluene/tert-butanol (3 mL/3 mL). The mixture was stirred under nitrogen atmosphere at 100° C. for 16 hours. After the reaction was completed, the solvent was removed by a rotary evaporator, and the residue was purified by reverse phase MPLC (acetonitrile/purified water) to obtain (R,R)-6,16-difluoro-3,13-dimethyl-10-oxa-2,14,18,22-tetraazatetracyclo [13.6.2.0$^{4,9}$.0$^{19,21}$]tricosane-1(22),4,6,8,15(23),16,18,20-octane (16.3 mg, 44 μmol, yield 8.2%).

MS (ESI) m/z=371 (M+1)$^+$.
$^1$HNMR (400 MHz, CDCl$_3$): δ=8.25-8.27 (m, 1H), 8.01 (d, J=9.0 Hz, 1H), 6.85-6.88 (m, 1H), 6.70-6.81 (m, 3H), 5.05-5.10 (m, 1H), 4.85-4.89 (m, 1H), 4.48-4.51 (m, 1H), 4.22-4.27 (m, 1H), 4.08-4.12 (m, 1H), 2.13-2.20 (m, 1H), 1.76-1.80 (m, 1H), 1.70 (d, J=6.7 Hz, 3H), 1.40 (d, J=6.7 Hz, 3H).

Example 19. Preparation of (6R,16R)-9,19-difluoro-16-methyl-13-oxa-2,17,21,25-tetraazapentacyclo [16.6.2.0$^{2,6}$.0$^{7,12}$.0$^{22,26}$]hexacosane-1(25),7,9,11,18 (26),19,21,23-octane

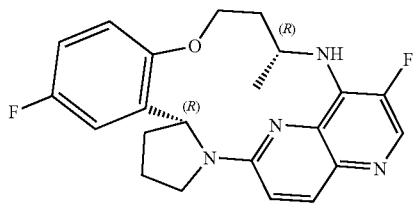

(1) Preparation of 3-fluoro-4-(((R)-4-(2-((R)-1-(benzyloxycarbonyl)tetrahydropyrrol-2-yl)-4-fluorophenoxy)butyl-2-yl)amino)-6-chloro-1,5-dinaphthyridine

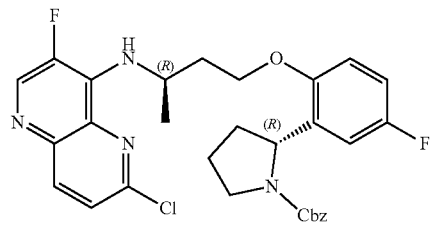

Benzyl (R)-phenyl 2-(2-((R)-3-aminobutoxy)-5-fluorophenyl)tetrahydropyrrole-1-carboxylate (178 mg, 0.46 mmol), and 2,8-dichloro-7-fluoro-1,5-naphthyridine (100 mg, 0.46 mmol) were added to NMP (5 mL), and then DIPEA (5 mL) was added thereto, and stirred at 120° C. for 16 hours. Then the solvent was evaporated under reduced pressure, and the residue was purified by column chromatography (PE/EA=1/1) to obtain 3-fluoro-4-(((R)-4-(2-((R)-1-(benzyloxycarbonyl)tetrahydropyrrol-2-yl)-4-fluorophenoxy)butyl-2-yl)amino)-6-chloro-1,5-naphthyridine (119 mg, 0.21 mmol, 46% yield).

MS (ESI) m/z=568 (M+1)$^+$.

(2) Preparation of 6-chloro-3-fluoro-N—((R)-4-(4-fluoro-2-((R)-tetrahydropyrrol-2-yl)phenoxy) butyl-2-yl)-1,5-naphthyridine-4-amine

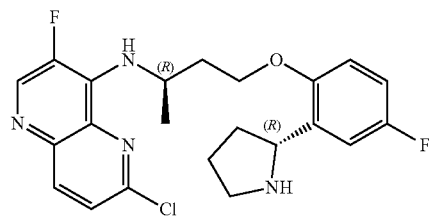

3-fluoro-4-(((R)-4-(2-((R)-1-(benzyloxycarbonyl)tetrahydropyrrol-2-yl)-4-fluorophenoxy) butyl-2-yl)amino)-6-chloro-1,5-naphthyridine (119 mg, 0.21 mmol) was dissolved in acetic acid (4 mL) solution, hydrobromic acid (2 mL) was slowly added dropwise, and then stirred at room temperature under nitrogen atmosphere for 3 hour. After the reaction was completed, the solvent was removed by a rotary evaporator, and the crude product was washed with petroleum ether to obtain 6-chloro-3-fluoro-N—((R)-4-(4-fluoro-2-((R)-tetrahydropyrrol-2-yl) phenoxy)butyl-2-yl)-1,5-naphthyridine-4-amine (91 mg, 0.21 mmol, yield 99%)

MS (ESI) m/z=433 (M+1)$^+$.

(3) Preparation of (6R,16R)-9,19-difluoro-16-methyl-13-oxa-2,17,21,25-tetraazapentacyclo[16.6.2.0$^{2,6}$.0$^{7,12}$.0$^{22,26}$]hexacosane-1(25),7,9,11,18(26),19,21,23-octane

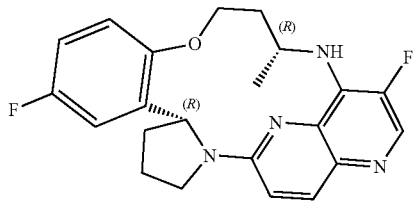

Cesium carbonate (274 mg, 0.84 mmol) was added to a solution of 6-chloro-3-fluoro-N—((R)-4-(4-fluoro-2-((R)-tetrahydropyrrol-2-yl)phenoxy)butyl-2-yl)-1,5-naphthyridine-4-amine (91 mg, 0.21 mmol), Sphos (9 mg, 21 μmol) and Sphos PdG3 (17 mg, 21 μmol) in toluene/tert-butanol (3 mL/3 mL). The mixture was stirred under nitrogen atmosphere at 100° C. for 16 hours. After the reaction was completed, the solvent was removed by a rotary evaporator, and the residue was purified by reverse phase MPLC (acetonitrile/purified water) to obtain (6R,16R)-9,19-difluoro-16-methyl-13-oxa-2,17,21,25-tetraazapentacyclo[16.6.2.0$^{2,6}$.0$^{7,12}$.0$^{22,26}$] hexacosane-1(25),7,9,11,18(26),19,21,23-octane (6.7 mg, 44 μmol, yield 8.1%).

MS (ESI) m/z=397 (M+1)$^+$.

$^1$HNMR (400 MHz, CDCl$_3$): δ=8.23 (d, J=7.5 Hz, 1H), 7.93 (d, J=9.0 Hz, 1H), 7.05-7.10 (m, 1H), 6.98-7.01 (m, 1H), 6.90-6.93 (m, 1H), 6.82-6.87 (m, 1H), 6.60 (d, J=9.0 Hz, 1H), 4.50-4.65 (m, 1H), 4.30-4.39 (m, 3H), 3.88-3.97 (m, 1H), 3.35-3.42 (m, 1H), 2.35-2.42 (m, 1H), 2.14-2.20 (m, 1H), 1.99-2.05 (m, 1H), 1.87-1.91 (m, 1H), 1.70-1.76 (m, 1H), 1.47-1.54 (m, 1), 1.00 (d, J=6.6 Hz, 3H).

To illustrate the beneficial effects of the present invention, the present invention provides the following test examples.

Test Example 1. Detection of TRK Inhibitory Activity

1. Experimental Materials Reagents:

| | |
|---|---|
| Microplate reader | TECAN Infinite M200 PRO |
| DMSO | MP/CAT NO. 196055 |
| MOPS | Sigma Cat#RDD003 Lot#SLBJ8407V |
| Triton-100 | Solarbio life science Cat#T8200 |
| MgCl$_2$•6H$_2$O | Chengdu Kelon Chemical Lot#20120728 |
| DTT | Sigma Cat#43815-1G |
| 384-well plate | Corning Cat#3574 |
| 96-well PCRplate | Axygen Cat#321-63-051 |
| ADP-Glo ™ Kinase Assay kit | Promega Cat#: V9102 |
| TRKA Protein (wild type) | abcam Cat#: ab60887 |
| Poly (4:1 Glu, Tyr)peptide | Signalchem Cat#P61-58, Lot#C1887-5 |

2. Experiment Method

An enzyme reaction buffer was prepared containing 25 mM MOPS, 5 mM MgCl$_2$, 500 μM DTT and 0.005% Triton, and then adjusted to pH 7.5.

The test compound was diluted with DMSO to 200 times of the desired final concentration, and mixed evenly, then 3 μL of the solution was pipetted to 117 μL of enzyme reaction buffer and mixed thoroughly. Then, 3 μL of the enzyme reaction buffer containing the test compound was pipetted to a 96-well PCR plate. The positive and negative control wells were filled with 3 μL of enzyme reaction buffer containing 2.5% DMSO, respectively. TRK protein was diluted to 0.4 ng/μL with the enzyme reaction buffer, and 6 μL of diluted TRK protein was added to each well except for the well for the blank control group, in which 6 μL of the enzyme reaction buffer was added. The reaction plate was centrifuged at 1000 rpm/min for 1 minute, and the compound and TRK were pre-incubated at room temperature for 10 minutes. A mixed solution with ATP at a concentration of 160 μM and substrate at a concentration of 1 μM was prepared with the enzyme reaction buffer, and 6 μL of the mixed solution was added to each reaction well. The reaction plate was centrifuged at 1000 rpm/min for 1 minute, and incubated at room temperature for 35 minutes. After the enzyme reaction was completed, 15 μL of ADP-Glo was added to each reaction well. The reaction plate was centrifuged at 1000 rpm/min for 1 minute, and incubated at room temperature for 40 minutes. Then 15 μL of the reaction solution from each well was transferred to a 384-well plate, and then 15 μL of detection substrate was added to each corresponding well of the 384-well plate. The 384-well plate was centrifuged at 1000 rpm/min for 1 minute, and incubated at room temperature for 40 minutes. After the reaction, a microplate reader was used to read the cold luminescence signal value in the 384-well plate.

3. Data Analysis

The residual viability percentage of each concentration was calculated with the following formula:

Residual viability (%)=100*(Lumin$_{compond}$−Lumin$_{blank\ control}$)/(Lumin$_{positive\ control}$−Lumin$_{blank\ control}$)

Then, GraphPad 5.0 was fitted to the effect curve to calculate the IC$_{50}$ value.

The compounds prepared in the examples were tested for TRK inhibitory activity according to the above method. The test results are shown in Table 1, in which the IC$_{50}$ of each compound was determined according to the description. In Table 1:

"+" means IC$_{50}$ value greater than 500 nM;

"++" means IC$_{50}$ value less than 500 nM and greater than 50 nM;

"+++" means IC$_{50}$ value less than 50 nM

NA means no data

TABLE 1

| Inhibitory activity of compounds on TRKA | | |
|---|---|---|
| Example | TRKA | TRKA (G667C) |
| 1 | +++ | +++ |
| 2 | +++ | +++ |
| 3 | +++ | +++ |
| 4 | ++ | NA |
| 5 | +++ | +++ |
| 6 | +++ | +++ |
| 7 | +++ | +++ |
| 8 | +++ | NA |
| 9 | +++ | + |
| 10 | ++ | NA |
| 11 | +++ | +++ |
| 12 | +++ | +++ |
| 13 | ++ | NA |
| 14 | ++ | NA |
| 15 | +++ | +++ |
| 16 | +++ | +++ |
| 17 | +++ | +++ |
| 18 | +++ | +++ |
| 19 | +++ | +++ |

The test shows that the compounds of the examples of the present invention have good TRK inhibitory activity and can be effectively used in the treatment of diseases related to abnormal TRK activity.

In summary, the novel compound of formula I disclosed in the present invention exhibits good TRK inhibitory activity and provides a new option for clinical treatment of diseases related to abnormal TRK activity.

Test Example 2. Cell Experiment

1. Experimental Materials and Reagents:
Cell lines: Ba/F3 ETV6-NTRK3-G623R cell line, Ba/F3 LMNA-NTRK1-G595R cell line, Ba/F3 LMNA-NTRK1-F589L cell line (RPMI1640+10% FBS medium); reagents and consumables: Fetus Bovine Serum FBS (GBICO, Cat #10099-141), CellTiter-Glo® Luminescent Cell Viability Assay (Promega, Cat #G7572), 96-well transparent flat bottom black wall plate (Corning® Cat #3603); Instrument: SpectraMax multi-label microplate reader, MD, 2104-0010A; $CO_2$ incubator, Thermo Scientific, Model 3100 Series; biological safety cabinet, Thermo Scientific, Model 1300 Series A2; inverted microscope, Olympus, CKX41SF; Refrigerator, SIEMENS, KK25E76TI.

2. Experiment Method
Cell culture and seeding: (1) cells in logarithmic growth phase were harvested and counted using a platelet counter. The cell viability was detected by trypan blue exclusion method to ensure that the cell viability was above 90%. (2) The cell concentration was adjusted; and 90 μl of cell suspension was added to the 96-well plate. (3) The cells in the 96-well plate were incubated overnight at 37° C., 5% $CO_2$, and 95% humidity.

Drug dilution and dosing: (1) a 10-fold volume of the drug solution at the highest concentration of 10 M was prepared and serially diluted with 3.16-fold dilution to produce 9 concentrations. 10 μl of drug solution was added to each well in a 96-well plate inoculated with cells, triplicate per concentration. (2) The cells in the 96-well plate added with drugs were placed under 37° C., 5% $CO_2$, and 95% humidity to continue culturing for 72 hours, and then CTG analysis was performed.

End-point for reading: (1) The CTG reagent was thawed and the cell plate was equilibrated to room temperature for 30 minutes. (2) Equal volume of CTG solution was added to each well. (3) The plated was shaken on an orbital shaker for 5 minutes to lyse the cells. (4) The cell plate was placed at room temperature for 20 minutes to stabilize the cold light signal. (5) The cold light value was read.

3. Data Analysis
GraphPad Prism 7.0 software was used to analyze the data, and nonlinear S-curve regression was fitted the data to get the dose-effect curve, and the $IC_{50}$ value was calculated therefrom.

Cell survival (%)=($Lum_{test\ drug}$−$Lum_{culture\ control}$)/($Lum_{cell\ control}$−$Lum_{culture\ control}$)×100%.

TABLE 2

Inhibitory activity of the example compounds on TRKA mutant cell lines

| Cell | Compund | IC90 (μM) | IC50 (μM) |
|---|---|---|---|
| Ba/F3 ETV6-NTRK3-G623R | Example 1 | 0.0423 | 0.0173 |
|  | Example 6 | 0.0942 | 0.0421 |
|  | Example 7 | 0.0087 | 0.0036 |
|  | RXDX-101 | 0.8430 | 0.4665 |
| Ba/F3 LMNA-NTRK1-G595R | Example1 | 0.0832 | 0.0025 |
|  | RXDX-101 | 6.1243 | 1.7277 |
| Ba/F3 LMNA-NTRK1-F589L | Example 1 | 0.0171 | 0.0038 |
|  | RXDX-101 | 0.0014 | <0.001 |

The tests show that the compounds of the examples of the present invention have a significantly improved inhibitory effect on the growth of TRKA mutant cells compared with the positive control compound, and can be effectively used in the treatment of diseases related to abnormal TRK activity.

Test Example 3. Drug Efficacy Test for TRKA In Vivo

Drug Efficacy Test 1 The compound of Example 1 inhibits the growth of Balb/c Nude mouse tumors (NIH-3T3ATRKA G595R cells)

1. Experimental Materials
NIH-3T3 ATRKA G595R cells are polyclonal stable transfected cell lines constructed based on TRKA mutation by our laboratory. Balb/c Nude mice, female, 6-8 weeks old, weighing 18-22 grams, were purchased from Chengdu Dashuo Experimental Animal Co., Ltd.

2. Experimental Method
NIH-3T3 ATRKA G595R cells in the logarithmic growth phase were collected, counted and adjusted to a suitable cell density. 0.1 mL cell suspension ($2 \times 10^6$ cells) was inoculated subcutaneously into the right back of each mouse. When the average tumor volume reached about 100 $mm^3$, mice were randomly divided into groups (m=6) for administrating the compound of Example 1 in solvent PEG400:HPBCD (20%, W/V) (3:1).

During the experiment, animals were observed for activities once a day, weighed before each administration, and measured for the long and short diameters of tumors with vernier calipers three times a week. At the end of the experiment, all surviving experimental animals were sacrificed.

3. Data Analysis
Tumor volume was calculated using formula: V=0.5 (a×$b^2$), wherein a and b represent the long and short diameters of the tumor, respectively.

Graph Pad Prism 6.0 was used for graph analysis. The results are shown in FIG. 1.

Tests show that the compounds of the present invention can significantly inhibit the growth of tumors in mice, and can be effectively used in the treatment of diseases related to abnormal TRK activity.

Drug Efficacy Test 2: The compound of Example 1 inhibits the growth of Balb/c Nude mouse tumors (BA/F3 ETV6-NTRK3 G623R cells)

1. Experimental Materials
BA/F3 ETV6-NTRK3 G623R cells are polyclonal stable transfected cell lines constructed based on TRKA mutation by our laboratory. Balb/c Nude mice, female, 6-8 weeks old, weighing 18-22 grams, were purchased from Chengdu Dashuo Experimental Animal Co., Ltd.

2. Experimental Method
BA/F3 ETV6-NTRK3 G623R cells in logarithmic growth phase were collected, counted and adjusted to a suitable cell density. 0.1 mL cell suspension ($2 \times 10^6$ cells) was inoculated subcutaneously into the right back of each mouse. When the average tumor volume reached about 100 mm³, mice were randomly divided into groups (m=5) for administrating the compound of Example 1 in solvent PEG400:HPBCD (20%, W/V) (3:1).

During the experiment, animals were observed for activities once a day, weighed before each administration, and measured for the long and short diameters of tumors with vernier calipers three times a week. At the end of the experiment, all surviving experimental animals were sacrificed.

3. Data Analysis

Tumor volume was calculated using formula: V=0.5 (a×b²), wherein a and b represent the long and short diameters of the tumor, respectively.

Figure 2:
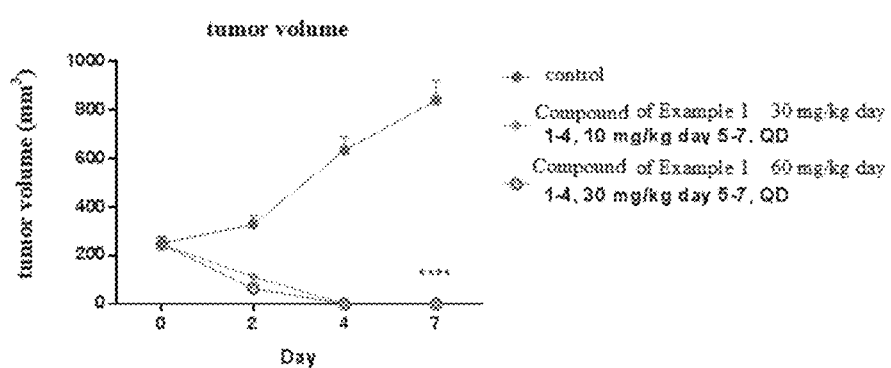
FIG. 2 shows the inhibition of the compound of Example 1 on the growth of Balb/c Nude mouse tumors (BA/F3 ETV6-NTRK3 G623R cells).

GraphPadPrism6.0 was used for graph analysis. The results are shown in FIG. 2.

Tests show that the compounds of the present invention can significantly inhibit the growth of tumors in mice, and can be effectively used in the treatment of diseases related to abnormal TRK activity.

Drug Efficacy Test 3: The compound of Example 1 inhibits the growth of SCID mouse tumors (BA/F3 ETV6-NTRK3 G623R cells)

1. Experimental Materials

BA/F3 ETV6-NTRK3 G623R cells are polyclonal stable transfected cell lines constructed based on TRKA mutation by our laboratory. SCID mice, female, 6-8 weeks old, weighing 18-22 grams, were purchased from Chengdu Dashuo Experimental Animal Co., Ltd.

2. Experimental Method

BA/F3 ETV6-NTRK3 G623R cells in logarithmic growth phase were collected, counted and adjusted to a suitable cell density. 0.1 mL cell suspension (2×10⁶ cells) was inoculated subcutaneously into the right back of each mouse. When the average tumor volume reached about 300 mm³, mice were randomly divided into groups (m=5) for administrating the compound of Example 1 in solvent PEG400:HPBCD (20%, W/V) (3:1).

During the experiment, animals were observed for activities once a day, weighed before each administration, and measured for the long and short diameters of tumors with vernier calipers three times a week. At the end of the experiment, all surviving experimental animals were sacrificed.

3. Data Analysis

Tumor volume was calculated using formula: V=0.5 (a×b²), wherein a and b represent the long and short diameters of the tumor, respectively.

Figure 3:
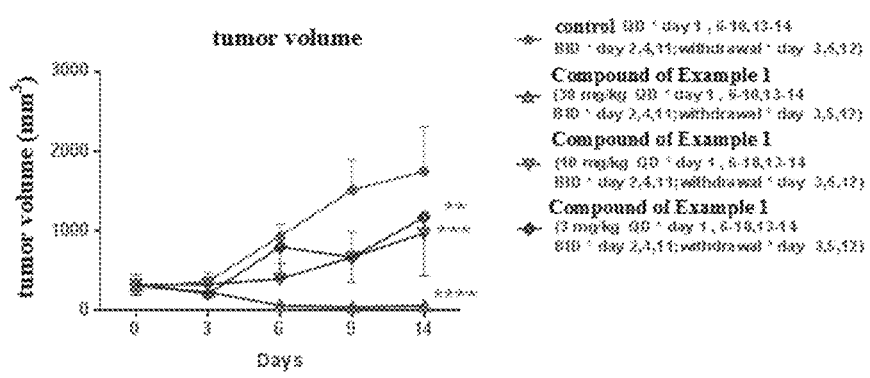
FIG. 3 shows the inhibition of the compound of Example 1 on the growth of SCID mouse tumors (BA/F3 ETV6-NTRK3 G623R cells).

Graph Pad Prism 6.0 was used for graph analysis. The results are shown in FIG. 3.

Tests show that the compounds of the present invention can significantly inhibit the growth of tumors in mice, and can be effectively used in the treatment of diseases related to abnormal TRK activity.

In summary, the new compound as shown in formula I disclosed in the present invention exhibits an excellent TRK inhibitory activity, has a significant inhibitory effect on TRKA-mutant cell growth, and exhibits an excellent inhibitory effect on in vivo tumor growth, thus providing a new choice for the clinical treatment of diseases associated with abnormal TRK activity.

The invention claimed is:

1. The compound as shown in formula I:

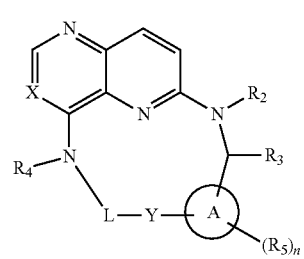

Formula I wherein

X is selected from $CR_1$ or N;

$R_1$ is selected from hydrogen, halogen, $C_{1-10}$ alkyl, $C_{2-10}$ alkenyl, $C_{2-10}$ alkynyl, 3-10 membered cycloalkyl, 3-10 membered heterocycloalkyl, —CN, —NO$_2$, —OR$_a$, —OC(O)R$_a$, —OC(O)NR$_a$R$_b$, —OS(O)$_2$R$_a$, —SR$_a$, —S(O)$_2$R$_a$, —S(O)$_2$NR$_a$R$_b$, —OS(O)$_2$NR$_a$R$_b$, —C(O)R$_a$, —C(O)OR$_a$, —C(O)NR$_a$R$_b$, —NR$_a$R$_b$, —NR$_a$C(O)R$_b$, —NR$_a$C(O)OR$_b$, —NR$_a$C(O)NR$_a$R$_b$, —NR$_a$S(O)$_2$R$_b$, and —NR$_a$S(O)$_2$NR$_a$R$_b$; wherein the alkyl, alkenyl, alkynyl, cycloalkyl, and heterocycloalkyl are substituted with m R$_c$;

$R_2$ is selected from hydrogen, $C_{1-10}$ alkyl, 3-10 membered cycloalkyl, 3-10 membered heterocycloalkyl, —S(O)$_2$R$_a$, —S(O)$_2$NR$_a$R$_b$, —C(O)R$_a$, —C(O)OR$_a$, and —C(O)NR$_a$R$_b$; wherein the alkyl, cycloalkyl, and heterocycloalkyl are substituted with m R$_c$;

$R_3$ is selected from hydrogen, halogen, $C_{1-10}$ alkyl, $C_{2-10}$ alkenyl, $C_{2-10}$ alkynyl, 3-10 membered cycloalkyl, 3-10 membered heterocycloalkyl, —CN, —NO$_2$, —OR$_a$, —C(O)R$_a$, —C(O)OR$_a$, —C(O)NR$_a$R$_b$, —NR$_a$R$_b$, and —NR$_a$C(O)R$_b$; wherein the alkyl, alkenyl, alkynyl, cycloalkyl, and heterocycloalkyl are substituted with m R$_c$;

or $R_2$ and $R_3$ are connected to form a 4-10-membered heterocycle; wherein the formed heterocycle is substituted with m R$_c$;

$R_4$ is selected from hydrogen, $C_{1-10}$ alkyl, 3-10 membered cycloalkyl, 3-10 membered heterocycloalkyl, —S(O)$_2$R$_a$, —S(O)$_2$NR$_a$R$_b$, —C(O)R$_a$, —C(O)OR$_a$, and —C(O)NR$_a$R$_b$; wherein the alkyl, cycloalkyl, and heterocycloalkyl are substituted with m R$_c$;

ring A is selected from a benzene ring, a naphthalene ring and a 5-10 membered aromatic heterocycle;

n is 1, 2, 3, or 4;

$R_5$ is independently selected from hydrogen, halogen, $C_{1-10}$ alkyl, $C_{2-10}$ alkenyl, $C_{2-10}$ alkynyl, 3-10 membered cycloalkyl, 3-10 membered heterocycloalkyl, —CN, —NO$_2$, —OR$_a$, —OC(O)R$_a$, —OC(O)NR$_a$R$_b$, —OS(O)$_2$R$_a$, —SR$_a$, —S(O)$_2$R$_a$, —S(O)$_2$NR$_a$R$_b$, —OS(O)$_2$NR$_a$R$_b$, —C(O)R$_a$, —C(O)OR$_a$, —C(O)NR$_a$R$_b$, —NR$_a$R$_b$, —NR$_a$C(O)R$_b$, —NR$_a$C(O)OR$_b$, —NR$_a$C(O)NR$_a$R$_b$, —NR$_a$S(O)$_2$R$_b$, and —NR$_a$S(O)$_2$NR$_a$R$_b$; wherein the alkyl, alkenyl, alkynyl, cycloalkyl, and heterocycloalkyl are substituted with m R$_c$;

Y is selected from O, S, —NR$_a$, and —C(R$_a$R$_b$)—;

L is selected from $C_{1-10}$ alkylene, $C_{2-10}$ alkenylene, and $C_{2-10}$ alkynylene; wherein the alkylene, alkenylene, and alkynylene are substituted with m R$_c$;

m is independently 0, 1, 2, 3, or 4;

$R_a$ and $R_b$ are independently selected from hydrogen, $C_{1-10}$ alkyl, $C_{2-10}$ alkenyl, $C_{2-10}$ alkynyl, 3-10 membered cycloalkyl, and 3-10 membered heterocycloalkyl; and $R_C$ is independently selected from $C_{1-10}$ alkyl, halogen, —CN, —NO$_2$, —OR$_a$, —OC(O)R$_a$, —OS(O)$_2$R$_a$, —SR$_a$, —S(O)$_2$R$_a$, —S(O)$_2$NR$_a$R$_b$, —C(O)R$_a$, —C(O)OR$_a$, —C(O)NR$_a$R$_b$, —NR$_a$R$_b$, —NR$_a$C(O)R$_b$, and —NR$_a$S(O)$_2$R$_b$, or a stereoisomer thereof, or a pharmaceutically acceptable salt thereof.

2. The compound according to claim 1, or a stereoisomer thereof, or a pharmaceutically acceptable salt thereof, wherein:

$R_1$ is selected from hydrogen, halogen, $C_{1-6}$ alkyl, $C_{2-6}$ alkenyl, $C_{2-6}$ alkynyl, 3-6 membered cycloalkyl, 3-6 membered heterocycloalkyl, —CN, —NO$_2$, —OR$_a$, —OC(O)R$_a$, —OC(O)NR$_a$R$_b$, —OS(O)$_2$R$_a$, —SR$_a$, —S(O)$_2$R$_a$, —S(O)$_2$NR$_a$R$_b$, —OS(O)$_2$NR$_a$R$_b$, —C(O)R$_a$, —C(O)OR$_a$, —C(O)NR$_a$R$_b$, —NR$_a$R$_b$, —NR$_a$C(O)R$_b$, —NR$_a$C(O)OR$_b$, —NR$_a$C(O)NR$_a$R$_b$, —NR$_a$S(O)$_2$R$_b$, and —NR$_a$S(O)$_2$NR$_a$R$_b$; wherein the alkyl, alkenyl, alkynyl, cycloalkyl, and heterocycloalkyl are substituted with m $R_c$;

$R_2$ is selected from hydrogen, $C_{1-6}$ alkyl, 3-6 membered cycloalkyl, 3-6 membered heterocycloalkyl, —S(O)$_2$R$_a$, and —C(O)R$_a$; wherein the alkyl, cycloalkyl, heterocycloalkyl are substituted with m $R_c$;

$R_3$ is selected from hydrogen, halogen, $C_{1-6}$ alkyl, $C_{2-6}$ alkenyl, $C_{2-6}$ alkynyl, 3-6 membered cycloalkyl, 3-6 membered heterocycloalkyl, —CN, —NO$_2$, —OR$_a$, —C(O)R$_a$, —C(O)OR$_a$, —C(O)NR$_a$R$_b$, —NR$_a$R$_b$, and —NR$_a$C(O)R$_b$; wherein the alkyl, alkenyl, alkynyl, cycloalkyl, heterocycloalkyl are substituted with m $R_c$;

or $R_2$ and $R_3$ are connected to form a 4-8 membered heterocycle; wherein the formed heterocycle is substituted with m $R_c$;

$R_4$ is selected from hydrogen, $C_{1-6}$ alkyl, 3-6 membered cycloalkyl, 3-6 membered heterocycloalkyl, —S(O)$_2$R$_a$, and —C(O)R$_a$; wherein the alkyl, cycloalkyl, and heterocycloalkyl are substituted with m $R_c$;

ring A is selected from a benzene ring and a 5-6 membered aromatic heterocycle;

n is 1, 2, or 3;

$R_5$ is independently selected from hydrogen, halogen, $C_{1-6}$ alkyl, $C_{2-6}$ alkenyl, $C_{2-6}$ alkynyl, 3-6 membered cycloalkyl, 3-6 membered heterocycloalkyl, —CN, —NO$_2$, —OR$_a$, —OC(O)R$_a$, —OS(O)$_2$R$_a$, —SR$_a$, —S(O)2R$_a$, —S(O)$_2$NR$_a$R$_b$, —C(O)R$_a$, —C(O)OR$_a$, —C(O)NR$_a$R$_b$, —NR$_a$R$_b$, —NR$_a$C(O)R$_b$, and —NR$_a$S(O)$_2$R$_b$; wherein the alkyl, alkenyl, alkynyl, cycloalkyl, and heterocycloalkyl are substituted with m $R_c$;

L is selected from $C_{1-6}$ alkylene, $C_{2-6}$ alkenylene and $C_{2-6}$ alkynylene; wherein the alkylene, alkenylene and alkynylene are substituted with m $R_c$;

m is independently 0, 1, 2, or 3; and $R_a$ and $R_b$ are independently selected from hydrogen, $C_{1-6}$ alkyl, $C_{2-6}$ alkenyl, $C_{2-6}$ alkynyl, 3-6 membered cycloalkyl, and 3-6 membered heterocycloalkyl.

3. The compound according to claim 2, or a stereoisomer thereof, or a pharmaceutically acceptable salt thereof, wherein:

$R_1$ is selected from hydrogen, halogen, $C_{1-6}$ alkyl, 3-6 membered cycloalkyl, 3-6 membered heterocycloalkyl, —CN, —NO$_2$, —OR$_a$, —OC(O)R$_a$, —OS(O)$_2$R$_a$, —SR$_a$, —S(O)$_2$R$_a$, —S(O)$_2$NR$_a$R$_b$, —C(O)R$_a$, —C(O)OR$_a$, —C(O)NR$_a$R$_b$, —NR$_a$R$_b$, —NR$_a$C(O)R$_b$, and —NR$_a$S(O)$_2$R$_b$; wherein the alkyl, cycloalkyl, and heterocycloalkyl are substituted with m $R_c$;

$R_2$ is selected from hydrogen, $C_{1-6}$ alkyl, 3-6 membered cycloalkyl, and 3-6 membered heterocycloalkyl; wherein the alkyl, cycloalkyl, and heterocycloalkyl are substituted with m $R_c$;

$R_3$ is selected from hydrogen, halogen, $C_{1-6}$ alkyl, 3-6 membered cycloalkyl, 3-6 membered heterocycloalkyl, —CN, —NO$_2$, —OR$_a$, —C(O)R$_a$, —C(O)OR$_a$, —C(O)NR$_a$R$_b$, and —NR$_a$R$_b$; wherein the alkyl, cycloalkyl, and heterocycloalkyl are substituted with m $R_c$;

or $R_2$ and $R_3$ are connected to form a 4-6 membered heterocycle; wherein the formed heterocycle is substituted with m $R_c$;

$R_4$ is selected from hydrogen, $C_{1-6}$ alkyl, —S(O)$_2$R$_a$, and —C(O)R$_a$; wherein the alkyl is substituted with m $R_c$;

n is 1 or 2;

$R_5$ is independently selected from hydrogen, halogen, $C_{1-6}$ alkyl, $C_{2-6}$ alkenyl, $C_{2-6}$ alkynyl, 3-6 membered cycloalkyl, 3-6 membered heterocycloalkyl, —CN, —NO$_2$, —OR$_a$, —SR$_a$, —S(O)$_2$R$_a$, —S(O)$_2$NR$_a$R$_b$, —C(O)R$_a$, —C(O)OR$_a$, —C(O)NR$_a$R$_b$, —NR$_a$R$_b$, —NR$_a$C(O)R$_b$, and —NR$_a$S(O)$_2$R$_b$; wherein the alkyl, alkenyl, alkynyl, cycloalkyl, and heterocycloalkyl are substituted with m $R_c$;

L is selected from $C_{1-6}$ alkylene; wherein the alkylene group is substituted with m $R_c$; and m is independently 0, 1, or 2.

4. The compound according to claim 3, or a stereoisomer thereof, or a pharmaceutically acceptable salt thereof, wherein:

$R_1$ is selected from hydrogen, halogen, $C_{1-6}$ alkyl, —CN, —NO$_2$, —OR$_a$, —C(O)R$_a$, —C(O)OR$_a$, —C(O)NR$_a$R$_b$, —NR$_a$R$_b$, —NR$_a$C(O)R$_b$; wherein the alkyl is substituted with m $R_c$;

$R_2$ is selected from hydrogen and $C_{1-6}$ alkyl; wherein the alkyl is substituted with m Rc;

$R_3$ is selected from hydrogen, halogen, $C_{1-6}$ alkyl, —CN, —NO$_2$, —OR$_a$, and —NR$_a$R$_b$; wherein the alkyl is substituted with m $R_c$;

or $R_2$ and $R_3$ are connected to form a 5-membered heterocycle; wherein the formed heterocycle is substituted with m $R_c$;

$R_4$ is selected from hydrogen and $C_{1-6}$ alkyl; wherein the alkyl is substituted with m Rc;

ring A is selected from a benzene ring and a pyridine ring;

$R_5$ is independently selected from hydrogen, halogen, $C_{1-6}$ alkyl, —CN, —NO$_2$, —OR$_a$, and —NR$_a$R$_b$; wherein the alkyl is substituted with m $R_c$;

$R_a$ and $R_b$ are independently selected from hydrogen and $C_{1-6}$ alkyl; and $R_c$ is independently selected from $C_{1-6}$ alkyl, halogen, —CN, —NO$_2$, —OR$_a$, and —NR$_a$R$_b$.

5. The compound according to claim 1, or a stereoisomer thereof, or a pharmaceutically acceptable salt thereof, wherein the compound as shown in formula I, or a stereoisomer thereof, or a pharmaceutically acceptable salt is shown in Formula II:

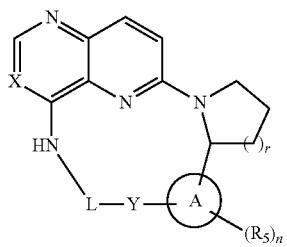

Formula II wherein
X is selected from $CR_1$ or N;
$R_1$ is selected from hydrogen, halogen, —CN, —C(O)$R_a$, —C(O)O$R_a$, and —C(O)N$R_aR_b$;
ring A is selected from a benzene ring, a naphthalene ring and a 5-10 membered aromatic heterocycle;
n is 1, 2, 3, or 4;
$R_5$ is independently selected from hydrogen and halogen;
Y is selected from 0, —$NR_a$—, and —C($R_aR_b$)—;
$R_a$ and $R_b$ are independently selected from hydrogen and $C_{1-10}$ alkyl;
L is selected from $C_{1-10}$ alkylene; wherein the alkylene is substituted with m $R_c$;
r is 0, 1, 2, 3 or 4; and
m is 0, 1, 2, 3 or 4.

6. The compound according to claim 5, or a stereoisomer thereof, or a pharmaceutically acceptable salt thereof, wherein the compound as shown in formula II, or a stereoisomer thereof, or a pharmaceutically acceptable salt thereof is:

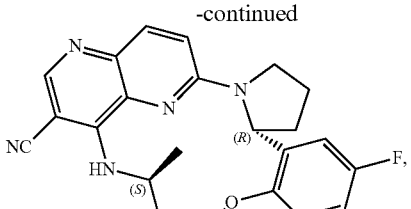

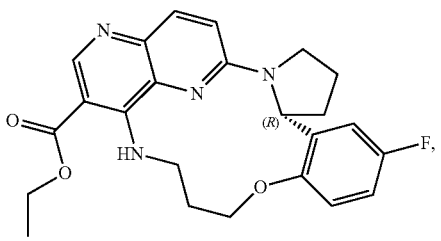

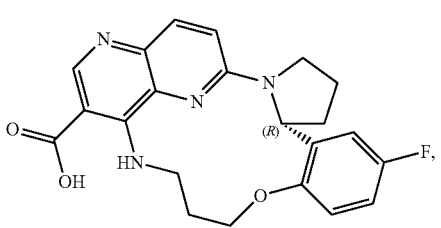

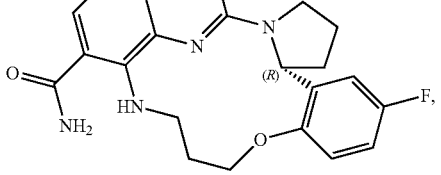

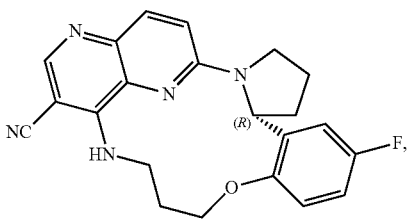

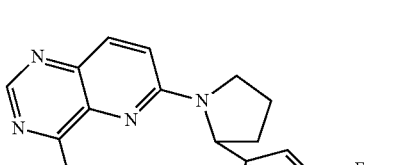

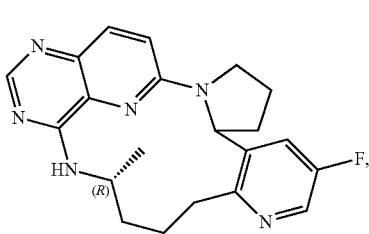

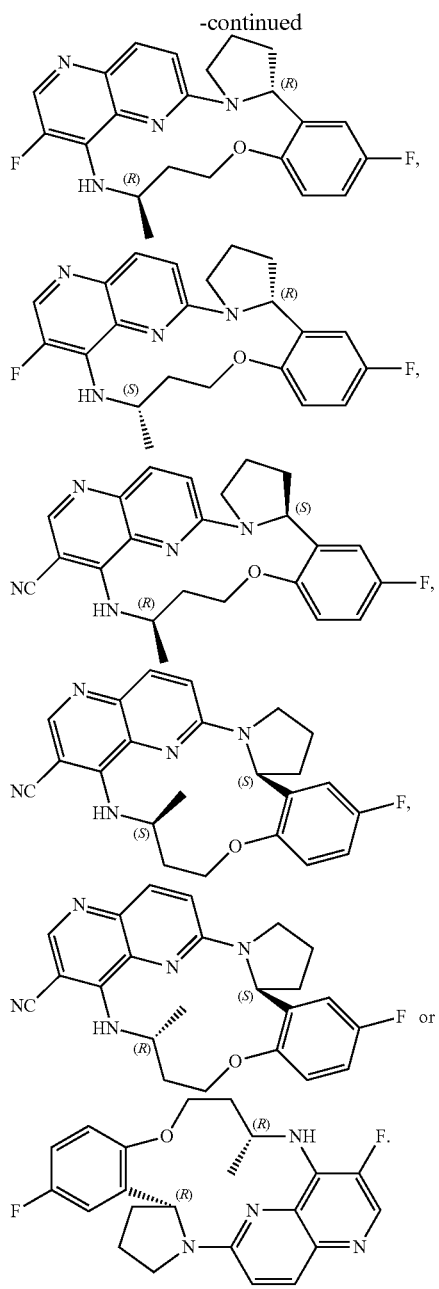

7. The compound according to claim 1, to or a stereoisomer thereof, or a pharmaceutically acceptable salt thereof, wherein the compound as shown in formula I, or a stereoisomer thereof, or a pharmaceutically acceptable salt is shown in Formula III:

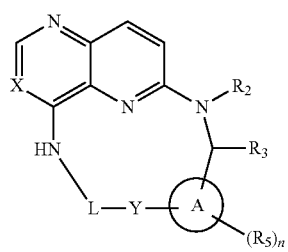

Formula III wherein
X is selected from $CR_1$ or N;
$R_1$ is selected from halogen and —CN;
ring A is selected from a benzene ring and a naphthalene ring;
n is 1, 2, 3 or 4;
$R_5$ is independently selected from hydrogen and halogen;
Y is selected from O and $—NR_a—$;
$R_a$ is selected from hydrogen and $C_{1-10}$ alkyl;
L is selected from $C_{1-10}$ alkylene; wherein the alkylene is substituted with m $R_c$; and
m is 0, 1, 2, 3 or 4.

8. The compound according to claim 7, or a stereoisomer thereof, or a pharmaceutically acceptable salt thereof, wherein the compound as shown in formula III, or a stereoisomer thereof, or a pharmaceutically acceptable salt thereof is:

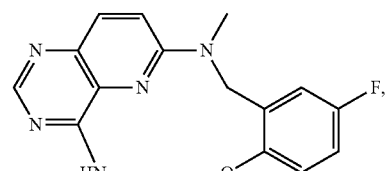

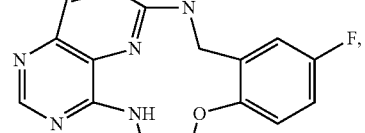

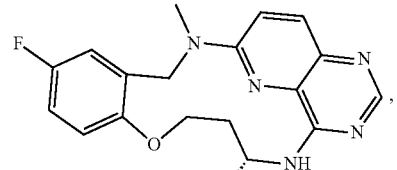

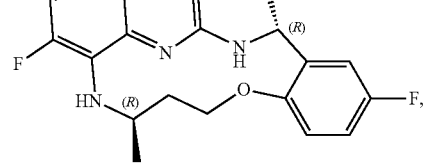

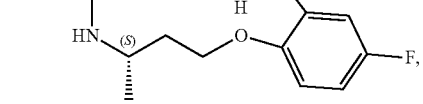

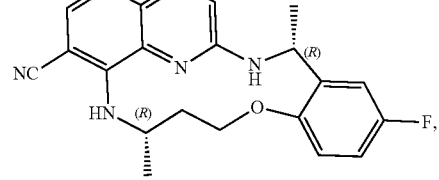

-continued

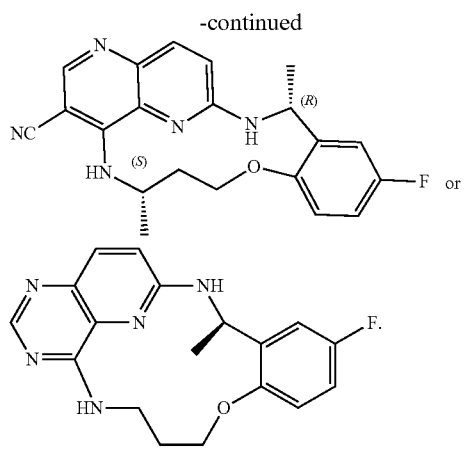

9. A method of inhibiting kinase, comprising administering a subject in need thereof the compound according to claim 1.

10. The method according to claim 9, wherein the kinase is a Trk kinase.

11. The method according to claim 10, wherein the Trk kinase is a Trk A kinase.

12. A method of treating a disease related to abnormal kinase activity, comprising administering the subject in need thereof the compound according claim 1.

13. The method according to claim 12, wherein the disease related to abnormal kinase activity is a disease related to abnormal Trk kinase activity.

14. The method according to claim 13, wherein the disease related to abnormal Trk kinase activity is any one or more of diseases related to neurodegenerative diseases, pain, cancers, and inflammation.

\* \* \* \* \*